United States Patent [19]

Hacohen et al.

[11] Patent Number: 6,060,275
[45] Date of Patent: May 9, 2000

[54] SPROUTY PROTEIN AND CODING SEQUENCE

[75] Inventors: Nir Hacohen, Cambridge, Mass.; Mark A. Krasnow, Stanford, Calif.

[73] Assignee: The Board of Trustees of the Leland Standord Junior University, Stanford, Calif.

[21] Appl. No.: 08/965,903

[22] Filed: Nov. 7, 1997

Related U.S. Application Data

[60] Provisional application No. 60/030,232, Nov. 7, 1996.
[51] Int. Cl.⁷ .............................. C12N 5/10; C12N 15/12; C12N 15/79; C12P 21/02
[52] U.S. Cl. ..................... 435/69.1; 435/320.1; 435/325; 435/369; 536/23.5
[58] Field of Search ........................... 435/6, 320.1, 325, 435/69.1, 369; 536/23.1, 23.5

[56] References Cited

PUBLICATIONS

Database Dissabs on STN, AN 97:50427. UMI AAR9723363, Hacohen, N. et al. Branching Morphogenesis in the Drosophila Tracheal System (sprouty, branchless, cell differentiation), Diss. Abstr. Int. B. 1997, vol. 58, No. 2B, p. 517.

Database Dissabs on STN, AN 97:77511. UMI AAR9801196, Kramer, K.S. Cell Fate Determination in the Compound Eye of Drosphila Melanogaster: the Roles of Seven–up and Sprouty (vision, photoreceptor, cones), abstract, Diss. Abstr. Int. B. vol. 58, No. 7B, p. 3444.

Hacohen, N., et al., "sprouty Encodes a Novel Antagonist of FGF Signaling that Patterns Apical Branching of the Drosophila Airways," *Cell*, 92: 253–263 (1998).

Cross et al. (Mar. 1994) Purification of CpG islands using a methylated DNA binding column. Nature Genetics 6:236–244.

Hillier et al. (Jun. 2, 1995) EST # 156055. GenBank EST. Accession No. R72442. Accessed May 18, 1998.

Hillier et al. (Apr. 10, 1996) EST # 278548. GenBank EST. Accession No. N98688. Accessed May 18, 1998.

*Primary Examiner*—Robert A. Schwartzman
*Attorney, Agent, or Firm*—Foley, Hoag & Eliot, LLP; Matthew Vincent, Esq.; Diana M. Steel

[57] ABSTRACT

A new class of mammalian sprouty proteins is disclosed. The proteins are characterized by an amino acid sequence whose cysteine-rich region has at least 40% sequence identity with SEQ ID NO:17 in the human sprouty 2 protein whose full length sequence is identified by SEQ ID NO:8. Also disclosed are (i) a pharmaceutical preparation containing a sprouty protein, (ii) a DNA sequence encoding the protein, (iii) vector and gene therapy compositions containing the DNA coding sequence, and (iv) methods of detecting a condition characterized by, or risk factor associated with, abnormal levels of active mammalian sprouty protein in a mammalian subject.

16 Claims, 20 Drawing Sheets

```
   1 CCGGCGATTGCCGCGTTCGCTGTCTTTCCGATTTCCTCAAAAAGCAAGCCACTTTTTTTTCGTATAACTACACAACATTTTTTTCGAAGCAACCAAATCATTTAGCAAATCG
 108 AGCAACAATAGCCTGCTAAACAATTCACTACAGAAGACGCGCTAAACAACCCGCAGATATATATTGAAAATATATATAAAACAAGCAATCACTTGAAAAATATTG
 216 TGTGTGGTGAAAGTGAGTGTTTATTTTTGGGAAATAGAAATACAAACTCGCTTCCAATGAAATCATGTGCCTAAAAATGCAAA
 324 TTGCTCGAAGAAATACAAACGTCTATTTAAAAACAACAGTTCAACTCAAGCCACACAGAAGTTTATAGAATACAAAACGTGTTGGGAAAAGTAAAATATATTTTTTACTC
 432 ATACAGCAAATACGCACACACGCAGCAGCGCCAGCTTCGCCGCTCGCACAGATACATTCGCCGCTCGCACAACAACATATTTTTATAAATCTATAAATGTCATAAAAATTGCATAAAAATATTTTTACTT
 540 AAGACAACGACGCACACACAACAGCAGCGCCAGCTTCGCTGCTCGCACAGATACATTCGCCGCTCGCACAACAACATACCGCCGGTCGCCAAGTTGATTATTATTATTTTTTGG
 648 GTATCTGTGTGATTGTGCGACGCCAAACCAAGCGAATAAACCAGCGAAAATGCAAGCGCGGCTGGCAAAAATAAAATGCGGCTCGCCGGATCGCGAGTAAGCATCTGAAGAA
 756 CCAAAAACCAAAACCAACCAAACCAGCGAAAATGCGAAGCAAAGCGAAAATGCAAAAGAAACGAATTCATCATTTGGATACTTTTCAACTTTTCAACTTTCAACTCTACG
 864 AAATTACTTTTGTGAATCGCCTTTCCAAATCGCCTTTGCTTTGAAAAATCAATAAAGCAATTCATCATTTGGATACTTTTGAAATCTGCAGCAGTCTCGATCTCGAGTCCGGGC
 972 CCCCCCCTCCTCCCAAATCGCCCTTTGCTTTTGAAAAATCAATAAAGCAATTCATCATTTGGATACTTTTGAAATCTGCAGCAGTCTCGATCTCGAGTGTGGAGGAGTGCAGCTG
1080 GTGATTAATTACGGAATTTGTACCACGGATTGCTTTTGAAAATCAATAAAGCAATTCATCATTTGGATACTTTTGAAATCTGCAGCAGTCTCGATCTCGAGTGTGGAGGAGTGCAGCTG
1188 GCAGTAACTACGATCGACGGCATTGAGGATCTCGGATTCGAGGTGGAGGAGCGATCTCGAGGTGGAGGAGCGATTACCGCGCGTCATCGACCAAGGGCG
1296 GGGGAGGAGTCCTGGTTACACACTACATGATCGCAGAAATGCGGGCGATCCTTGGCGCCCCCGAAGTTATTACCGCGCGTCATCGACCAAGGGCG
                                                     M  D  R  R  N  G  G  D  P  L  A  P  P  R  P  P  K  L  L  P  R  V  H  R  P  R  A
1405 CCGGAGCCGACGTTAAGTGGTGTCGACCATACCGCAGGAGCCAACTGCATCCGGAGCATCAGGAGCATCTGCAGC A*A P P V A I H N N N S
  28  P  E  P  T  L  S  G  V  D  H  T  A  G  A  T  A  S  A  L  A  S  G  A  S  S  A* A  P  P  V  A  I  H  N  N  N  S
1512 CAGCAGCAACTTAGTATTAGCGCGGCGGCGAGCAACAACAATACGATATCGATAATCCGGCGAGCCCGGACTTCGACGACTACGACCAGATCCACCACCTGACCTTCCTG
  64  Q  Q  Q  L  S  I  S  A  A  A  S  N  N  N  T  I  S  I  I  P  A  S  P  D  F  D  D  Y  Q  I  H  H  L  T  F  L
1620 CCCCAGCGACCAAGCAGTCTGAGCCGGAACAGCAGTACGGCGTCATCGACTACTGGATTGGTGTCTCCGGTTCGGAGGATCGTGTTGGGGTTCGTCGTCCAGC
 100  P  Q  R  P  P  S  S  L  S  R  N  S  T  A  S  S  T  T  A  T  G  I  S  V  S  G  G  S  V  S  G  S  S  S  S
1728 TTCACGAGACGCAAGCTCTGCGACCGCCGGCACCTGTACCGCTGAACAACAGCATCAACAACAACAGCAACACTTCCTTAGTCATTTCCAAAGGCTGAG
 136  F  T  R  R  R  P  P  A  P  P  V  P  L  N  N  S  I  N  N  N  S  N  N  F  L  S  H  F  Q  S  A  E
1836 CCCGGCGAGCAACGCTCTGGGCCAGCCGCCGGCGAGTGTAACCCTGGCGCAGCCCGTCACGCCGAAGCGTAACATGAGTATGTGGACACGCCGCTGCAA
 172  P  A  S  N  A  L  G  Q  P  P  A  S  P  V  T  L  A  Q  P  R  P  E  S  E  R  L  T  N  E  Y  V  D  T  P  L  Q
1944 CATGCGACGCGCTCGCAGCATCCGGCTGGCGTGCAGGATAATGGCCAGACGACCACCCACCCTGTTGCTGCTGCCCCAGCGGAATCAGCAGCACCTGCACCTGCAACAA
 208  H  A  T  R  S  Q  H  P  A  G  Q  Q  D  N  G  Q  T  T  T  H  H  L  L  L  L  P  Q  R  N  Q  H  L  Q  Q
```

Figure 5D:
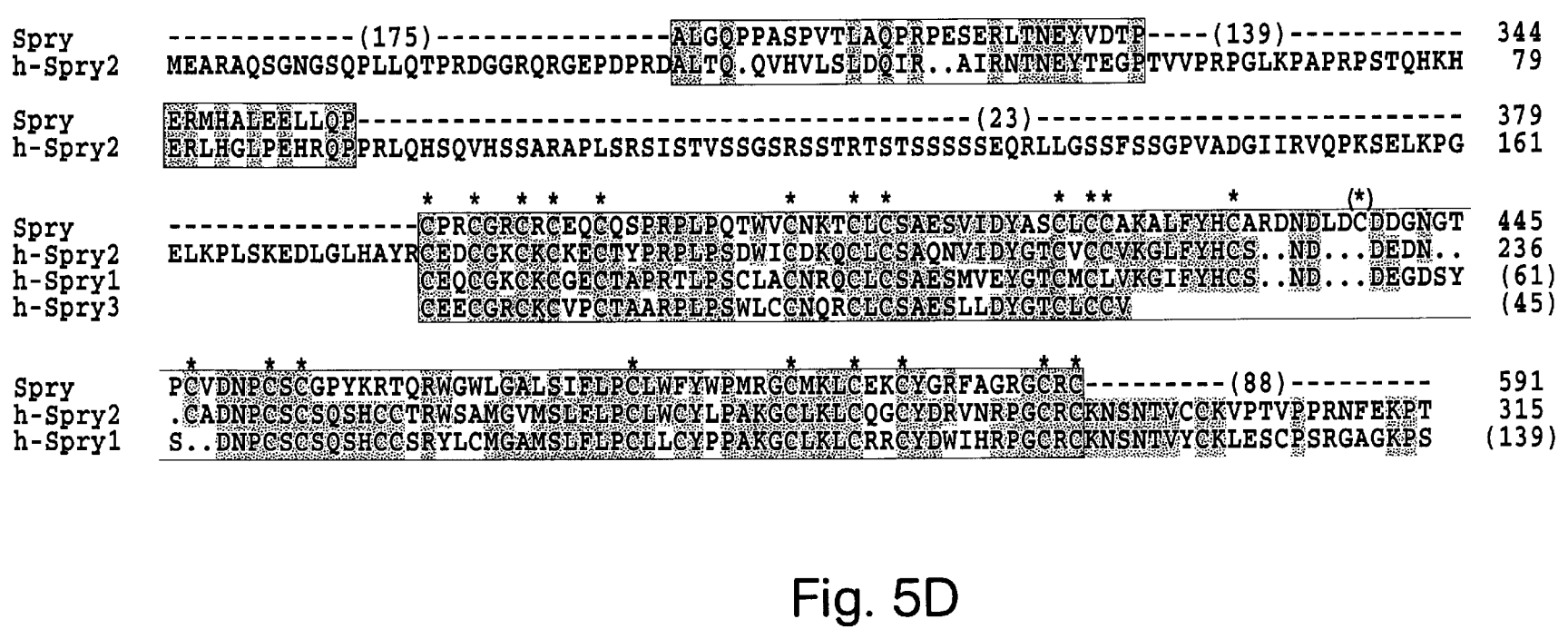

```
Spry      ----------(175)-----------------------------------ALGQPPASPVTLAQPRPESERLTNEVVDTP-----(139)-----       344
h-Spry2   MEARAQSGNGSQPLLQTPRDGGRQRGEPDPRDALTQ.QVHVLSEDQIR..AIRNTNEYTEGPTVVPRPGLKPAPRPSTQHKH        79

Spry      ERMHALEELLQP----------------------------------------------------------(23)-----------       379
h-Spry2   ERLHGLPEHRQPPRLQHSQVHSSARAPLSRSISTVSSGSRSSTRTSTSSSSEQRLLGSSFSSGPVADGIIRVQPKSELKPG         161
                    *                        *        *           *      *

Spry      ----------CPRCGRCREQCQSPRPLPQTWCNKTCLCSAESVIDYASCLCCAKALFYHCARDNDLDCDDGNGT              445
                    *     *  * * *   ** *     *    *    *      *     (*) 
h-Spry2   ELKPLSKEDLGLHAYRCEDCGKCKCKECTYPRPLPSDWICDKQCLCSAQNVIDYGTCVCVKGLFVHCS..ND...DEDN..       236
h-Spry1   CEQCGKCKCGECTAPRTLPSCLACNRQCLCSACNRQCLCSAESMVEYGTCMCLVKGIFVHCS..ND...DEGDSY            (61)
h-Spry3   CEECGRCKCVPCTAARPLPSWLCGNQRCLCSAESLLDYGTCLCCY                                           (45)

Spry      PCVDNPCSCGPYKRTQRWGWLGALSIFLPCLMFYWPMRGCMKLICEKCYGRFAGRGCRC-----(88)-----               591
                  *        *         *       *          *  
h-Spry2   .CADNPCSCSQSHCCTRWSAMGVMSLEEPCEWCKLPAKGCLKLCQGCVDRVNRPGCRCKNSNLVCCKVPTVPPRNFEKPT        315
h-Spry1   S...DNPCSCSQSHCCSSRYLCMGAMSIFLPCLLCVPPAKGCLKLCRRGYDWIHRPGCRCKNSNTVYCKLESCPSRGAGKPS      (139)
```

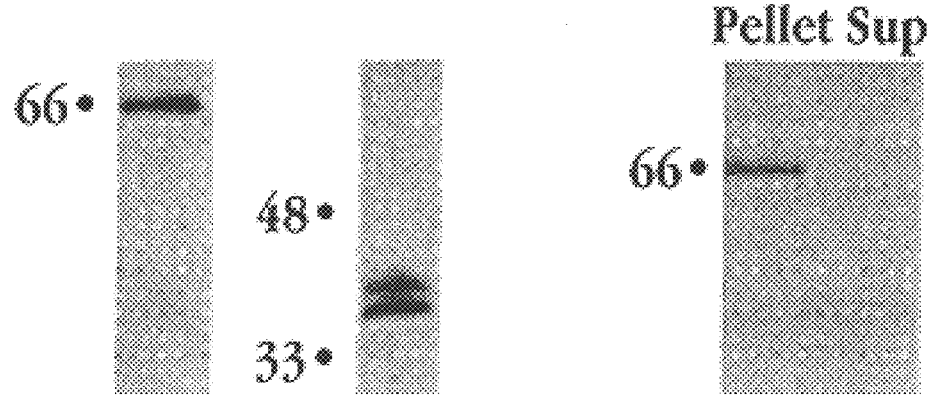

```
              10                    20                    30
h-spry2
h-spry1
h-spry3
m-spry1
m-spry4
d-spry   M D R R N G G D P L A P P R P P K L L P R V H R P R A P E P 40                    50                    60
h-spry2
h-spry1
h-spry3
m-spry1
m-spry4
d-spry   T L S G V D H T A G A T A S A L A S G A S S A A P V A I H N 70                    80                    90
h-spry2
h-spry1
h-spry3
m-spry1
m-spry4
d-spry   N N S Q Q Q L S I S A A A S N N N T I S I I P A S P D F D D 100                   110                   120
h-spry2
h-spry1
h-spry3
m-spry1
m-spry4
d-spry   Y Q I H H L T F L P Q R P S S L S R N S S T A S S T T A T G 130                   140                   150
h-spry2                                                M E A R A Q
h-spry1
h-spry3
m-spry1
m-spry4
d-spry   I S V S G S G S V S G S S S S F T R R R P P A P V P L N N S 160                   170                   180
h-spry2  S G N G S Q P L L Q T P R D G G R Q R G E P D P R D A L T Q
h-spry1
h-spry3
m-spry1
m-spry4
d-spry   I S N N N N S I N N N F L S H F Q S A E P A S N A L G Q P
```

Fig. 13A

```
                        190             200            210
h-spry2   Q V H V L S L D Q I R - - A I R N T N E Y T E G P T V V P R
h-spry1
h-spry3
m-spry1
m-spry4
d-spry    P A S P V T L A Q P R P E S E R L T N E Y V D T P L Q H A T 220             230            240
h-spry2   P G L K P A P R P S T - - - - - - - - - - - - - Q H K H E R
h-spry1
h-spry3
m-spry1
m-spry4
d-spry    R S Q H P A G Q Q D N G Q T T T H H L L L L P Q R N Q H L H 250             260            270
h-spry2   L H G L P E H R Q P P R L Q H S Q V H S S A R A P L S R S I
h-spry1
h-spry3
m-spry1
m-spry4
d-spry    L Q Q H Q Q H L Q Q Q Q Q Q Q Q Q Q Q Q Q Q H L Q H Q Q 280             290            300
h-spry2   S T V S S G S R S S T R T S T S S S S S E Q R L L G S S F S
h-spry1
h-spry3       P L P L D Q R L L A S I T P S P S G Q S I I R T Q P G
m-spry1
m-spry4
d-spry    N Q Q H A R L A T T T Q A T S V G S D H T D G L L H S H L Q 310             320            330
h-spry2   S G P V A D G I I R - - - - - - - - - - - - - - - - - - -
h-spry1
h-spry3   A G - - - - - - - - - - - - - - - - - - - - - - - - - - -
m-spry1
m-spry4
d-spry    N S T T K P P A S K Q P A L P R L G M G L G L G L G L G L N 340             350            360
h-spry2   - - - - - - - - - - - - - - - - - - - - - V Q P K S E L
h-spry1
h-spry3   - - - - - - - - - - - - - - - - - - - - - V H P K A D G
m-spry1
m-spry4
d-spry    Q P I I T K Q P T P A T Q K E R M H A L E E L L Q P G G A G
```

Fig. 13B

```
                              370                 380                 390
h-spry2   K P G E L K P L S K E D L G L H A Y R │C E│D│C G│K│C K C│K E
h-spry1                                         │C E│Q│C G│K│C K C│G E
h-spry3   A L K G E A E Q S A G H P S E H L F I │C E│E│C G│R│C K C│V P
m-spry1             A S L K E D P T Q H K F I   │C E│Q│C G│K│C K C│G E
m-spry4
d-spry    G N G G P L V M A G D P S L L N P I V │C│P R│C G│R│C│R│C│E Q 400                 410                 420
h-spry2  │C T│Y│P R│P│L P S│D W I│C│D K Q│C L C S A│Q N V I D│Y G T C
h-spry1  │C T│A│P R│T│L P S│C L A│C│N R Q│C L C S A E S│M V E│Y G T C
h-spry3  │C T│A A│R│P L P S│C W L│C│N Q R│C L C S A E S│L L D│Y G T C
m-spry1  │C T│A│P R│R M P S│C L A│C│D R Q│C L C S A E S│M V E│Y G T C
m-spry4                                 │N Q E│C L C S A│Q T L V N│Y G T C
d-spry   │C│Q S│P R│P│L P│Q T W V│C│N K T│C L C S A E S│V I D│Y│A S│C 430                 440                 450
h-spry2   V│C│C│V K G│L│F Y H C│S│N│- - - - - - - D D E D N C A│D N│
h-spry1   M│C│L│V K G│I│F Y H C│S│N│D - - - - - - D E G D S Y S│D N│
h-spry3   L│C│C│V│
m-spry1   M│C│L│V K G│I│F Y H│S S│N│D - - - - - - A D G G S Y S│D N│
m-spry4   M│C│L│V│Q│G│I│F Y H C│T│N│E - - - - - - D D E G S C A│D H│
d-spry    L│C│C│A K│A│L│F Y H C│A R D N D L D C D D G N G T P C V│D N│

460                 470                 480
h-spry2  │P C S C S│Q S H C C T│R│W S A M│G│V M│S│L F│L P C L│W C│Y│L
h-spry1  │P C S C S│Q S H C C S│R│Y L C M│G│A M S L F│L P C L│L C│Y│P
h-spry3
m-spry1  │P C S C S│Q
m-spry4  │P C S C S│G S N C C A│R│W S F M│G│A L│S│V V│L P C L│L C│Y│L
d-spry   │P C S C│G P Y K R T Q│R│W G W L│G│A L│S│I F│L P C L│W F│Y│W 490                 500                 510
h-spry2  │P│A K│G C│L│K L│C Q G C│Y│D R V N R P│G C R│K N S N - - -
h-spry1  │P│A K│G C│L│K L│X R R C│Y│D W I H R P│G C R│
h-spry3
m-spry1
m-spry4  │P│A T│G C│V│K L│A Q R G│Y│D R L R R P│G C R│K H T N - - -
d-spry   │P│M R│G C│M│K L│C E K C│Y│G R F A G R│G C R│Q G I G G G G 520                 530                 540
h-spry2   - - - - - - - - - - - - - - - - - - - - - - - - - - - -
h-spry1
h-spry3
m-spry1
m-spry4   - - - - - - - - - - - - - - - - - - - - - - - - - - - -
d-spry    A G S G G G V G S I G S T S S M L P I V P L G V N G S G L G
```

Fig. 13C

```
                          550                    560                    570
h-spry2   - - - - - - - - - - - - - - - - - - - - - - - - - - - - - - -
h-spry1
h-spry3
m-spry1
m-spry4   - - - - - - - - - - - - - - - - - - - - - - - - - - - - - - -
d-spry    G G V S L S G G V T D G G L N Q A N G K A M D H G C S A A R 580                    590                    600
h-spry2   T V C C K V P T V P P R N - - F E K P T
h-spry1
h-spry3
m-spry1
m-spry4   S V I C K A A S G D T K T S R S D K P F
d-spry    S I L R K G D L T P E K R L L D S S P D Y
```

Fig. 13D

SPROUTY PROTEIN AND CODING SEQUENCE

This application claims the benefit of U.S. Provisional Application Ser. No. 60/030,232, filed Nov. 7, 1996, incorporated herein by reference in its entirety.

This work was supported in part by NIH Grant GM 47735. Accordingly, the United States Government has certain rights in this invention.

FIELD OF THE INVENTION

The present invention relates to modulators of the FGF signalling pathway, particularly to modulators of FGF-mediated endothelial tube branching, e.g., capillary branching (angiogenesis) and tracheal branching, and methods of use thereof.

References

Ausubel, F. M., et al., *CURRENT PROTOCOLS IN MOLECULAR BIOLOGY*, John Wiley and Sons, Inc., Media, Pa. (1988).

Artavanis, T. S., et al., *Science* 268:225–232 (1995).

Beck-Sickinger, and Jung, *Biopolymers* 37:123–142 (1995).

Bellen, H., et al., *Genes Dev.* 3:1288–1300 (1989).

Betageri, G. V., et al., "Targeting of Liposomes" in *LIPOSOME DRUG DELIVERY SYSTEMS* (Technomic Publishing Co., Inc., Lancaster, Pa., pp. 89–108 (1993).

Bier, E., et al., *Genes Dev.* 3:1273–1287 (1989).

Brand, A. H., and Perrimon, N., *Development* 118:401–415 (1993).

Brunner, D., et al., *Nature* 370:386–389 (1994).

Edgar, B. A., et al., *Development* 120:3131–43 (1994).

Gabay, L., et al., *Development* 122:3355–3362 (1996).

Glazer and Shilo, *Proc. Natl. Acad. Sci.* 87:3851–3855 (1990).

Goldberg, J., et al., *Eur. J. Biochem.* 218:597–601 (1993).

Guillemin, K., et al., *Development* 122:1353–1362 (1996).

Hacohen, N., Ph.D. Thesis, Leland Stanford Junior University, Stanford, Calif. (1997).

Harlow, E., et al., *ANTIBODIES: A LABORATORY MANUAL*, Cold Spring Harbor Laboratory Press, Cold Spring Harbor, N.Y. (1988).

Klaes, A., et al., *Cell* 78:149–160 (1994).

Kramer, S., et al., *Development* 121:1361–1372 (1995).

Lai, Z.-C., and Rubin, G. M., *Cell* 70:609–620 (1992).

Lee, et al., *Nucleic Acid Research* 21:3761–3766 (1993).

Lennon, G., et al., *Genomics* 33:151–2 (1996).

Lin, D. M., and Goodman, C. S., *Neuron* 13:507–523 (1994).

Lindsley, D. L., and Zimm, G. G., *THE GENOME OF DROSOPHILA MELANOGASTER*, Academic Press, San Diego, Calif. (1992).

Lis, J. T., et al., *Cell* 39:403–410 (1983).

Lundegren, U., et al., *Science* 241:1077 (1988).

Moore, G. J., *Trends in Pharmacological Sciences* 15:124–129 (1994).

Mullis, K. B., et al., U.S. Pat. No. 4,683,195, issued Jul. 28, 1987.

Mullis, K. B., U.S. Pat. No. 4,683,202, issued Jul. 28, 1987.

Nagashima, M., et al., *J. Biol. Chem.* 268:2888–2892 (1993).

O'Neill, E. M., et al., *Cell* 78:137–147 (1994).

O'Reilly, M. S., et al., *Cell* 79:315–328 (1994).

Perrimon, N., et al., *Dev. Genet.* 12:238–52 (1991).

Rebay, I., and Rubin, G. M., *Cell* 81:857–866 (1995).

Robertson, H. M., et al., *Genetics* 118:461–470 (1988).

Saiki, R. K., et al., *Science* 230:1350 (1985).

Samakovlis, C., et al., *Development* 122:1395–1407 (1996).

Sambrook, J., et al., *MOLECULAR CLONING: A LABORATORY MANUAL*, Second Edition, Cold Spring Harbor Laboratory Press, Cold Spring Harbor, N.Y., (1989).

Scholz, H., et al., *Genetics* 135:455–468 (1993).

Sutherland, D. C., et al., *Cell* 87:1091–1101 (1996).

Tautz, D., and Pfeifle, C., *Chromosoma* 98:81–85 (1989).

White, K., et al., *Science* 264:677–683 (1994).

Whitely, N. M., et al., U.S. Pat. No. 4,883,750 (1989).

Winn-Deen, E., et al., *Clin. Chem.* 37:(1522) (1991).

Wohlwill, A. D., and Bonner, J. J., *Genetics* 128:763–775 (1991).

Wu, D. Y., et al., *Genomics* 4:560 (1989).

Xu, T., and Rubin, G. M., *Development* 117:1223–1237 (1993).

Zinn, K., et al., *Cell* 53:577–87 (1988).

BACKGROUND OF THE INVENTION

Normal capillaries are composed of endothelial cells and pericytes and serve to transport blood to all body tissues. Neovascularization, or angiogenesis, is the growth and development of new capillaries from existing vessels. Angiogenesis is essential for the initial formation of the vascular system as well as for reproduction and wound healing. There are, however, conditions characterized by unregulated persistent neovascularization, including a variety of tumor cancers, diabetic retinopathy, neovascular glaucoma, rheumatoid arthritis and psoriasis.

It is therefore desirable to understand the molecular basis of angiogenesis, as a basis for designing therapeutic strategies for treating conditions, such as cancer, characterized by unregulated, persistent neovascularization, or conditions, such as wound healing where increased vascularization is needed.

SUMMARY OF THE INVENTION

The invention includes, in one aspect, an isolated recombinant sprouty polypeptide comprising (i) a protein containing an amino acid sequence whose cysteine-rich region has at least 40% sequence identity, and preferably at least 50% sequence identity, with SEQ ID NO:17 in the human sprouty 2 protein whose full length sequence is identified by SEQ ID NO:8, or (ii) a peptide derived therefrom, and having at least 10 amino acids.

Exemplary proteins include the human sprouty 2 protein having a sequence substantially identical to SEQ ID NO:8, the human sprouty 1 protein containing a sequence substantially identical to SEQ ID NO:6, and the human sprouty 3 protein containing a sequence substantially identical to SEQ ID NO:11.

The protein may be used, for example, in treating a solid tumor in a patient, by administering to the patient an amount of the protein effective to inhibit tumor growth. In this treatment method, the protein may be encapsulated in liposomes having an average size less than about 150 nm, and a surface coating of polyethyleneglycol.

In another aspect, the invention includes an isolated DNA fragment that encodes a sprouty polypeptide comprising (i) a protein containing an amino acid sequence whose cysteine-rich region has at least 40% sequence identity, and preferably at least 50% sequence identity, with SEQ ID NO:17 in the human sprouty 2 protein whose full length sequence is identified by SEQ ID NO:8, or (ii) a peptide derived therefrom, and having at least 10 amino acids.

Exemplary sequences include those that encode (i) a human sprouty 2 protein having a sequence substantially identical to SEQ ID NO:8, such as the DNA sequence identified by SEQ ID. NO:7, (ii) a human sprouty 1 protein containing a sequence substantially identical to SEQ ID NO:6, such as the DNA sequence containing a region identified by SEQ ID. NO:5, and (iii) a human sprouty 3 protein containing a sequence substantially identical to SEQ ID NO:11, such as the DNA sequence containing a region identified by SEQ ID. NO:10.

In a related aspect, the invention includes a recombinant expression vector, comprising the DNA coding sequence above, and a regulatory sequence operable linked to the fragment and capable of promoting expression of the protein in a selected host. The vector may be complexed with a polycation to form a condensed particle having a size less than about 150 nm, for use transfecting cells, to increase secretion of the sprouty protein from the cells. The complex may further include a targeting moiety capable of binding specifically to tumor cell surfaces. Also disclosed is a mammalian cell transformed with the vector.

In still another aspect, the invention includes a method of detecting a condition characterized by, or risk factor associated with, abnormal levels of active mammalian sprouty protein in a mammalian subject. The method includes obtaining genomic DNA or cDNA from the subject, and examining the DNA or cDNA for the presence or absence of mutations relative to the human sprouty genes selected from the group consisting of genes identified by SEQ ID NO:5, SEQ ID NO:7, and SEQ ID NO:11.

The invention also includes a method of detecting a condition characterized by, or risk factor associated with, abnormal levels of active mammalian sprouty protein in a mammalian subject. The method includes obtaining fluid from a tissue or organ in the subject, reacting the fluid with an antibody against a human sprouty protein of the type described above, and to form a protein-antibody complex, and identifying the presence of such complex.

These and other objects and features of the invention will become more fully apparent when the following detailed description is read in conjunction with the accompanying drawings.

BRIEF DESCRIPTION OF THE FIGURES

FIGS. 2A, 2C, 2E and 2G show whole embryos; FIGS. 2B, 2D, 2F and 2H show close-ups.

FIGS. 3A, 3B, 3E and 3F are photomicrographs of dorsal branches; FIGS. 3C and 3D are tracings of ganglionic branches; FIGS. 3K and 3L are photomicrographs of wild type (FIG. 3K) and Spry$^{\Delta 5}$ (FIG. 3L) larval dorsal branches.

FIG. 5C shows the nucleic acid sequence (SEQ ID NO:1) and translated amino acid sequence (SEQ ID NO:2) of Drosophila Spry;

FIG. 5D shows an alignment of polypeptides derived from the following Spry sequences: Drosophila Spry (amino acids 175 to 205, 345 to 356, and 308 to 503 of SEQ ID NO:2); h-Spry2 (SEQ ID NO:8); h-Spry1 (amino acids 5 to 139 of SEQ ID NO:20); and h-Spry3 (amino acids 56 to 100 of SEQ ID NO:11);

FIGS. 9A–P are photomicrographs illustrating the effects of Spry mutations on the Bn1 pathway in Drosophila embryos as detailed in Example 9. FIGS. 9A–E show the effects of Spry mutations on expression of Spry and pnt; FIGS. 9F–9K show the effects of Spry mutatations on expression of DSRF; FIGS. 9L–N show the effects of Spry mutations on expression of Yan; and FIGS. 9O and 9P indicate the effect of elevated levels of Spry;

FIG. 10A is a schematic representation of DB development in wild type cells expressing Bn-1; FIGS. 10B–F illustrate the effect of Bn1 pathway mutants on Spry expression in the developing DB, visualized by immunostaining of the Spry9143 marker;

FIGS. 12A–C present Western blot results corresponding to expression of Spry proteins, drosophila Spry and human Spry2, in cell culture (Example 11), where FIG. 12A corresponds to 66 kD Drosophila Spry; FIG. 12B shows hSpry2 protein at 35–40 kD; and FIG. 12C corresponds to the 100 K rpm pellet and supernatant of homogenized cells expressing Drosophila Spry.

FIGS. 13A–D show an alignment of the following Spry sequences: full length h-Spry2 (SEQ ID NO:8), h-Spry1 cysteine rich region (SEQ ID NO:6), h-Spry3 cysteine rich region (SEQ ID NO:11), m-Spry1 cysteine rich region (SEQ ID NO:13), m-Spry4 cysteine rich region (SEQ ID NO:16), and full-length d-Spry (SEQ ID NO:2);

DETAILED DESCRIPTION OF THE INVENTION

I. Definitions

Figure 1A:
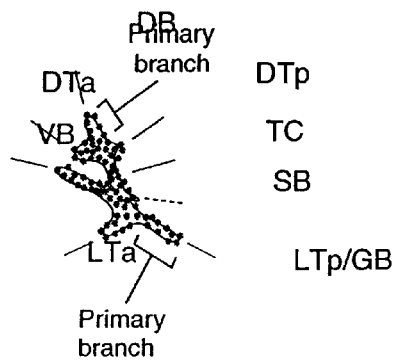
FIGS. 1A, 1B and 1C are schematic diagrams of unicellular branches in the developing Drosophila tracheal system. The fifth tracheal unit is shown at stage 12 (FIG. 1A), stage 16 (FIG. 1B), and third instar larval (FIG. 1C).

A polypeptide sequence or fragment is "derived" from another polypeptide sequence or fragment when it has the same sequence of amino acid residues as the corresponding region of the fragment from which it is derived.

A polynucleotide sequence or fragment is "derived" from another polynucleotide sequence or fragment when it has the same sequence of nucleic acid residues as the corresponding region of the fragment from which it is derived.

A first polynucleotide fragment is "selectively-hybridizable" to a second polynucleotide fragment if the first fragment or its complement can form a double-stranded polynucleotide hybrid with the second fragment under selective hybridization conditions. The first and second fragments are typically at least 15 nucleotides in length, preferably at least 18–20 nucleotides in length. Selective hybridization conditions are defined herein as hybridization at ~45° C. in ~1.1 M salt followed by at least one wash at 37° C. in 0.3 M salt.

Two or more polynucleotide or polypeptide fragments have at least a given percent "sequence identity" if their nucleotide bases or amino acid residues are identical, respectively, in at least the specified percent of total base or residue position, when the two or more fragments are aligned such that they correspond to one another.

"Substantially purified" refers to the at least partial purification of a polynucleotide, polypeptide, or related compound (e.g., anti-Spry antibodies) away from unrelated or contaminating components (e.g., serum cells, proteins, and non-anti-Spry antibodies). Methods and procedures for the isolation or purification of compounds or components of interest are described below (e.g., affinity purification of fusion proteins and recombinant production of Spry polypeptides).

The term "Spry polynucleotide" refers to (i) an isolated DNA fragment that encodes a sprouty polypeptide comprising (a) a protein containing an amino acid sequence whose cysteine-rich region has at least 40% sequence identity, and preferably at least 50% sequence identity, with SEQ ID NO:17 in the human sprouty 2 protein whose full length sequence is identified by SEQ ID NO:8, or (b) a peptide derived therefrom and having at least 10 amino acids. In the alternative, the term refers to a polynucleotide containing a region of at least 30, preferably at least 100 nucleotides in length that is selectively-hybridizable with the sequence presented herein as SEQ ID NO:1, SEQ ID NO:5, SEQ ID NO:7 or the complement of one of the sequences.

A "Spry polynucleotide" refers to a polypeptide comprising (a) a protein containing an amino acid sequence whose cysteine-rich region has at least 40% sequence identity, and preferably at least 50% sequence identity, with SEQ ID NO:17 in the human sprouty 2 protein whose full length sequence is identified by SEQ ID NO:8, or (b) a peptide derived therefrom and having at least 10 amino acids.

II. Identification of Sprouty Alleles Causing Excessive Tracheal Branching

Mutagenesis studies, detailed in Example 1, were performed to identify the gene responsible for the expression pattern of the Pantip-2 tracheal marker. The Pantip-2 tracheal marker is a P[lacZ] insert at 63D1,2 in which the beta-galactosidase marker protein is expressed in tracheal cells as they form branches (Samakovlis, et al., 1996). The original insert (2683) was homozygous viable and showed a normal tracheal branching pattern. One hundred P-element excision alleles were generated by introduction of transposase and scored for lethality and embryonic tracheal phenotypes. Of the twelve lethal excision alleles recovered, three (sprouty$^{\Delta 5}$, sprouty$^{\Delta 64}$, and sprouty$^{\Delta 55}$) showed extra tracheal branches as described below and represented a single complementation group.

As detailed in Example 2, Spry$^{\Delta 5}$/Spry$^{\Delta 5}$ embryos had 1.5 to 2 times as many fine branches as normal emanating from most primary branches (dorsal branch, lateral trunk anterior and lateral trunk posterior and ganglionic branch) at embryonic stage 16 and ~30% more branches than normal emanating from the visceral branch (FIG. 2, Table 1). The extra tracheal branches arose in many positions throughout the tracheal network (FIG. 2C, G) but were not distributed randomly. Rather, the extra branches were clustered around the sites where secondary and terminal branches normally form (FIG. 2B, H). The primary branching pattern was not affected in Spry mutants: all primary branches grew to their normal lengths and reached their destinations at the appropriate times in development. The other excision alleles (Spry$^{\Delta 64}$, Spry$^{\Delta 55}$) showed a similar phenotype, although Spry$^{\Delta 55}$ was weaker than the others.

Five EMS-induced Spry alleles (Spry$^{254}$, Spry$^{211}$, Spry$^{226}$, Spry$^{G5,}$ Spry$^{F7}$), recovered in an unrelated screen for mutations that suppress a dominant eye phenotype (Kramer, et al., 1995), mapped to the same genetic interval in the 63D region and had the same tracheal phenotype as Spry$^{\Delta 5}$ (Table 1). Spry$^{254}$ was tested and failed to complement the three original Spry alleles for tracheal function and lethality. Molecular analysis of all the EMS mutants identified lesions in Spry coding sequences.

All eight Spry mutations resulted in pupal lethality in trans to deficiencies in the 63D region including Df(3L) 1226, Df(3L) 1227, Df(3L) Hr119, Df(3L) Hr232. Spry$^{\Delta 5}$ homozygotes displayed as severe a tracheal phenotype as Spry$^{\Delta 5}$/Df(3L) 1226 and Spry$^{\Delta 5}$/Df (3L) Hr298, indicating that Spry$^{\Delta 5}$ is a strong loss-of-function or null allele (Table 1).

A genetic mosaic analysis of Spry in the developing tracheal system was carried out as described in Example 4, below, to determine in which cells the Spry gene functions to inhibit branching. Homozygous Spry$^{\Delta 5}$ mutant clones were generated in Spry$^{\Delta 5}$/+ animals using FLP-mediated mitotic recombination (Xu and Rubin, 1993) between the Spry$^{\Delta 5}$ chromosome and a Spry$^{+}$ chromosome that also carried a general tracheal lacZ marker. The Spry$^{\Delta 5}$/Spry$^{\Delta 5}$ mutant tracheal cells were identified by the absence of expression of the lacZ marker.

Figure 5A:
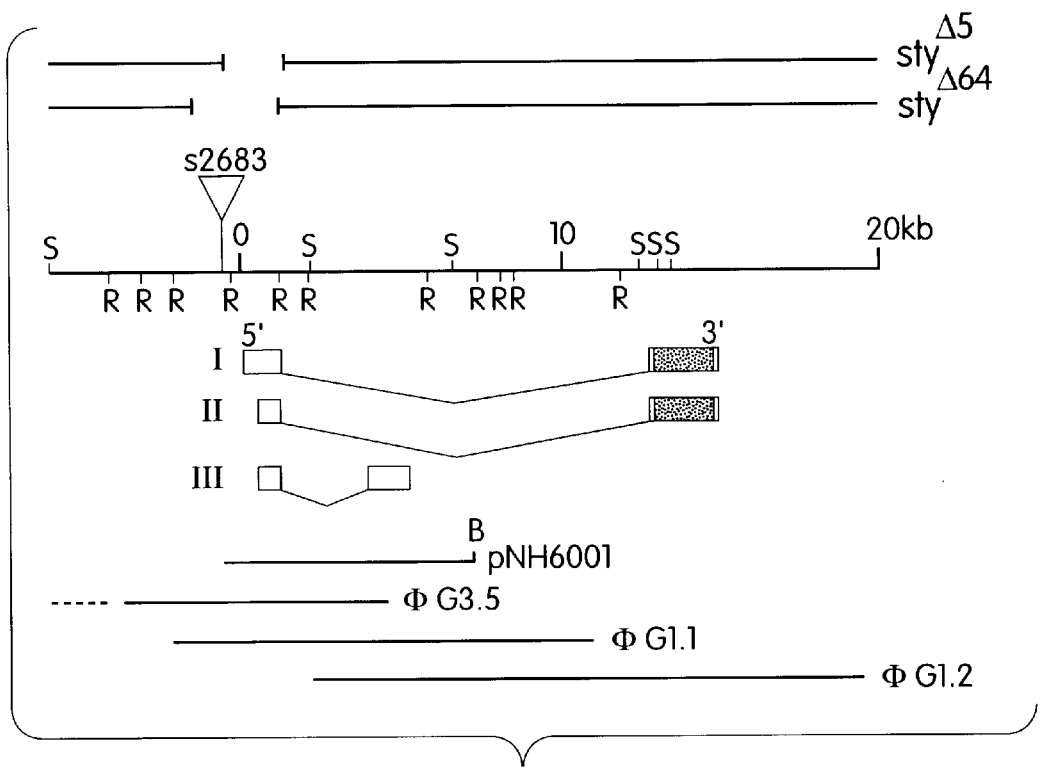
FIG. 5A shows the Drosophila Spry genomic locus.

Drosophila Spry (Dro Spry) cDNA was cloned as described in Example 5. The genomic structure, expression pattern and cDNA and amino acid sequences of Dro Spry are shown in FIGS. 5A–5D. FIG. 5A shows a diagram of the Dro Spry genomic locus and gene structure. Three classes of cDNAs were isolated and mapped onto the genomic contig of the region by the use of genomic Southerns, PCR and DNA sequencing. Exons are indicated by boxes; a filled-in box is an open reading frame; an unfilled box is an untranslated region.

An 8 kb HindIII/BamHI genomic fragment was used to screen an embryonic Drosophila cDNA library. Eleven cDNA clones, falling into three size classes, were isolated. The assignment of classes was verified by cross-hybridization and restriction enzyme analyses as well as sequencing. Exons were mapped by hybridization of cDNA fragments to digested genomic phage DNA. Intron/exon boundaries were determined by PCR analysis of genomic DNA using primers from the cDNAs and by sequencing the relevant regions of genomic DNA.

FIG. 5C shows the polynucleotide (SEQ ID NO:1) and translated amino acid (SEQ ID NO:2) sequences of cDNA clone 12.2. Analysis of the protein sequence suggests that the Spry protein is a 63 kD membrane-bound or secreted protein containing a novel 124 residue cysteine-rich region (SEQ ID NO:4). The 124 residue region is encoded by the sequence presented herein as SEQ ID NO:3.

III. Properties of the Spry Protein

A. Spry Encodes a Lateral Inhibitory Signal

Lateral inhibition is a process by which a single cell within an equipotent group of cells that is singled out to adopt a particular fate inhibits its neighbors from adopting that same fate (Artavanis, et al., 1995). In the absence of lateral inhibition, either by ablating the selected cell or by inactivating components of the lateral signaling pathway, other cells within the equivalence group adopt the same fate.

Figure 2A:
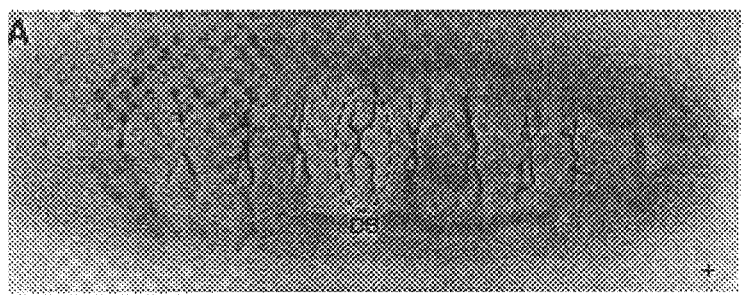
FIGS. 2A–2H are photomicrographs showing ectopic dorsal (DB) and ganglionic (GB) branches in wild type (+) and Spry$^{\Delta 5}$ mutant embryos.

Data presented herein support the function of sprouty as a lateral inhibitory signal during epithelial tube branching. As shown in FIGS. 2A–H, extra tracheal branches arising around the normal sites of branching develop in Spry loss-of-function mutants. The extra branches are indistinguishable by morphology or marker expression (FIGS. 3A–3L) from the normal branches and arise by conversion of non-branching cells to the branching fate. Further, Spry is expressed in the branch-forming cells, and genetic mosaic analysis shows that the gene is required in these cells and acts non-autonomously to inhibit neighboring cells from branching (FIGS. 4A–4C). Finally, the Spry gene encodes a protein with a putative signal peptide and a long cysteine-rich domain (FIG. 5C), and immunolocalization studies detected the protein in vesicles and at the plasma membrane (FIGS. 6A–6C), indicating that Spry is a secreted or membrane-associated protein.

These data demonstrate that Spry protein is the lateral inhibitory signal or an essential component of it. The role of Spry in inhibition of branching outside the tracheal system is supported by data showing that Spry is expressed in several developing Drosophila tissues in addition to the tracheal system and appears to function in inhibitory signaling pathways in at least some of these tissues.

In Spry mutant embryos, extra tracheal branches sprout near the normal sites of branching. Cells that give rise to the ectopic branches are indistinguishable from normal branch-forming cells and arise by the transformation of normally non-branching cells to the branch-forming fate. Analysis of mosaic clones showed that Spry is required in the normal branch-forming cells to inhibit branch formation by surrounding cells. Spry encodes a novel membrane-associated or secreted protein, containing a 124 residue cysteine-rich domain, that inhibits the switch to the branching cell fate and helps restrict fine branching to the proper positions within the tracheal epithelium.

B. Spry Limits the Range of Bn1 Signalling

Further experiments carried out in support of the gene family described herein show that Spry encodes an inhibitor that limits the range of Bn1 signaling in Drosophila, to thereby restrict secondary budding to apical positions closest to the FGF signaling centers (Examples 9 and 10).

The branchless gene (bn1) encodes a fibroblast growth factor (FGF) homolog that plays a key role in branching events (Sutherland, et al., 1996). Bn1 is required for branching and is expressed dynamically in discrete clusters of cells surrounding the tracheal sacs, at a position where a new branch will bud. The secreted growth factor activates the breathless FGF receptor (Bt1), a receptor tyrosine kinase (RTK) expressed on all tracheal cells (Glazer and Shilo, 1991; Lee et al., 1996), and guides tracheal cell migrations during primary branch formation. Bn1 also has a secondary role in branch patterning: it induces the later programs of branching in cells near the ends of the growing primary branches and in this way contributes to the apical bias in secondary branching. This function appears to be transduced by a typical RTK signaling cascade (Lee et al., 1996; Sutherland et al., 1996; Hacohen, 1997) that culminates in the MAPK-dependent degradation of Yan, an ETS domain transcription factor (Lai and Rubin, 1992) and the induction of the downstream effector genes pointed, another ETS domain transcription factor and blistered/pruned, which encodes DSRF, the Drosophila homolog of mammalian Serum Response Factor (Guillemin, et al., 1996).

To determine whether Spry+ functions by limiting the Bn1 pathway or whether it prevents branching in some other way, the effect of Spry mutations on downstream effectors (pnt, Yan, DSRF gene) in the Bn1 pathway was examined (Example 9). In Spry mutants, all five downstream effectors examined (pnt, Yan, DSRF, Terminal −2, −3, −4) were expressed in an expanded domain that included the pre-stalk chalk cells that later formed ectopic branches (FIGS. 9B, E, G, and I). The DSRF marker was activated at the same time as in the normal branching cells (FIGS. 9J, K). In Spry mutants, Yan was degraded in an expanded domain that coincided with the expanded domains of pnt and DSRF expression (FIGS. 9L, M).

These findings demonstrate that Spry loss of function mutations lead to enhancement of all of the known downstream effectors in this Bn1 pathway. Moreover, an engineered gain of function condition in which the Spry gene product was overexpressed during embryonic stages 10–12 severely blocked the normal induction of downstream effectors and branching by Bn1 (FIGS. 9O,P). These results reveal that Spry functions genetically as a competitive antagonist of the Bn1 pathway.

Additional experiments carried out in support of the invention indicate that Spry expression is induced by the Bn1 signaling pathway (Example 10).

IV. Spry Polypeptides

FIG. 13 shows the alignment of aligned amino acid sequences for full-scale Drosophila Spry and hSpry2 (human Spry2) protein, and partial sequences for hSpry1, hSpry3, mSpry1 (mouse Spry1) and mSrpy4 proteins. The region of particular interest in this figure is the region between residue number 380 and 424, where the amino acid residue numbers refer to amino acid residue numbers for the Drosophilia protein. This region is also referred to herein as the most cysteine-rich region of Spry proteins, to distinguish it from the larger cysteine-rich region defined by regions 380–503 in the figure. In the three human Spry proteins in the figure (top three lines), the 45 amino acid sequences in the most cysteine-rich region are identified for the hSpry2, hSpry1, and hSpry3 by SEQ ID NOs: 17, 18, and 19, respectively. The three regions have 25/45 sequence identity, i.e., about 55% sequence identity.

More generally, a Spry polypeptide as defined herein is a protein containing an amino acid sequence whose cysteine-rich region has at least 40% sequence identity, and preferably at least 50% sequence identity, with SEQ ID NO:17 in the human sprouty 2 protein whose full length sequence is identified by SEQ ID NO:8. Spry polypeptides also encompass peptides derived from the Spry proteins and having a sequence of at least 10 amino acids. That is, the peptide contains 10 amino acids that match a 10 mer sequence in a Spry protein, as defined above. Preferably, the peptide contains at least 15, preferably at least 20 contiguous amino acids from a Spry protein.

Spry polypeptides may be produced recombinantly or synthetically. An example of recombinant production is described in the Materials and Methods, where a pGEX-derived plasmid (pGEX-4T-2, obtained from Pharmacia Biotech, Piscataway, N.J.) was used to express Spry polypeptides for the generation of antibodies. The pGEX plasmid (Smith, et al., 1988) and its derivatives express the polypeptide sequences of a cloned insert fused in-frame with glutathione-S-transferase. Recombinant pGEX plasmids can be transformed into appropriate strains of *E. coli* and fusion protein production can be induced by the addition of IPTG (isopropyl-thio galactopyranoside). Solubilized recombinant fusion protein can then be purified from cell lysates of the induced cultures using glutathione agarose affinity chromatography according to standard methods (Ausubel, et al., 1988).

Affinity chromatography may also be employed for isolating β-galactosidase fusion proteins (such as those produced by lambda gt11 clones). The fused protein is isolated by passing cell lysis material over a solid support having surface-bound anti-β-galactosidase antibody.

Expression of drosophila Spry and human Spry2 under the control of a mammalian EF-1α promoter in human 293 cells is described in Example 11.

Isolated recombinant polypeptides produced as described above may be purified by standard protein purification procedures. These procedures may include differential precipitation, molecular sieve chromatography, ion-exchange chromatography, isoelectric focusing, gel electrophoresis and affinity chromatography.

In addition to recombinant methods, Spry proteins or polypeptides can be isolated from selected cells by affinity-based methods, such as by using anti-Spry antibodies (described below). Further, Spry peptides may be chemically synthesized using methods known to these skilled in the art.

Polypeptides of the present invention may be used in a number of ways, including the generation of antibodies. The polypeptides may be used in unmodified form, or they may be coupled to appropriate carrier molecules, such as bovine serum albumin (BSA) or Keyhole Lympet Hemocyanin (KLH) (available from, for example, Pierce, Rockford, Ill.).

V. Spry Polynucleotides

A Spry polynucleotide as defined herein is a polynucleotide coding for a Spry protein as defined above, meaning an amino acid sequence whose cysteine-rich region has at least 40% sequence identity, and preferably at least 50% sequence identity, with SEQ ID NO:17 in the human sprouty 2 protein whose full length sequence is identified by SEQ ID NO:8, or a peptide derived from a Spry protein and having a sequence of at least 10, and preferably at least 15–20 amino acids. That is, the peptide contains 10 amino acids that match a 10 mer sequence in a Spry protein, as defined above.

An NCBI BLAST search of the combined databases did not detect any closely related proteins. However, a search of the expressed sequence tag (dbEST) database identified three human homologs referred to herein as hSpry1 (SEQ ID NOs:5, 6) (clone 142025, IMAGE consortium clones, Lennon, et al., 1996), hSpry2 (SEQ ID NOs:7,8,9) (clone 40262), and hSpry3 (SEQ ID NOs:10,11; clone XAP128). A complete coding sequence was determined for hSpry2 (40262) (SEQ ID NO:7) and a partial sequence was determined for hSpry1 from overlapping cDNAs (142025, 78383 and 727987), (SEQ ID NO:5).

The hSpry2 sequence predicts a 315 residue polypeptide with a mass of 35 kD. It contains a cysteine-rich domain which is highly conserved with Spry (51% identity with 21 of the 22 Spry cysteines conserved) and two additional short stretches of similarity with Spry in the N-terminal region. hSpry1 and hSpry3 also show strong conservation of the cysteine-rich domain, with 51–70% identity to other family members in the available sequences.

Additional mouse ESTs found to be part of the sprouty gene family included mSpry1, SEQ ID NOs:12,13 (907842), mSpry2, SEQ ID NO:14 (819774) and mSpry4, SEQ ID NOs:15,16 (919795).

An alignment of the full hSpry2 sequence and partial sequences of hSpry1 and hSpry3 with the Drosophila Spry sequence is shown in FIG. 5D.

Referring now to FIG. 5D, identities are highlighted in grey and dots represent gaps inserted to maximize alignment. Numbers in parentheses indicate the number of Spry residues not shown. The cysteine-rich domain and two short regions of homology with Spry are boxed. In the cysteine-rich domain, hSpry1 is 51% (56 of 109 residues), hSpry2 is 51% (64 of 124 residues), and hSpry3 is 60% (27 of 45 residues) identical to Spry, and ~57–70% identical to each other. The asterisks show the cysteines in Spry and (*) shows the one cysteine not conserved in hSpry2. These results suggest a novel conserved cysteine-rich domain plays a major functional role in the protein.

Full-length clones of hSpry1 and hSpry2 may be isolated by one of skill in the art using guidance herein (in particular, the sequence information) in combination with known molecular biology techniques. For example, overlapping clones can be obtained by employing one of the human clones (e.g., hSpry1A clone (SEQ ID NO:5) or hSpry2A clone (SEQ ID NO:7)) or fragments thereof as probes in screening random-primed or oligo (dT)-primed human cDNA libraries generated from stage-appropriate (e.g., embryonic) endothelial cells. Such libraries are available, e.g., from Clontech (Palo Alto, Calif.). Positive clones are isolated, sequenced, and new sequence information is used for generating probes for additional rounds of screening.

Fragments from the appropriate region of a clone can be generated using, for example, polymerase chain reaction or cleavage with restriction endonucleases. These fragments can be used as radiolabelled probes in screens of libraries generated, for example, in lambda gt10. In particular, the 5' and 3' terminal sequences of the clone inserts are useful as probes to identify additional, overlapping clones.

If a full length cDNA is not isolated from a library, overlapping clones can be spliced together to generate a full length insert using well-known techniques (Ausubel, et al., 1988; Sambrook, et al., 1989). For example, the full length sequence is analyzed with a sequence analysis program, such as "MACVECTOR" (IBI, New Haven, Conn.), for unique endonuclease restriction sites in regions of overlap between two inserts.

The clones are digested with endonuclease(s) to isolate the insert from the vector, and an endonuclease that cuts in the overlap region. The digested inserts are isolated on a preparative gel, purified, and ligated to form an insert spanning the range of the two source inserts.

VI. Diagnostic Applications

The Spry proteins and coding sequences have utility in detecting (i) the presence or absence of mutations in a Spry gene, and (ii) the level of Spry proteins present in a given tissue or organ, including a solid tumor present as a primary or secondary tumor in a given tissue or organ.

A. Presence or Absence of a Spry Gene Mutation

It is of interest to detect mutations within one or more Spry genes to determine (i) an individual's genetic predisposition to pathogenic conditions, such as cancer, affected by branching mechanisms, or (ii) the possible role of a defected Spry gene in an existing condition, such as cancer, as a basis for therapy. In the former, case, somatic cells from any convenient tissue source, e.g., blood cells, may be employed as the source of genomic DNA. In the latter case, cDNA is preferably obtained from pathogenic cells, e.g., tumor cells, to allow for evaluation of the level of Spry gene transcript as well as presence or absence of a mutation in the coding region of the gene. Methods of obtaining genomic DNA and cDNA are well known (see, for example, Sambrook, et al., 1989)

The presence or absence of mutations can be determined by one of a variety of available techniques. In one method, genomic DNA or cDNA is amplified by PCR, using selected primers from the known coding sequences (Mullis, 1987; Mullis, et al., 1987; Saiki). Typically, the primers are selected to amplify the full-length coding sequence, or as large a fragment of coding sequence as is known. The amplified fragments are then fractionated and sequenced by standard methods, such as dideoxy termination sequencing or sequencing by hybridization.

Alternatively, Southern blotting for identifying fragments in a restriction-enzyme DNA digest which contain a given probe sequence, and for analyzing restriction-fragment length polymorphisms (RFLPs). This technique can detect point mutations at restriction cutting sites, and deletion, addition or rearrangement mutations with a RFLP band.

It will be appreciated that as mutations present in the population as a whole become known and catalogued, methods for quickly detecting one of a number of known mutations can be employed. For example, as many as 200 different mutations have been associated with cystic fibrosis. Methods of identifying known target sequences by probe ligation methods have been reported (Wu, et al., 1989; Whitely, et al., 1989; Lundegren, et al., 1988; Winn-Deen, et al., 1991). In one approach, known as oligonucleotide ligation assay (OLA), two probes or probe elements which span a target region of interest are hybridized with the target region. Where the probe elements match (basepair with) adjacent target bases at the confronting ends of the probe elements, the two elements can be joined by ligation, e.g., by treatment with ligase. The ligated probe element is then assayed, evidencing the presence of the target sequence.

In a modification of this approach, the ligated probe elements act as a template for a pair of complementary probe elements. With continued cycles of denaturation, reannealing and ligation in the presence of the two complementary pairs of probe elements, the target sequence is amplified geometrically, allowing very small amounts of target sequence to be detected and/or amplified. This approach is also referred to as Ligase Chain Reaction (LCR).

The level of Spry gene transcript in a given tissue, e.g., may be determined, for example, by quantitative PCR methods, in which a mixture of test cDNA and a mixture of normal (control) DNA are amplified in parallel, and then compared for relative amounts, e.g., by fractionation on a gel and quantitation of radiolabeled DNA in amplified and control and test labeled DNA.

B. Measuring Levels of Spry Protein

Measuring the presence or absence of Spry protein, or the level of Spry protein in a given sample, e.g., a tumor sample, is useful in determining whether a given condition, e.g., a pathogenic condition such as cancer, is due to abnormal levels of a Spry protein or to inactive form of the protein. The Spry protein is typically measured in the extracellular fluid of the tissue or organ of interest, e.g., a solid tumor.

Detection of Spry protein levels is preferably carried out by mixing the test sample with an antibody specific against a selected Spry protein. As described in the Materials and Methods, antibodies may be prepared by immunizing a host animal, such as a rabbit, with the purified polypeptide or fusion protein (generated using, for example glutathione-S-transferase as described above). The host serum or plasma is collected following an appropriate time interval, and the serum is tested for antibodies specific against the polypeptide.

The gamma globulin fraction or the IgG antibodies of immunized animals can be obtained, for example, by use of saturated ammonium sulfate precipitation or DEAE Sephadex chromatography, affinity chromatography, or other techniques known to those skilled in the art for producing polyclonal antibodies.

Alternatively, purified antigenic polypeptide or fused antigen protein may be used for producing monoclonal antibodies. In this case, the spleen or lymphocytes from an immunized animal are removed and immortalized or used to prepare hybridomas by methods known to those skilled in the art (see, e.g., Harlow, et al., 1988). Antibodies secreted by the immortalized cells are screened (see, e.g., using enzyme linked immunesorbent assay (ELISA) or a Western blot) to determine the clones that secrete antibodies of the desired specificity (see, e.g., Ausubel, et al., 1988).

The fluid sample is reacted with the antibody, to form a protein/antibody complex, and the mixture is then assayed for the presence/amount of complex. A variety of immunoassay formats suitable for this assay are known.

It may also be desirable to assay the specific activity of the isolated protein. This can be done, for example, by treating the test sample to remove interfering substances, e.g., FGF, and assaying the Spry protein activity of the purified or partially purified sample or Spry protein activity, e.g., as described above.

The results of the assay, assuming the test shows a lack of active Spry protein, either because the protein is produced at low levels or produced in an active form, are used to design a therapeutic strategy for supplementing or increasing the level of one or more Spry proteins, in accordance with the methods described below.

VII. Therapeutic Applications

It is known that unrestricted growth of tumors is dependent upon angiogenesis, and that induction of angiogenesis by liberation of angiogenic factors or loss anti-angiogenic factors can be an important step in tumorogenesis. The demonstration that certain animal tumors regress when angiogenesis is inhibited has provided compelling evidence for the role of angiogenesis in tumor growth (O'Reilly, et al., 1994).

A. Spry Protein Therapy

In one therapeutic application, the invention includes a method for inhibiting epithelial tube branching, e.g., angiogenesis, by administering a Spry peptide or polypeptide. In the method, pharmaceutically-effective dose of a the Spry peptide (e.g., a peptide having the sequence represented as SEQ ID NO:2, SEQ ID NO:4, SEQ ID NO:6 or SEQ ID NO:8) is delivered to the cells of a patient in need of treatment (e.g., tumor cells). In particular, methods of the invention may be used in the treatment of human patients having growing solid tumors with associated neovascularization or angiogenesis.

Types of cancer suitable for treatment using methods and compositions of the invention include solid tumor cancers such as lung cancer, colon-rectum cancer, breast cancer, urinary tract cancer, cervical cancer, biliary tract cancer, brain cancer, choriocarcinoma, endometrial cancer, esophageal cancer, gastric cancer, intraepithelial neoplasms, liver cancer, lymphomas, neuroblastomas, oral cancer, ovarian cancer, pancreas cancer, rectal cancer, sarcomas, skin cancer, testicular cancer, thyroid cancer, and renal cancer. Other disease states amenable to this treatment include, for example, diabetic retinopathy caused by vascular proliferation in the retina.

According to this method, a sprouty polypeptide or fragment thereof ("stypep") is administered to the patient, preferably at site of the patient's tumor, in an amount sufficient to inhibit neovascularization, as evidenced, for example by inhibition of tumor growth.

The Spry protein may be administered by any of a variety of methods known in the art, including oral, nasal insufflation, intraocular, parenteral, and anal and/or vaginal suppository administrations. Further, the stypep may be administered in a manner such that it arrives at the target site via the bloodstream extravascularly. Extravascular administration may be achieved by directly injecting or implanting the therapeutic peptide into the tumor using known techniques. For example, the peptide can be combined with slow release polymers such as poly-2-hydroxyethylmethacrylate or methylenevinylacetate copolymer. For skin tumors, the peptide can be combined with a topical ointment and applied directly to the surface of the tumor. Other procedures which may be useful include the preparation of the peptide in aerosol form for application to lung tumors, using standard devices employed by respiratory therapists to deliver aerosols.

When a solid tumor is surgically removed, an implant may be placed at the site of the removed tumor, to inhibit angiogenesis of any reforming tumor at the same site.

The required dose for lessening enlargement of a tumor will vary with the size and location of the tumor. Amounts may rang from 1 microgram ($\mu$g) to 1 milligram (mg). It is believed that preferred amounts will usually range from 100 $\mu$g to 800 $\mu$g quantities per dose. In general, an amount will be applied to the site of the tumor sufficient to retard growth of the tumor. The amount required for this purpose can be monitored by standard procedures. Where the tumor is still growing despite the application of the inhibitor, additional quantities will be administered. Preferably, a sufficient dose is utilized to substantially stop the increase of tumor size, or in some cases to decrease the size of the tumor. Such a result can be observed by a number of methods, depending on the location and type of tumor involved. These methods include: visual observation of surface tumors, palpitation, radiological measurement (using, e.g., X-rays for lung tumors, mammograms for breast tumors, etc.), use of ultrasound with computer assisted tomographic scanners (CAT scans), magnetic resonance imaging, radionucleotide scanning, and other standard clinical techniques used to monitor particular tumor types.

In addition to solid tumors, the inhibitors of this invention may be used as therapeutic agents for other diseases involving angiogenic dysfunction. These diseases include diabetic retinopathy, retrolental fibroplasia, neovascular glaucoma, psoriasis, angiofibromas, immune and non-immune inflammation (including rheumatoid arthritis), capillary proliferation within atherosclerotic plaques, hemangiomas, Kaposi's Sarcoma, endometriosis, and unwanted scar formation in wound healing. The amount to be used should be sufficient to partially or completely prevent the angiogenesis at the site where it is occurring.

Several methods known in the art may be used to deliver such peptides or polypeptides. An exemplary delivery method employs liposomes (e.g, fusogenic liposomes) loaded with the selected peptide using standard known methods. The liposomes may further be constructed to contain a targeting moiety or ligand, such as an antigen, an antibody, or a virus on their surface to facilitate delivery to the appropriate tissue, such as a tumor. Methods for such targeting are known (see, e.g., Betageri, et al., 1993). The liposomes are delivered to the tissue by methods known in the art, for example, direct injection. Preferred liposomes have an average size of less than about 150 nm, to allow extravasation through capillary beds in tumor regions, and a surface coating of a hydrophilic polymer, such as polyethyleneglycol (PEG) effective to extend the circulation halflife of the liposomes sufficiently to allow liposome migration to and into the tumor site.

In typical applications, the therapeutic compound is delivered to the target cells at regular intervals for the duration of treatment, which is determined by the attending physician. For example, a therapeutic peptide may be delivered once to several times daily in bolus injections containing between about 1 and about 100 $\mu$g peptide. If the peptide is contained in an encapsulant (e.g., liposomes), the amount of the suspension delivered is adjusted so that the selected pharmaceutically-effective amount of peptide is delivered.

B. Gene Therapy

The invention also includes gene therapy methods and compositions suitable for inhibiting epithelial tube branching, e.g., in angiogenesis. In this aspect, a DNA sequence encoding a Spry polypeptide (e.g., peptide SEQ ID NO:6 or SEQ ID NO:8) is cloned into an expression vector suitable for expressing the coding sequence in a tissue where inhibition of branching is desired (e.g., in a tumor). Molecular techniques and methods useful in the construction of expression vectors are well known in the art (e.g., Ausubel, et al., 1988; Sambrook, et al., 1989). A number of such vectors are known. They typically include at least one restriction site into which a desired coding sequence can be inserted, as well as a tissue-specific promoter operably linked to the coding sequence to control transcription of the coding sequence in the cell. Exemplary tissue-specific promoters for use in cancer therapy include the $\alpha$-fetoprotein promoter for liver targeting, and the short metallothionein promoter for neoplasms, such as B-cell neoplasms, expressing immunoglobulin enhancer.

The constructs can be tested by transfecting suitable animal models, e.g., tumor models such as the nude mouse model of Ossnowski, et al., 1991. Any of a number of methods known to those skilled in the art may be used to introduce gene therapy vectors of the present invention into selected target tissue cells, e.g., tumor cells. For example, the vectors may be introduced using viral-mediated gene transfer. In this technique, host cells are trasfected by infection with mature virions containing hybrid vectors (constructs encoding Spry along with selected viral sequences). The virions used to transfect host cells are preferably replication-defective, such that the virus is not able to replicate in the host cells.

The virions may be produced by co-infection of cultured host cells with a helper virus. Following coinfection, the virions are isolated (e.g., by cesium chloride centrifugation) and any remaining helper virus is inactivated (e.g., by heating). The resulting mature virions contain a construct or chimeric gene of the present invention and may be used to infect host cells in the absence of helper virus. Alternatively, high titers of replication-defective recombinant virus, free of helper virus, may be produced in packaging cell lines containing those components for which the virus is defective.

Alternatively, the vector construct can prepared as a gene therapeutic composition, for example, by complexing the DNA vector with a polycationic agent, such as polylysine, preferably in an amount sufficient to produce stoichiometric charge neutralization, e.g., a 1:1 charge ratio. The polycation may be additionally conjugated with a targeting agent, e.g., a tumor-antigen-specific binding agent, for tumor targeting. Methods for producing DNA-polylysine-targeting moiety complexes of this type, in the 40–150 nm size range are well known.

The therapeutic complex can be administered by a variety of methods, including intravenous injection, catheter delivery, or direct injection into a tumor mass, or ex vivo transfection of tissue or blood cells.

The following examples illustrate but in no way are intended to limit the present invention.

MATERIALS AND METHODS

Unless otherwise indicated, all reagents were purchased from Sigma Chemical Company (St. Louis, Mo.).

Abbreviations used below include the following. PAGE: polyacrylamide gel electrophoresis; SDS: sodium dodecyl sulfate; BSA: bovine serum albumin.

A. Fly Strains and Genetics

Three P-element insertions in the Spry locus ($Spry^{2683}$, $Spry^{1814}$ and $Spry^{9143}$) were identified in an enhancer trap screen and were referred to as the Pantip-2 markers (Samakovlis, et al., 1996). $Spry^{2683}$ is homozygous viable and shows normal tracheal branching. $Spry^{2683}$ and $Spry^{1814}$ contain a P[lacZ,w+] element (Bier, et al., 1989) at 63D1,2. $Spry^{9143}$ contains a P[lacZ,ry+] element.

B. Antibody, BrdU and TUNEL Staining

Embryos were fixed in formaldehyde, devitellinized in methanol and stained with antibodies as described (Samakovlis, et al., 1996). Embryos were stained with the following antibodies: mouse IgM mAb 2A12 against an anonymous tracheal lumenal antigen (1:5; Samakovlis, et al., 1996); rabbit polyclonal antiserum against beta-galactosidase (1:1500; Cappell, Durham, N.C.); mouse IgG mAb against Drosophila serum response factor (1:1000; Guillemin, et al., 1996); mouse IgG mAb against Notch protein (1:3000). Biotin-, Cy5-, Cy3- or FITC-conjugated secondary antibodies, obtained from Jackson Immunoresearch (West Grove, Pa.), were used at 1:300. HRP histochemistry was performed with "VECTASTAIN" ABC kit (Vector Laboratories, Burlingame, Calif.).

5-bromodeoxyuridine (BrdU) and terminal deoxyribonucleotidyl transferse (TdT)-mediated biotin-16-dUTP nick-end labelling (TUNEL) staining were done as previously described (Samakovlis, et al., 1996) using wild type and $Spry^{\Delta 5}$ embryos from stages 10 to 16.

C. Molecular Analysis of Spry Mutants

Defects in the Spry excision mutants were determined by analyzing genomic Southern blots of wild type and mutant genomic DNA probed with genomic fragments flanking the P element insertion site, the full P[lacW] element, and the Spry cDNA 12.2. To identify mutations in the EMS-induced mutants, the complete coding sequence and 122 bp of flaking DNA in the Spry locus was determined by cycle sequencing (femtomol cycle sequencing, Promega) of PCR-amplification products of genomic DNA from the mutants. Genomic DNA was isolated from third instar larvae carrying a Spry EMS-allele over Df(3L)HR119 (Lis, et al., 1983). Two independent PCR-products were sequenced for each allele.

D. Antibody Production and Staining

Full-length (nucleotides (nt) 1323–3098), N-terminal (nt 1509–2708) and C-terminal (nt 2772–3098) coding fragments of the Spry 12.2 cDNA were amplified by PCR and inserted 3' of the GST coding sequences in pGEX-4T-2 (Pharmacia Biotech, Piscataway, N.J.). Spry fusion proteins were purified by glutathione affinity chromatography (Pharmacia) and injected into rabbits and mice at Josman Labs (Napa, Calif.). Antisera were affinity-purified using full-length GST-Spry fusion protein coupled agarose beads (Pierce Chemical, Rockford, Ill.). Antisera were preabsorbed overnight at 4° C. against 0–2 hr fixed embryos and used the supernatant was used at 1:500–1:1000 for embryo staining and 1:5000–1:10000 for immunoblots.

Antiserum 26A was generated using the full-length Spry fusion protein. 0.25 micrograms of the fusion protein were injected in Freund's adjuvant five times at two week intervals. Serum was collected one week after final injection.

EXAMPLE 1

Spry Mutagenesis

The mutant $Spry^{2683}$, which shows normal tracheal branching (see Materials and Methods, above), was used in mutagenesis studies as follows. Excisions of the P[lacW] insertion in $Spry^{2683}$ were generated by crossing in a third chromosome carrying Δ2–3 to supply transposase. 100 white-eyed males from independent excision events were isolated and established as balanced stocks over a balancer chromosome carrying a Ubx-lacZ transgene.

Adult progeny of these stocks were scored for the presence of a lethal mutation on the third chromosome. Embryos collected from each stock were stained with the tracheal lumenal antibody mAb 2A12 and anti-β-galactosidase antiserum, and scored for tracheal defects under DIC optics. Of the 100 excision lines, 12 were homozygous lethal, 5 were lethal with occasional escapers, 24 were semilethal and 56 were viable. Three excision alleles (5, 64, 55) formed a lethal complementation group that was lethal over deficiencies in the region and exhibited similar recessive tracheal defects.

Chromosomal deficiencies Df(3L) Hr232, Df(3L) Hr119 and Df(3L) Hr298 (Wohlwill and Bonner, 1991) and Df(3L) 1226 and Df(3L) 1227 (Lindsley and Zimm, 1992) uncover the 63D1,2 region. 1226 did not complement the lethality or tracheal phenotype of Spry alleles and Southern analysis showed that it removed all Spry exons. Hr298 did not complement Spry for tracheal phenotype but was not tested for lethality or molecular lesions. Hr232, 119 and 1227 partially complemented the Spry alleles for lethality and tracheal phenotype. Five EMS-induced Spry alleles ($Spry^{254}$, $Spry^{211}$, $Spry^{226}$, $Spry^{G5,}$ $Spry^{F7}$) were identified in a screen for dominant suppressors of the rough eye phenotype caused by ectopic expression of seven-up in photoreceptors R2 and R5 (Kramer, et al., 1995).

The terminal cell lacZ markers used were Term-1 (pruned/ SRF, (Guillemin, et al., 1996)), Term-2, Term-3, and Term-4 (Samakovlis, et al., 1996). The enhancer trap used for monitoring Spry expression was $Spry^{9143}$ because it had the strongest lacZ expression. The other Spry enhancer trap lines showed the same expression pattern, and all agreed with the whole mount mRNA in situ expression using a Spry cDNA probe (Example 7). The string-lacZ line (Edgar, et al., 1994) has lacZ expression in dividing tracheal cells. The H99/TM6b, deficiency, which removes several genes required for cell death (White, et al., 1994), was used to eliminate cell death.

EXAMPLE 2

Ectopic Branching in Spry Mutant Embryos

Figure 1B:
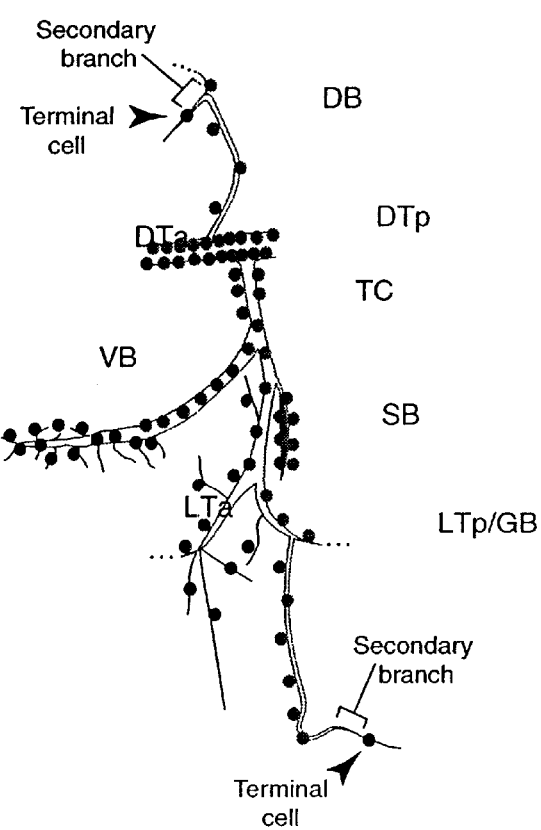
Figure 1C:
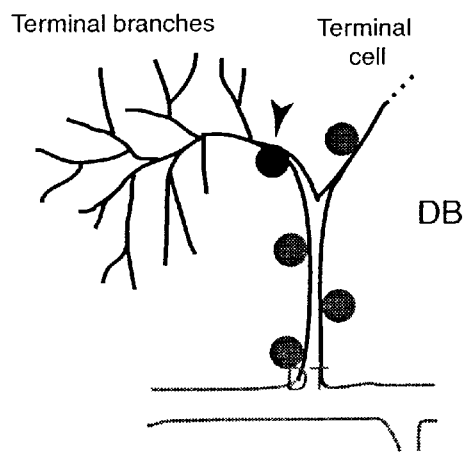

The effects of Spry mutants on tracheal morphology was assessed using immunohistochemical lumenal staining with mAb 2A12. Exemplary results are presented in schematic and photomicrograph forms in FIGS. 1 and 2, respectively. The fifth tracheal unit of the developing wild-type Drosophila tracheal system is schematized at different developmental stages in FIGS. 1A, 1B and 1C. The fifth tracheal unit, like the other repeating tracheal units, develops via unicellular branches. The tracheal lumen is outlined in black, nuclei of tracheal cells are in gray and nuclei of cells that form fine branches are filled in black.

Figure 2B:
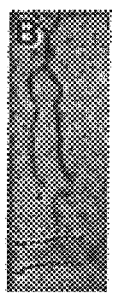
Figure 2C:
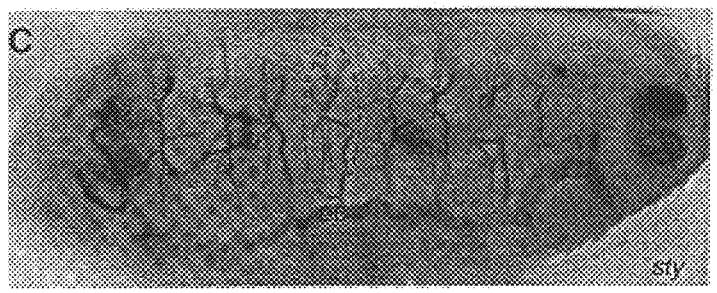
Figure 2D:
Figure 3A:
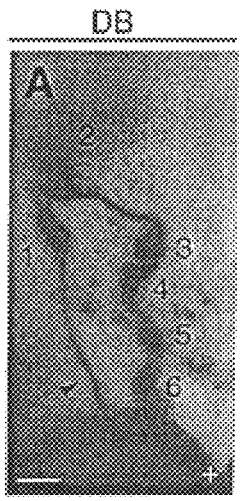
FIGS. 3A–3L show the distribution of cells and expression of branching markers in the wild type (+) and Spry$^{\Delta 5}$ mutant tracheal systems.
Figure 3B:
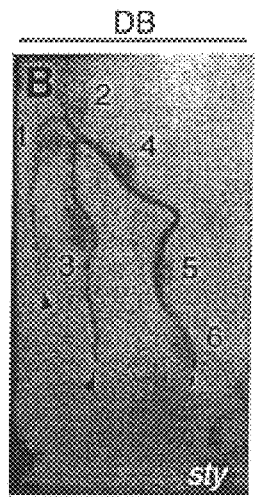

At stage 12 (FIG. 1A), six primary branches are growing out from fixed locations. By stage 16 (FIG. 1B), the primary branches have reached their final positions and individual terminal cells begin to form fine (secondary) branches. In third instar larvae (FIG. 1C), each terminal cell ramifies to form terminal branches. As discussed above, this normal branching pattern is disrupted in FIGS. 2A/2B and 2E/2F are whole-embryo/close-up photomicrographs of such primary and secondary branches in wild type (+) embryos at stage 16; FIGS. 2C/2D and 2G/2H show the corresponding branches in $Spry^{\Delta 5}$ (Spry) embryos. Dorsal branches (DB) on both sides of embryo are visible in the dorsal views shown in FIGS. 2A–2D. Note the extra branches in $Spry^{\Delta 5}$ embryos (FIGS. 2C/2D). FIG. 2B shows a close-up of one dorsal branch in wild-type, with one fine branch (arrowhead). A corresponding dorsal branch in $Spry^{\Delta 5}$ has three fine branches (FIG. 2D).

Figure 2E:
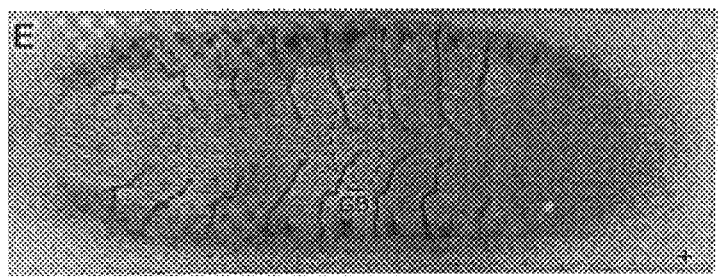
Figure 2F:
Figure 2G:
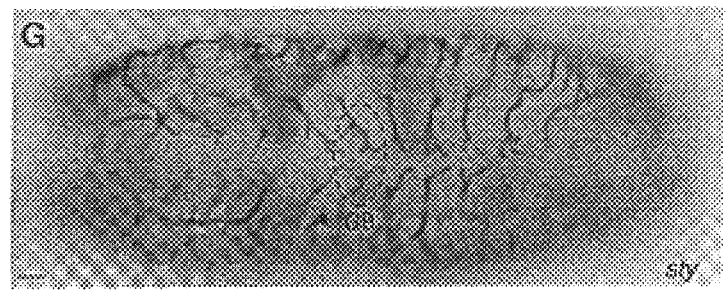
Figure 2H:

FIGS. 2E/2F and 2G/2H are ventral views showing ganglionic branches (GB). FIGS. 2F and 2H show close-up of one ganglionic branch with one fine branch in wild-type (FIG. 2F) and two fine branches in $Spry^{\Delta 5}$ (FIG. 2H).

Note that all ectopic fine branches are found nearby the normal branches. Lumen that is outside the focal plane is marked in FIGS. 2A, 2C, 2E and 2G by a dashed line. Scale bars in FIG. 2G (for FIGS. 2A, 2C, 2E, and 2G) and in FIG. 2H (for FIGS. 2B, 2D, 2F, and 2H) are 10 µm.

Five EMS-induced Spry alleles ($Spry^{254}$, $Spry^{211}$, $Spry^{226}$, $Spry^{G5}$, $Spry^{F7}$) were recovered in an unrelated screen for mutations that suppress a dominant eye phenotype (Kramer, et al., 1995). All the alleles mapped to the same genetic interval in the 63D region and had the same tracheal phenotype as $Spry^{\Delta 5}$ (Table 1, below). $Spry^{254}$ was tested and failed to complement the three original Spry alleles for tracheal function and lethality. Molecular analysis of all the EMS mutants identified lesions in Spry coding sequences (see below).

All eight Spry mutations resulted in pupal lethality in trans to deficiencies in the 63D region including Df(3L) 1226, Df(3L) 1227, Df(3L) Hr119, Df(3L) Hr232. $Spry^{\Delta 5}$ homozygotes displayed as severe a tracheal phenotype as $Spry^{\Delta 5}$/Df(3L) 1226 and $Spry^{\Delta 5}$/Df (3L) Hr298, indicating that $Spry^{\Delta 5}$ is a strong loss-of-function or null allele (Table 1, below).

TABLE 1

Tracheal Defects in *Spry* Alleles

| Genotype | Dorsal Branch* | Ganglionic Branch |
|---|---|---|
| Canton-S | 1.0 ± 0.3 (n** = 268) | 1.0 ± 0.2 (n = 380) |
| $Spry^{DS}/Spry^{DS}$ | 2.2 ± 0.6 (n = 68) | 1.7 ± 0.6 (n = 178) |
| $Spry^{DS}$/Df 1226 | 2.2 ± 0.6 (n = 39) | 1.6 ± 0.5 (n = 110) |
| $Spry^{211}/Spry^{211}$ | 2.3 ± 0.4 (n = 16) | 1.3 ± 0.5 (n = 27) |
| $Spry^{226}/Spry^{226}$ | 2.0 ± 0.5 (n = 16) | 1.6 ± 0.5 (n = 50) |
| $Spry^{254}/Spry^{254}$ | 1.8 ± 0.6 (n = 32) | 1.7 ± 0.7 (n = 18) |
| $Spry^{F7}/Spry^{F7}$ | 1.8 ± 0.4 (n = 18) | 1.4 ± 0.5 (n = 40) |
| $Spry^{G5}/Spry^{G5}$ | 2.0 ± 0.6 (n = 32) | 1.2 ± 0.4 (n = 40) |

TABLE 1-continued

Tracheal Defects in *Spry* Alleles

| Genotype | Dorsal Branch* | Ganglionic Branch |
|---|---|---|

*Average number of DSRF-expressing fine branching cells per primary dorsal (DB) or ganglionic (GB) branch. Embryos were stained with mAb 2A12 to visualize tracheal lumen, anti-SRF to mark branching cells, and anti-β-gal to distinguish homozygous mutants from balanced embryos expressing Ubx-lacZ from the TM3 chromosome.
**n = the number of tracheal segments counted.

EXAMPLE 3

Distribution of Cells and Expression of Branching Markers in the Wild Type (+) and $Spry^{\Delta 5}$ Mutant Tracheal Systems The distribution of cells and expression of branching markers in the wild type (+) and $Spry^{\Delta 5}$ mutant tracheal systems was compared. The results are shown in FIGS. 3A–3L. FIGS. 3A and 3B are photomicrographs showing dorsal branch expression of a pantracheal lacZ marker (6–81a or btl-lacZ) in wild type (FIG. 3A) and $Spry^{\Delta 5}$ (FIG. 3B) embryos. FIGS. 3C and 3D are tracings summarizing such expression in the ganglionic branch of wild type (FIG. 3C) and $Spry^{\Delta 5}$ (FIG. 3D) embryos. Arrowheads indicate fine-branching cells.

Figure 3E:
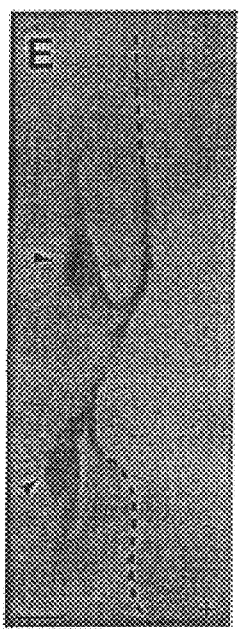
Figure 3F:
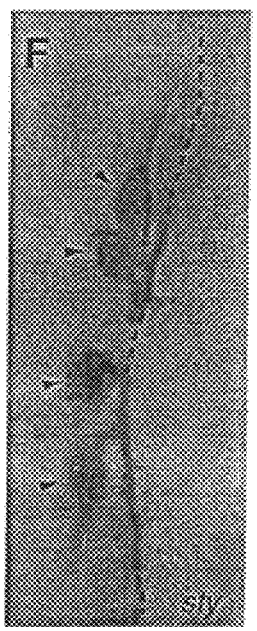
Figure 3K:
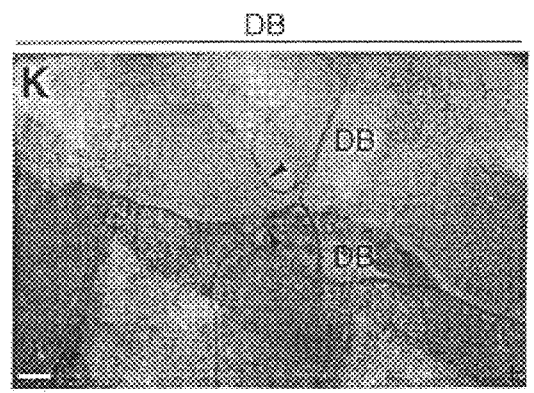
Figure 3C:
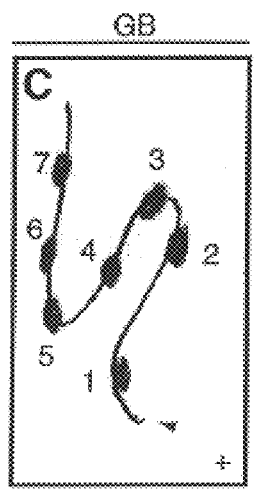
Figure 3D:
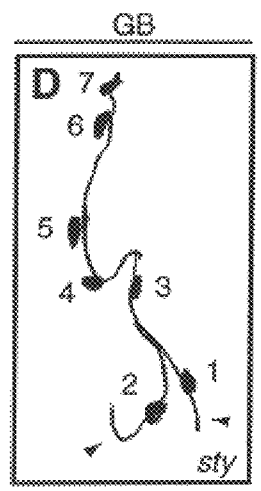
Figure 3G:
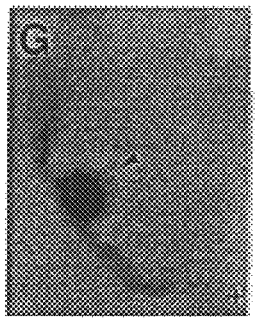
Figure 3I:
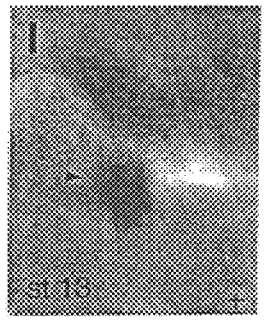
Figure 3H:
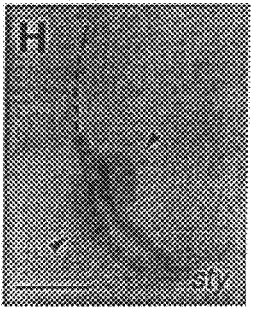
Figure 3J:
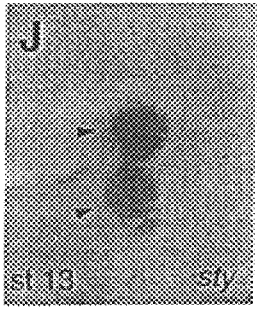
Figure 4A:
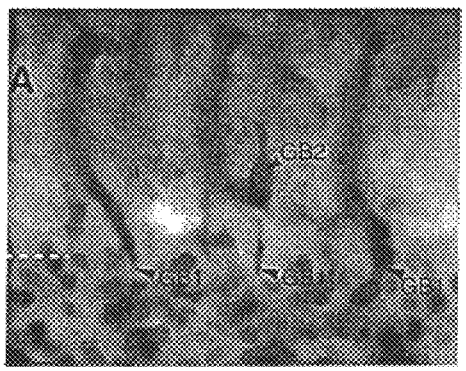
FIGS. 4A, 4B and 4C are photomicrographs of mosaic clones of Spry and wild type cells distinguished by expression (Spry$^+$) or lack of expression of cytoplasmic β-gal (Spry$^-$).
Figure 4B:
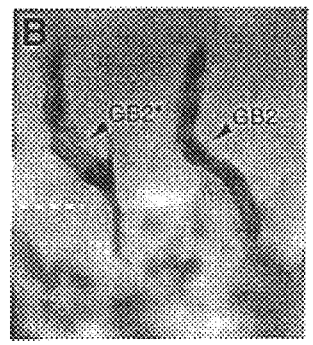
Figure 4C:
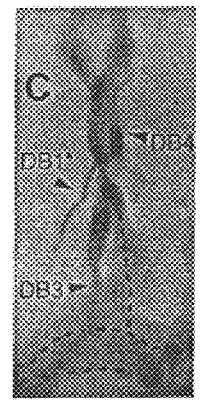

FIGS. 3E–3J are photomicrographs employing the Drosophila serum response factor (DSRF) marker, which is expressed in the nuclei of fine-branching cells in both wild type embryos and in $Spry^{\Delta 5}$ embryos. FIG. 3E is a dorsal view of a wild-type embryo showing two primary dorsal branches, with one terminal cell (arrowhead) in each branch. FIG. 3F is a dorsal view of a $Spry^{\Delta 5}$ embryo at stage 16, showing dorsal branches, each with two terminal marker expressing cells. FIG. 3G shows a wild-type ganglionic branch at stage 16, with one terminal cell. FIG. 3H shows a $Spry^{\Delta 5}$ ganglionic branch at stage 16, with two terminal cells. FIG. 3I shows a wild type ganglionic branch at stage 13, with one terminal cell, at the point when the terminal marker just begins to turn on. FIG. 3J shows a $Spry^{\Delta 5}$ ganglionic branch at stage 13, with two terminal cells.

Figure 3L:
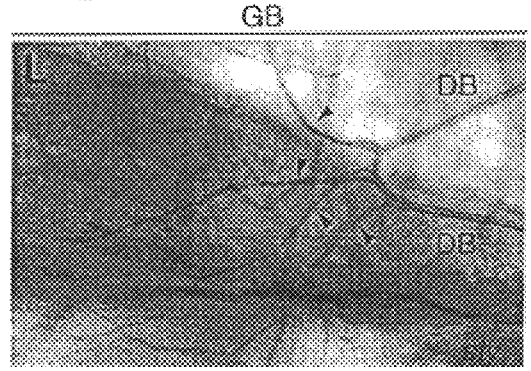

FIG. 3K is a larval view photomicrograph of two wild type larval dorsal branches (DB), each with one terminal cell that gives to rise to an extensively ramified branch (arrowhead). FIG. 3L is a photomicrograph of a $Spry^{\Delta 5}$ type larval dorsal branch terminal cell, with two terminal cells giving rise to further branches. Scale bars in FIG. 3A (for FIGS. 3A–D), FIG. 3E (for FIGS. 3E–F) and FIG. 3H (for FIGS. 3G,J) are 5 µm. Scale bar in FIG. 3L (for FIGS. 3K–L) are 10 µm.

Taken together with the data in Example 2, the above results indicate that the extra branching in $Spry^{\Delta 5}$ mutants was due to an increased number of branch-forming cells rather than an increased number of branches formed by the normal group of branch-forming cells. Staining of $Spry^{\Delta 5}$ mutant embryos with a nuclear marker expressed in all tracheal cells showed that there was a parallel increase in the number of branch-forming cells, each associated with an extra branch (FIG. 3B, D).

The results do not suggest that the extra branching cells in Spry mutants arise from excess cell proliferation, diminished cell death or ingression of cells from other tissues. It is unlikely that additional cell division in the mutants could have generated the extra branching cells, since cell counts showed that although the total number of cells in a typical hemisegment (Tr5) that formed fine branches increased from ~20 to ~30 in the Spry$^{\Delta 5}$ mutant, the total number of tracheal cells was not correspondingly increased (78+/−4 cells in wild typeTr5 (n=6) vs. 73+/−3 in Spry$^{\Delta 5}$ Tr5 (n=3)). Furthermore, no additional dividing cells were detected in Spry$^{\Delta 5}$ embryos by labeling with BrdU or a string-lacZ marker that expresses lacZ in dividing cells. The extra branching cells are also unlikely to have arisen from suppression of normal cell death since cell death does not appear to occur during wild type tracheal development (Samakovlis, et al., 1996) and no extra branches were observed in the H99 deficiency mutant which prevents all normal cell death (White, et al., 1994).

The above results do indicate, however, that the extra branching cells arise by the conversion of non-branching tracheal cells into branch-forming cells. As shown in FIGS. 3F and 3H, the ectopic branching cells in Spry mutants expressed the normal secondary and terminal branch markers, and these markers were activated at the same time as in normal branch forming cells (FIG. 3J). Cells at the corresponding position in wild type trachea did not express these markers (FIGS. 3E, 3G and 3I). The ectopic branching cells in Spry mutants also followed the same developmental program as the normal branching cells, extending long cytoplasmic processes in parallel directions and forming extensive networks of terminal branches in the larva (FIGS. 3K and 3L). Thus, by all available criteria, the ectopic branch forming cells in Spry$^{\Delta 5}$ mutants were indistinguishable from the normal branch-forming cells.

EXAMPLE 4

Genetic Mosaic Analysis of Spry in the Developing Tracheal System

A genetic mosaic analysis of Spry in the developing tracheal system was carried out to determine in which cells the Spry gene functions to inhibit branching. The Spry$^{\Delta 5}$ mutation was recombined onto the left arm of a third chromosome carrying a FLP recombination site (FRT) near the centromere (Xu and Rubin, 1993). 1-eve-1, a lacZ enhancer trap marker at 61E expressed in all tracheal cells (Perrimon, et al., 1991), was recombined onto a separate FRT third chromosome. The 1-eve-1-FRT chromosome was crossed into hsFLP;Dr/TM3ry flies, which carry FLP recombinase under heat shock control. Resulting progeny carrying hsFLP and 1-eve-1-FRT were crossed to Spry$^{\Delta 5}$-FRT/TM3 to give progeny of the genotype hsFLP;1-eve-1-lacZ FRT/Spry$^{\Delta 5}$-FRT.

hsFLP;1-eve-1-lacZ FRT/Spry$^{\Delta 5}$ FRT embryos were collected at late stage 10 and early stage 11 at 25° C. and heat-shocked twice at 37° C. for 20 min at 5 and 6 hours AEL (after egg laying). Clones were observed 10 hours later (stage 15 or 16) after fixation and staining with the mAb 2A12 lumenal antibody and anti-β-galactosidase antiserum. Tracheal cells from 1-eve-1 that expressed cytoplasmic β-galactosidase (β-gal) were identified as Spry$^+$; cells that did not express β-galactosidase (β-gal), but that often had a thin lumenal stain, were identified as Spry$^-$ (Spry$^{\Delta 5}$/Spry$^{\Delta 5}$). Thirty six clones were identified in the dorsal and ganglionic tracheal branches. The clones and surrounding cells were carefully examined for tracheal defects. Clones were found in ~12% of embryos of the correct genotype.

Although a small number of clones were examined in the dorsal branch (DB), the analysis was focused on the ganglionic branch (GB) due to its simple structure and relative ease of determining cell identities and branching fates. In wild type embryos, the GB is composed of seven cells that grow toward the ventral nerve cord. The lead cell (GB1) always expresses secondary and terminal markers and forms fine branches, while the other six cells (GB2–7) do not express secondary or terminal markers and do not form branches.

Exemplary results are shown in the photomicrographs of FIGS. 4A, 4B and 4C, showing mosaic clones of Spry and wild type cells distinguished by expression (Spry$^+$) or lack of expression of cytoplasmic β-gal (Spry$^-$). FIG. 4A shows an ectopic branch arising from GB2 when there was no β-gal expression in the leading cell (GB1) of the ganglionic branch. Neighboring segments had GB1 cells with β-gal expression and no ectopic branches. Twenty nine such clones were analyzed. FIG. 4B illustrates a situation where no ectopic branch was seen when no β-gal expression was present in the second cell (GB2) of the ganglionic branch. Four such clones were analyzed. In FIG. 4C, ectopic branches are seen arising from DB3 and DB4 when there is no β-gal expression in the leading cell (DB1) of the dorsal branch. Only four clones were found in GB2–7, presumably because the cells were crowded together and overlapped in space. The edge of the ventral nerve cord is marked with a white dashed line. Scale bar is 10 μm.

The above results demonstrate that Spry acts non-autonomously to inhibit tracheal branching. In the 29 clones in which just the GB1 cell was Spry$^-$, an ectopic branch was always present in the neighboring GB2 cell (FIG. 4A). Furthermore, three of the four identified clones of the opposite type in which non-leading cells (GB2–7) were Spry$^-$, the ganglionic branch appeared normal with no extra branches (FIG. 4B). One particularly informative Spry$^-$ clone of this type included all cells of the GB except the lead cell; this formed a normal ganglionic branch without ectopic branches. The data thus show that Spry$^+$ is required in the GB1 cell of the ganglionic branch and acts non-autonomously to inhibit branching in the neighboring cell.

Although data for the dorsal branch (DB) were more limited, they supported the results from the ganglionic branch. In the four clones in which the lead cell of the dorsal branch (DB1) was Spry$^-$, neighboring cells appeared to form ectopic branches. In the clone shown in FIG. 4C, for example, both the DB3 and DB4 cells inappropriately extended branches.

There were two unexpected characteristics of the Spry$^-$ clones in which the GB1 cell was mutant. First the outgrowth of the ectopic branches tended not to follow the same outgrowth pathway as when the entire animal was Spry$^-$; they typically turned away from the ventral nerve cord (FIG. 4A) whereas the extra branches in Spry$^-$ embryos normally enter the cord (FIG. 2C). This indicates that Spry$^+$ cells in the mosaics somehow influenced branch pathfinding. Second, the outgrowth of the normal branch from the GB1 cell appeared to be inhibited in clones in which the GB1 cell was Spry$^-$ but the neighboring cells (GB2–7) were Spry$^+$. This suggests that Spry$^+$ also has a cell-autonomous function that prevents inhibition of branching by its Spry$^+$ neighbors, an interpretation supported by experiments described below in which Spry protein was ectopically expressed.

EXAMPLE 5

Genomic Analysis and cDNA Cloning of the Spry Locus

A. Genomic Cloning

Genomic DNA flanking the P-element insert in Spry$^{2683}$ was recovered by plasmid rescue using standard protocols (Bellen, et al., 1989) following digestion of genomic DNA with BamHI or EcoRI. An 8 kB HindIII/BamHI genomic fragment from a BamHI rescued plasmid (5B) was used as a probe to screen ~10$^5$ phage from a Drosophila genomic library in EMBL3, and genomic phage were isolated and placed into a contig by restriction mapping and cross hybridization with each other and with plasmid rescues on Southern blots.

The results are summarized in FIG. 5A, which shows a diagram of the Spry genomic locus and gene structure. A genomic map of EcoRI (R) and SalI (S) restriction sites was assembled from the BamHI plasmid rescue and overlapping genomic phage clones (Φ3.5, 1.1, 1.2; shown at the bottom of the panel) and is represented on the top horizontal line. The insertion of the original P element, Spry$^{2683}$, is marked with a triangle, which lies 0.6 kb upstream of the class I cDNA. The origin (0 kb) is where the Spry transcription unit begins, based on mapping the 5' end of the largest class of cDNAs.

Three distinct cDNA forms were isolated and mapped onto the genomic contig of the region by the use of genomic Southerns, PCR and DNA sequencing. Exons are indicated by boxes; a filled-in box is an open reading frame; an unfilled box is an untranslated region. In the longest cDNA, the open reading frame is preceded by a 1.2 kb 5' UTR and followed by a 200 bp 3' UTR with a polyA tail. The extents of the deletions in two strong excision mutants (Spry$^{Δ5}$ and Spry$^{Δ64}$) are indicated by short vertical lines; the common 5' exon is deleted in these mutants.

B. Isolation and Characterization of cDNAs

The 8 kb HindIII/BamHI genomic fragment described above was also used to screen ~10$^6$ phage from a size-selected 9–12 hour embryonic cDNA library in λgt11 (Zinn, et al., 1988). The eleven cDNA clones isolated fell into three size classes: class I (3.2 kb; clones 3.1, 12.2), class II (2.8 kb; clones 2.4, 3.5, 11.1, 12.4, 13.1, 13.2, 13.3, 13.5) and class III (1.7 kb; clone 11.3). The size classes correspond to the three splice forms shown in FIG. 5A.

The assignment of classes was verified by cross-hybridization and restriction enzyme analyses. Several cDNAs (clones 12.2, 11.3 and 13.3) were sequenced on both strands using Sanger dideoxy sequencing methods (United States Biochemical, Cleveland, Ohio). Exons were mapped by hybridization of cDNA fragments to digested genomic phage DNA. Intron/exon boundaries were determined by PCR analysis of genomic DNA using primers from the cDNAs and by sequencing the relevant regions of genomic DNA.

These cDNAs were verified as corresponding to the Spry transcription unit as follows. First, whole mount mRNA in situ hybridization using the 3.2 kb cDNAs as probes detected an expression pattern that corresponded precisely to the lacZ pattern found for the four extant Spry enhancer trap lines (Example 7), and expression in the developing tracheal system was consistent with the genetic mosaic analysis of Spry function (Example 4). Second, molecular analysis of Spry mutations revealed deletions and non-sense mutations in the identified transcription unit in all eight Spry alleles. In the two strong Spry excision alleles (Spry$^{Δ5}$, Spry$^{Δ64}$) the 5' exon common to all splice forms was deleted (FIG. 5A), and in the weaker excision allele (Spry$^{Δ55}$) there was a complex rearrangement that included this exon. Sequence analysis of the EMS alleles revealed non-sense or frameshift mutations in each of the five alleles (Spry$^{254}$, Spry$^{211}$, Spry$^{226}$, Spry$^{G5}$, Spry$^{F7}$) that would result in truncated polypeptides lacking all or most of the conserved motif described below. Third, ectopic tracheal expression of the cloned cDNA inhibited tracheal branching, as expected from the genetic analysis (Example 8). And finally, using antisera raised against the Spry protein, no Spry protein was detected in Spry$^{Δ5}$ eye imaginal discs.

FIG. 5C shows the polynucleotide sequence of cDNA clone 12.2. The 5'- and 3'- untranslated regions are designated by small letters. The four nucleotides, CTAC, preceding the ATG match at 3/4 bases to the consensus start site [C/A]AA[A/C]. Several stop codons are located upstream and in frame to the ATG. The position of single base nonsense mutations are marked as grey circles on the base that is altered. The changes in the mutants are as follows: in 226 $C_{2055}{\rightarrow}T$; in 211 $C_{2253}{\rightarrow}T$; in G5 $G_{2710}{\rightarrow}A$; in F7 $C_{2466}{\rightarrow}T$. Spry$^{254}$ has a small deletion from 2237–2243 (grey oval) and an insertion of two nucleotides (TA) following $A_{2236}$.

As is shown in FIG. 5C, clone 12.2 is composed of two exons which are joined at the narrow arrowhead (between nt 1126 and nt 1127). The second (2.2 kb) exon contains a single long open reading frame (ORF). The broad arrowhead between nt 467 and 468 indicates an alternative start site that generates the smaller transcripts of class II (such as cDNA 13.3).

C. Identification of Sprouty Homologs

An NCBI BLAST search of the combined databases did not detect any closely related proteins. However, a search of the expressed sequence tag (dbEST) database identified three human homologs referred to herein as hSpry1 (SEQ ID NOs:5, 6) (clone 142025, IMAGE consortium clones, Lennon, et al., 1996), hSpry2 (SEQ ID NOs:7,8,9) (clone 40262), and hSpry3 (SEQ ID NOs:10,11; clone XAP128). A complete coding sequence was determined for hSpry2 (40262) (SEQ ID NO:7) and a partial sequence was determined for hSpry1 from overlapping cDNAs (142025, 78383 and 727987), (SEQ ID NO:5).

The hSpry2 sequence predicts a 315 residue polypeptide with a mass of 35 kD. It contains a cysteine-rich domain which is highly conserved with Spry (51% identity with 21 of the 22 Spry cysteines conserved) and two additional short stretches of similarity with Spry in the N-terminal region. hSpry1 and hSpry3 also show strong conservation of the cysteine-rich domain, with 51–70% identity to other family members in the available sequences.

Additional mouse ESTs found to be part of the sprouty gene family included mSpry1, SEQ ID NOs:12,13 (907842), mSpry2, SEQ ID NO:14 (819774) and mSpry4, SEQ ID NOs:15,16 (919795).

An alignment of the full hSpry2 sequence and partial sequences of hSpry1 and hSpry3 with the Drosophila Spry sequence is shown in FIG. 5D.

D. Northern Analysis

The 8 kb HindIII/BamHI genomic fragment described above and cDNA clone 12.2 were used to probe developmental Northern blots of embryonic mRNA. The mRNA was prepared by standard phenol/chloroform extraction of total RNA (Sambrook, et al., 1989) from 0–1.5, 1.5–5, 5–11, 11–16, 16–22 hour embryos at 25° C. followed by selection on oligo-dT paramagnetic beads (Promega, Madison, Wis.).

PolyA+ RNA was transferred to a "HYBOND" filter (Amersham, Arlington Heights, Ill.) and probed with radio-labelled cDNA 12.2 or 8 kb clone.

Figure 5B:
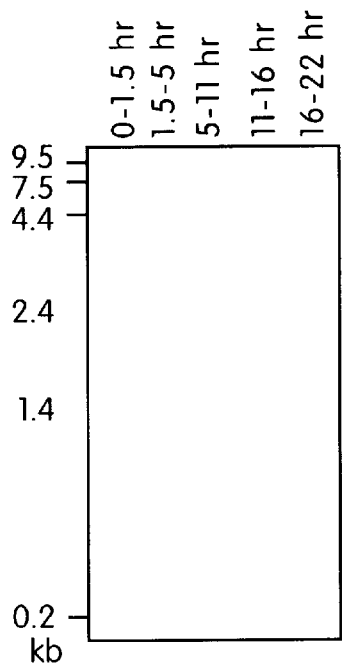
FIG. 5B shows the expression pattern of Spry.
Figure 5C:
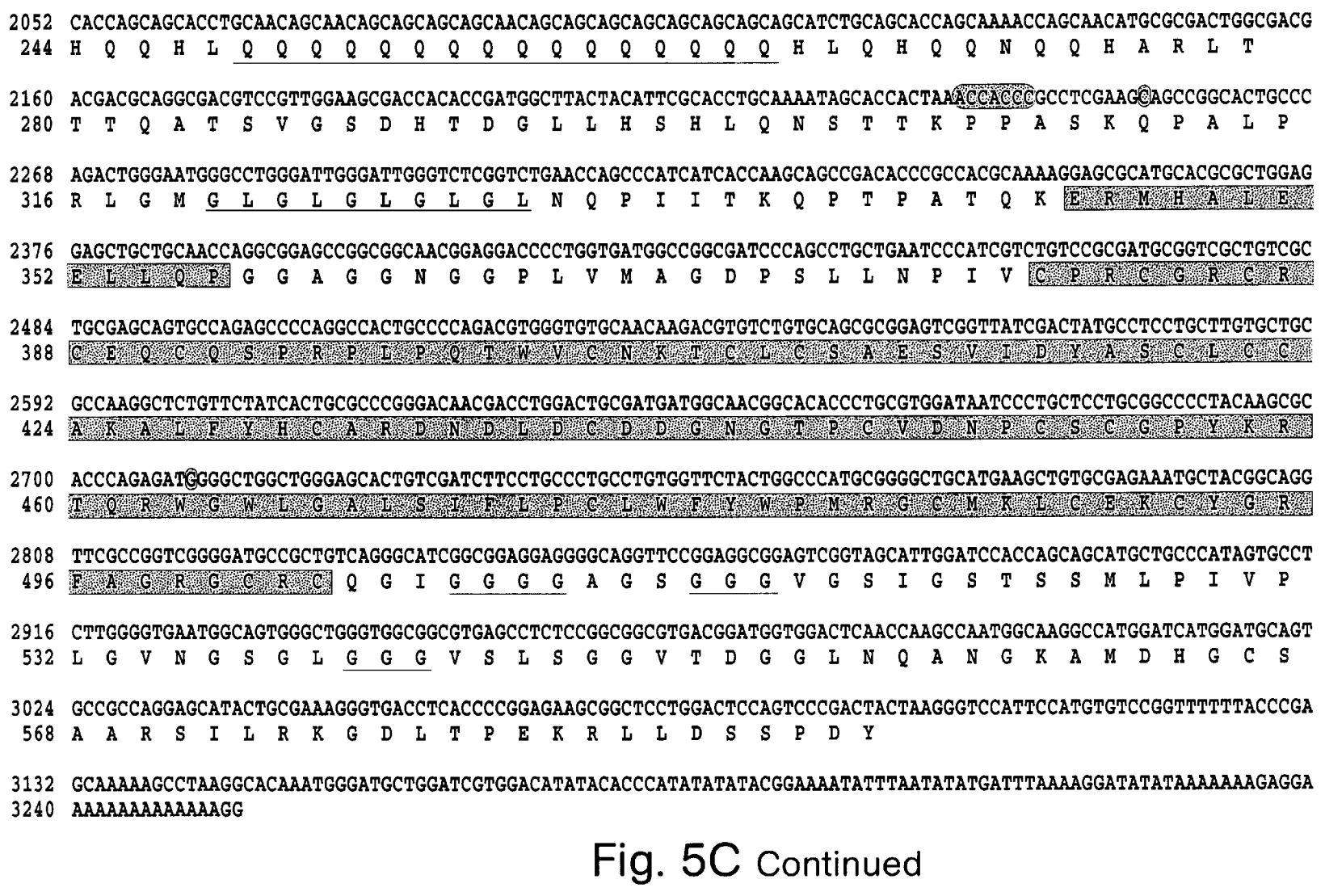

Exemplary results are shown in FIG. 5B. Three species between 3.2 and 4.4 kb were detected using the cDNA 12.2 probe. As can be appreciated from the figure, the mRNAs turned on just after tracheal development began and continued to be expressed throughout the period of tracheal development.

EXAMPLE 6

Localization of Spry Protein to the Plasma Membrane

Spry protein distribution was analyzed using affinity-purified antiserum 26A, which was raised against full-length Spry protein. Although this antiserum was not sensitive enough to reproducibly detect the endogenous Spry expression pattern in embryos, specific expression was detected in intracellular vesicles and cell membranes in developing eye discs where Spry has been shown to function.

Figure 6A:
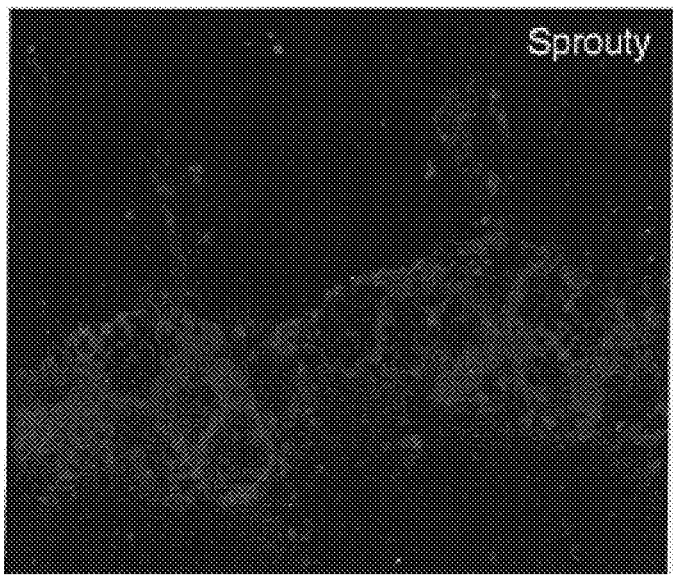
FIGS. 6A, 6B and 6C are photomicrographs of stage 14 embryos showing the subcellular localization of Spry (red) and notch (green) proteins.
Figure 6B:
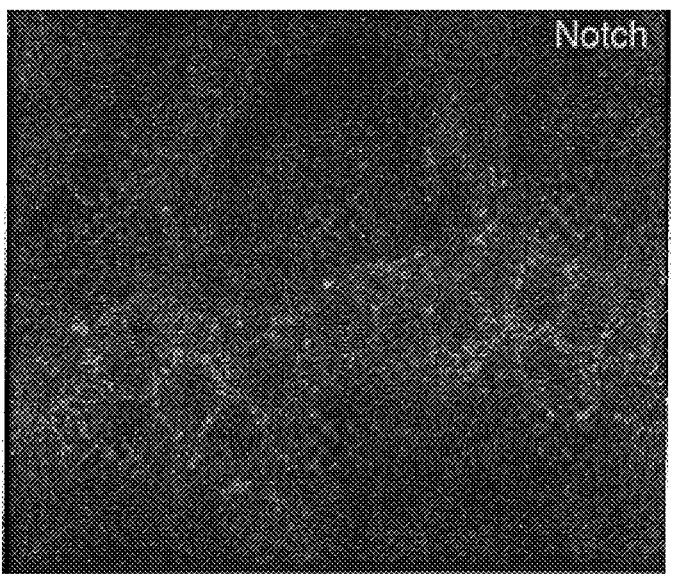

To determine the subcellular localization of Spry in tracheal cells, Spry was overexpressed in C38;UAS-Spry embryos using the GAL4/UAS system. The dorsal trunk and branches were stained at stage 14 with antiserum 26A, shown as red staining in FIG. 6A. The same dorsal trunk was also stained with anti-Notch antibody, shown in green (FIG. 6B). The two images are shown merged in FIG. 6C, with yellow staining representing co-localization of Spry and Notch proteins. Scale bar in FIGS. 6A and 6B is 5 μm.

Figure 6C:
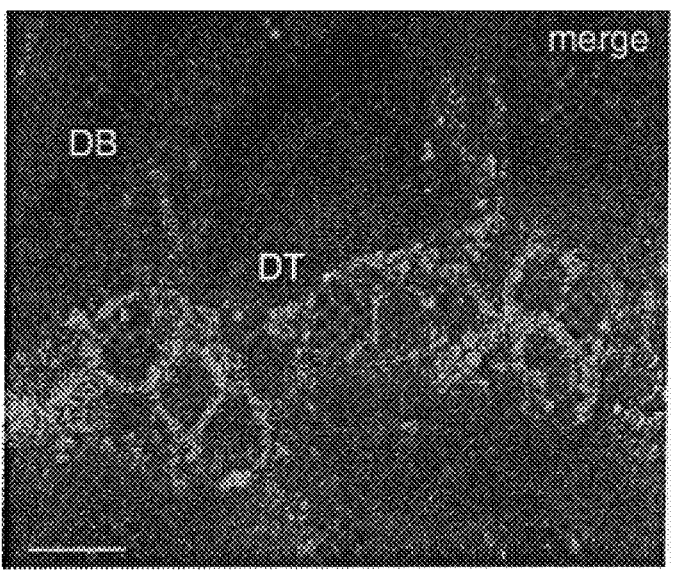

As can be appreciated from the figures, Spry (red) staining was localized at or near the surface of tracheal cells. Further, this staining co-localized with the (green) staining of the control trans-membrane protein Notch (FIGS. 6B and 6C). These data support the conclusion that Spry is a membrane bound or secreted protein.

EXAMPLE 7

Level of Spry Expression in the Branch-Forming Tracheal Cells

The embryonic expression pattern of Spry was determined by whole-mount in situ hybridization using a 3.2 kb (clone 12.2) Spry cDNA as a probe, and by analysis of the three Spry enhancer trap inserts as described above. The enhancer trap inserts closely mimic mRNA expression but provide greater cellular resolution.

In situ hybridizations were performed by fixing and processing wild type embryos using standard methods (Tautz and Pfeifle, 1989). An 8 kb HindIII/BamHI genomic fragment and a 3.2 kb cDNA clone (clone 12.2), described above, were labelled by random priming with digoxigenin labelled nucleotides and used to probe the embryos.

Figure 7A:
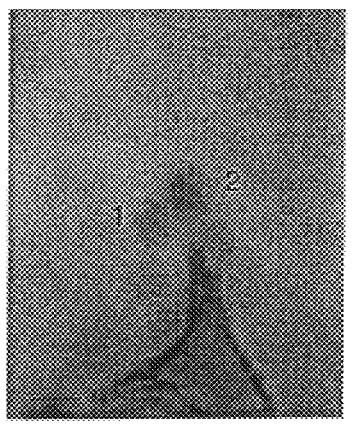
FIGS. 7A–7H are photomicrographs showing the time-course of Spry-lacZ (FIGS. 7A–7D, 7F and 7H) and Spry mRNA (FIGS. 7E and 7G) expression in Drosophila embryos.
Figure 7B:
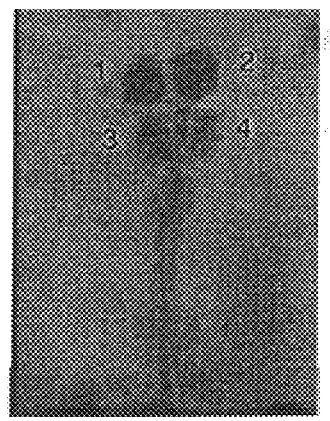
Figure 7C:
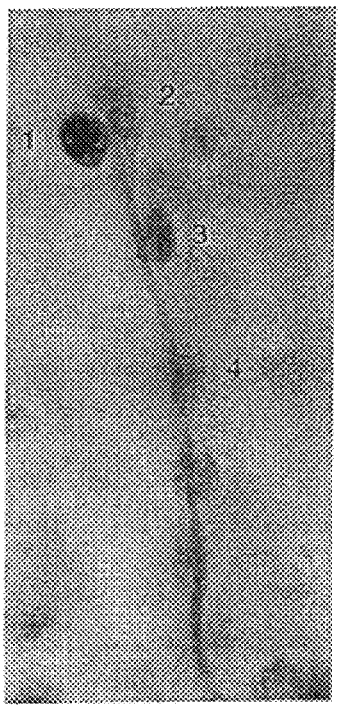
Figure 7D:
Figure 7E:
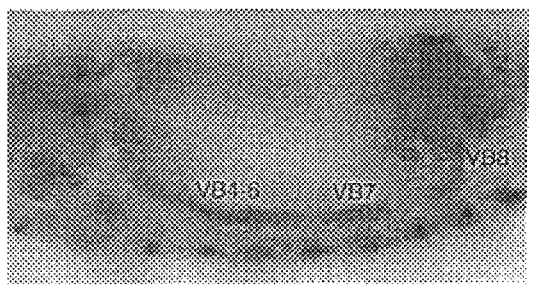
Figure 7F:
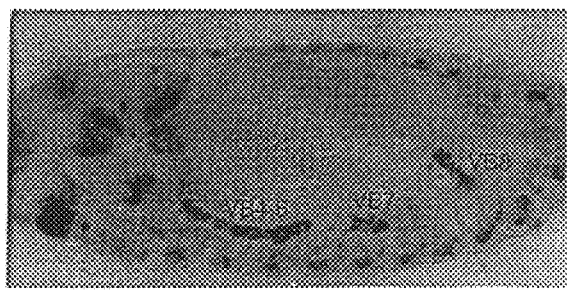
Figure 7G:
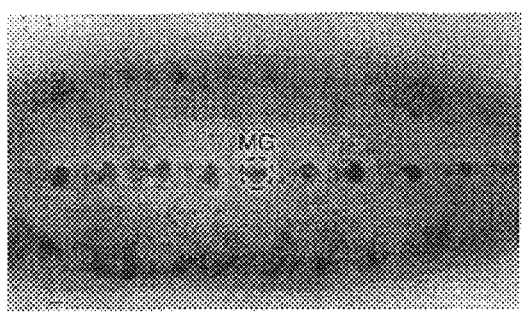
Figure 7H:
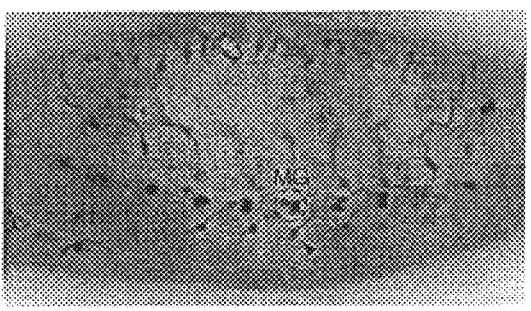

The results are shown in FIGS. 7A–7H. The photomicrographs in FIGS. 7A–7D show the timecourse of Spry-lacZ expression in Spry$^{9143}$ embryos in the dorsal branch. FIG. 7E shows Spry mRNA expression at stage 14 in the visceral branches (VB) and (G) midline glia (MG, dashed circle). FIG. 7F shows Spry-lacZ expression at stage 15/16 in VB and (H) MG. Arrowhead shows the GB1 staining which is not detectable by mRNA staining before stage 15. FIGS. 7G and 7H show expression of Spry in midline glial cells. Scale bars in FIG. 7A (for FIGS. 7A–D) and FIG. 7G (for FIGS. 7E–H) are 5 μm.

The results show that Spry is expressed specifically in the tracheal system and other tissues, including the midline glia (FIG. 7H), a group of neurons in the VNC, the dorsal vessel, oenocytes, and the eye imaginal disc.

Tracheal expression was first detected in all primary branches as they began to bud, and was maintained at high levels in the primary branch cells that go on to form secondary and ultimately terminal branches. Expression in the dorsal branch is shown in FIGS. 7A–D. At stage 12 Spry was expressed in two cells (DB1, 2) at the leading edge of the dorsal branch and less intensely in two more proximal cells (DB3, 4) (FIG. 7A).

At stage 13, there was a gradient of Spry expression, with highest expression in the two leading cells of the branch (FIG. 7B), which begin to separate such that each forms a discrete branch. From stages 13 to 15, Spry was expressed most strongly in the DB1 cell (FIG. 7C), and was ultimately expressed in this cell alone (FIG. 7D); this is the cell that goes on to form fine terminal branches in the late embryo (stage 16/17) and throughout larval life.

Taken together, these results indicate that Spry is expressed at high levels in the branch-forming tracheal cells.

EXAMPLE 8

Effect of Spry Ectopic Expression on Tracheal Branching

The GAL4-UAS expression system (Brand and Perrimon, 1993) was used to test the effect of expressing Spry at uniform levels throughout the developing tracheal system. A transgenic line was made containing Spry under the control of UAS elements, which can be driven by the GAL4 protein, as follows.

A 2.2 kb EcoRI fragment from cDNA 12.2 containing the entire Spry ORF was inserted into the pUAST vector (Brand and Perrimon, 1993) at the EcoRI site downstream of the promoter and Gal4 UAS binding sites to generate pUAST-SpryS2.2. The construct, along with pΔ2–3 (a transposase-expressing plasmid; Robertson, et al., 1988), was injected into $w^{1118}$ embryos. Six independent lines were generated, and an insertion on the third chromosome, UAS-Spry 4.1, was used for overexpression experiments. Similar results were obtained with the independent insertion UAS-Spry1.3. The Gal4 driver lines used were hsGal4 (Brand and Perrimon, 1993) and C38, a pantracheal driver expressed from early stage 13 onwards (Lin and Goodman, 1994).

Figure 8A:
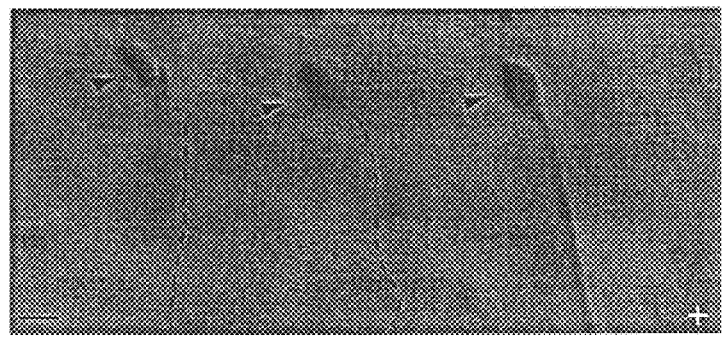
FIGS. 8A, 8B and 8C are photomicrographs showing the effects of ectopic expression of Spry protein in Drosophila embryos.
Figure 8B:
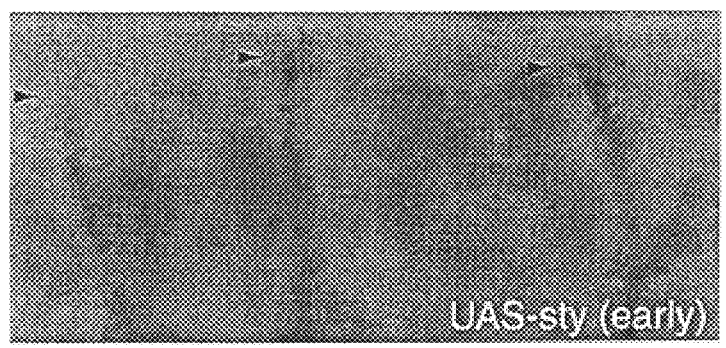
Figure 8C:
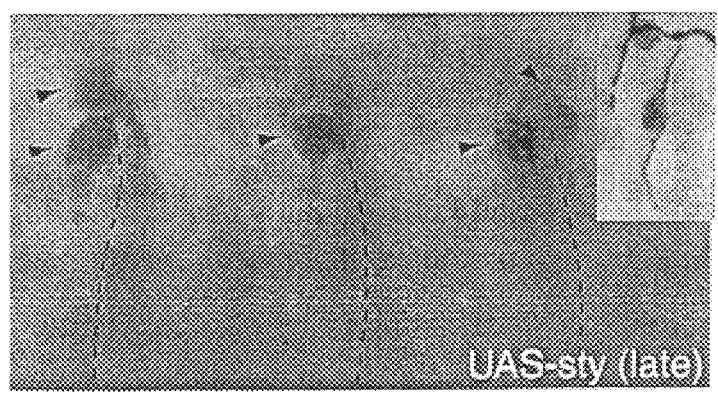
Figure 10:
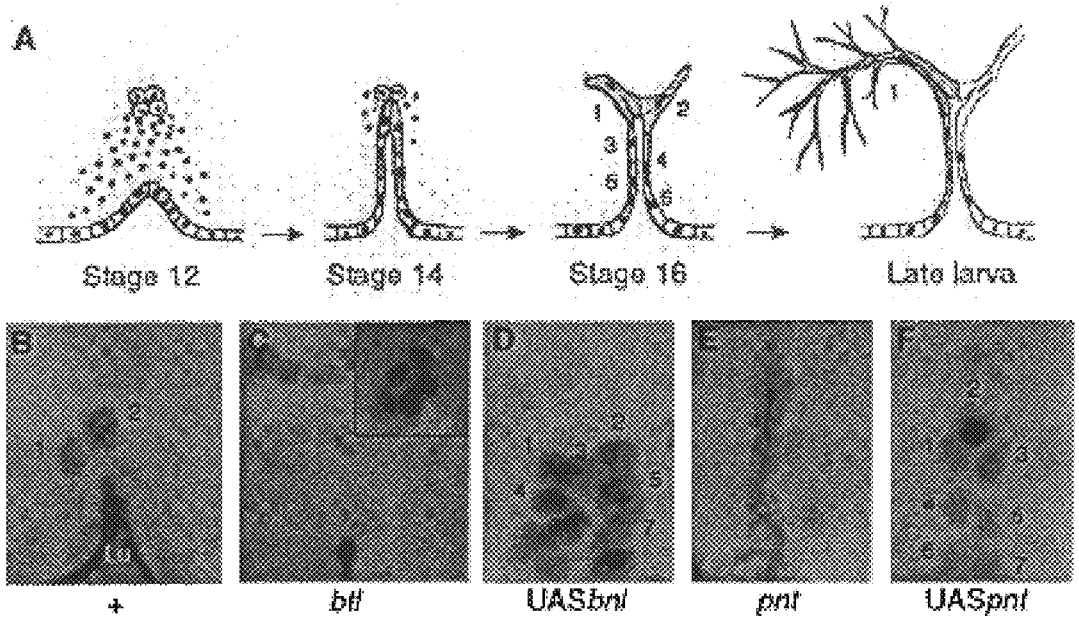
FIGS. 10A–F demonstrate the effect of Bn1 pathway mutations on Spry expression as detailed in Example 10.

The results are shown in FIGS. 8A, 8B and 8C. FIG. 8A shows wild-type DSRF (terminal cell marker) expression in terminal cells (arrowheads). FIG. 8B shows early (stage 10/11) misexpression of Spry with a hsGal4 driver suppresses DSRF expression (shown at stage 14) and subsequent terminal cell branching. FIG. 8C shows that expression of Spry at later times (stage 12) results in ectopic expression of DSRF shown at stage 14 and outgrowth of terminal branches (inset at stage 16) in some segments. Scale bar in FIG. 8A (for FIGS. 8A–8C) is 5 μm, in inset of FIG. 8C, 10 μm.

As can be appreciated, when Spry expression was induced at stage 11 and at stage 12 using a heat-shock-Gal4 strain, the branching throughout the tracheal system was inhibited, as assayed by expression of the DSRF terminal branching marker (FIG. 8B). This was expected given the excessive branching observed in the Spry loss-of-function mutants.

Surprisingly, when expression of Spry was induced at stage 13 or beyond using the hsGAL4 driver or a tracheal specific driver, branching was not inhibited. Indeed, extra DSRF-expressing cells were occasionally found in some embryos (FIG. 8C). Thus, expressing high levels of Spry early inhibits the branching program while expression at stage 13 and beyond may paradoxically stimulate branching. A model described below that reconciles these results supposes that Spry has two functions: a cell non-autonomous function as an inhibitor of branching, and a cell autonomous function which normally protects the expressing cells against the inhibitory activity.

EXAMPLE 9

Effect of Spry Mutations on Downstream Effectors in the Bn1 Signalling Pathway

A. General Approach

Secondary and terminal branching genes are induced at the ends of growing primary branches by localized expression of the Bn1 FGF in surrounding tissues (Sutherland, et al., 1996). Since the ectopic branches in Spry mutants are formed by the pre-stalk cells located just beyond the cells that are normally induced to branch, the extra branches could arise from overactivity of the Bn1 pathway.

To determine whether Spry+ functions by limiting the Bn1 pathway or whether it prevents branching in some other way, the following experiments were conducted to examine the effect of Spry mutations on downstream effectors (pnt, Yan, DSRF gene) in the Bn1 pathway that regulate the later branching events. The results are illustrated in the computer-generated images corresponding to FIGS. 9A–P.

B. Fly Strains and Genetics

The following null or strong loss-of-function alleles were used: Bn1$^{P1}$ (Sutherland, et al., 1996), btl$^{LG18}$ and btl$^{LG19}$ (Klambt, et al., 1992), pnt$^{\Delta 88}$ (Scholz, et al., 1993), and yan$^{5433}$. The P[lacZ] enhancer trap markers used were pnt$^{7825}$ (Samakovlis, et al., 1996), btl$^{6-81a}$ (Bier, et al., 1989; Samakovlis, et al., 1996), yan$^P$ (Lai and Rubin, 1992), Terminal-1 (pruned/DSRF), -2, -3, and -4 (Guillemin, et al., 1996; Samakovlis, et al., 1996), 1-eve-1 (Perrimon, et al., 1991), and Spry$^{9143}$. Spry$^{9143}$ was chosen because it has strongest lacZ expression, although the other Spry enhancer trap lines show the same pattern. The string-lacZ transgene P[w+]STGb6C from B. Edgar was used to monitor tracheal cell division.

C. Antibodies mAb A2 8B12 against Yan (1:5)

D. Misexpression of Spry and Other Genes in Vivo

Gal4 driver lines employed were hsGal4 (Brand and Perrimon, 1993), and C38 (Lin and Goodman, 1994) and TrGal4 which express GAL4 in all tracheal cells from stage 13 on.

The UAS-Spry lines were constructed by inserting the 2.2 kb EcoRI fragment from cDNA 12.2 containing the full Spry coding sequence into the P element vector pUAST and generating transformant lines. Insertions on the second (UAS-Spry4.1 #2) and third (UAS-Spry1.3 and UAS-Spry-6.2) chromosomes were used with similar results. Other UAS strains were UAS-pntP1.3 (Klaes, et al., 1994); and UAS-Bn1 (Sutherland, et al., 1996).

For experiments with the hsGal4 driver, eggs were collected for ~7 hours at 25° C., aged for 4 hours at 25°, heat shocked twice at 37° for 20 min separated by a 1.5 hr recovery, and then aged six hrs at 25°. For experiments with C38 or TrGal4 drivers, eggs were collected for 6 hrs at 25° and aged at 29° for 9 hours.

1. Effect of Spry mutations on expression of the Bnl-induced genes pnt and Spry. One effector tested was pnt, a downstream target of several receptor tyrosine kinase (RTK) pathways (Brunner, et al., 1994; O'Neill, et al., 1994; Gabay, et al., 1996). Pnt expression is induced by Bn1 at the ends of primary branches and promotes secondary and terminal branching (Samakovlis, et al., 1996; Sutherland, et al., 1996; FIGS. 2A, D).

Figure 9:
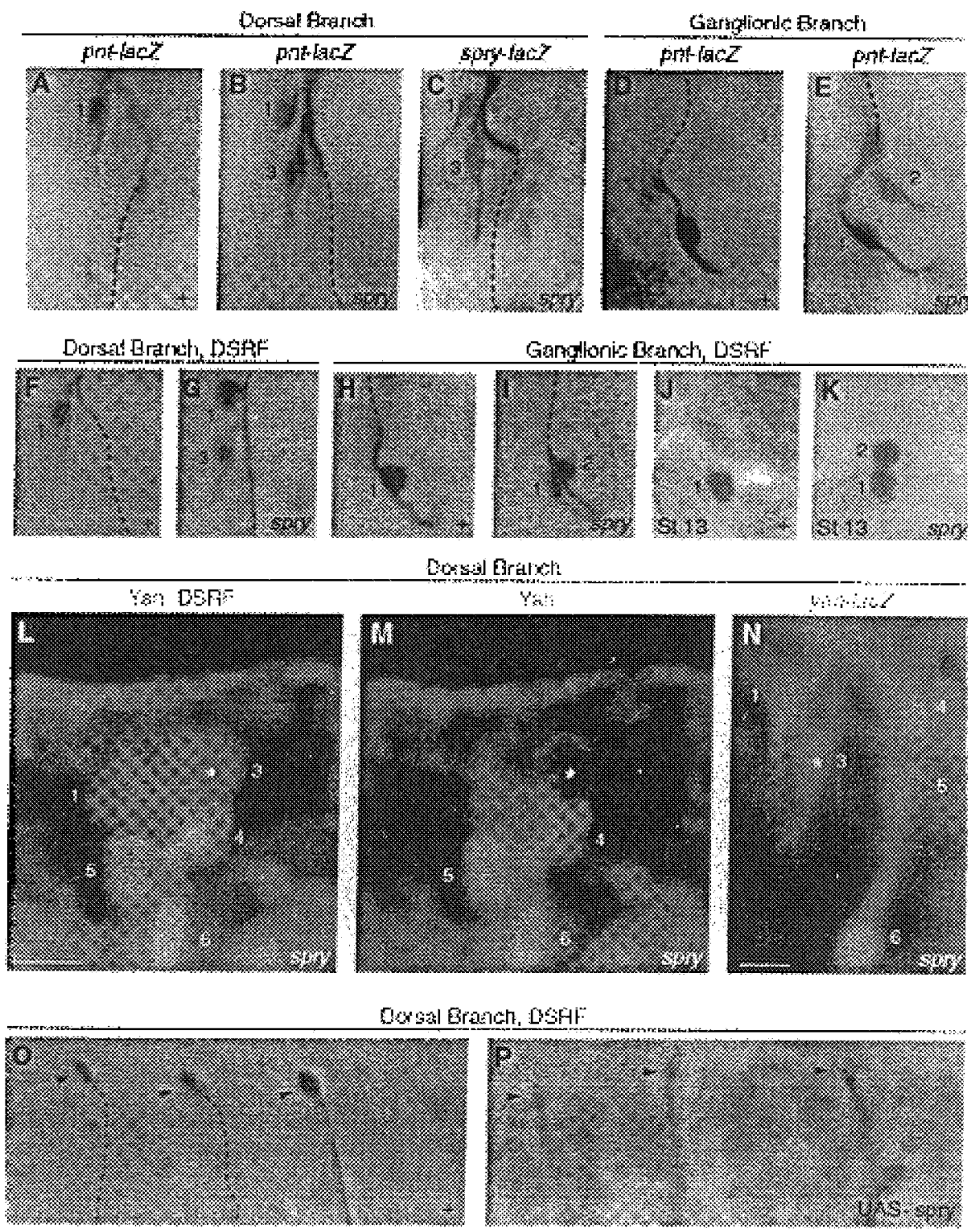

FIGS. 9 (A–E) illustrate the effect of Spry mutations on expression of the Bn1-induced genes pnt and Spry. The pnt$^{7825}$ and Spry$^{\Delta 55}$ enhancer trap markers (as described above) were used as reporters and mAb2A12 was employed to label the tracheal lumen.

FIG. 9A corresponds to wild type DB, stage 16, where high level expression of pnt is seen only in DB1. FIG. 9B corresponds to Spry$^{\Delta 5}$ homozygote. Pnt is ectopically induced in DB3. FIG. 9C illustrates the Spry$^{\Delta 55}$/Spry$^{\Delta 64}$ loss of function mutant. The results indicate that the Spry reporter is ectopically induced in DB3. FIG. D corresponds to wild type GB, stage 16. High level expression of pnt is seen only in GB1. FIG. 9E corresponds to Spry$^{\Delta 5}$ homozygote, where pnt is ectopically induced in GB2.

2. Effect of Spry mutations on expression of DSRF. FIGS. 9F–K illustrate the effect of Spry mutations on expression of DSRF, a Bn1-induced gene that controls terminal branching.

FIG. 9F corresponds to wild type DB, stage 16. DSRF expression (mAb2–161) is seen only in DB1. FIG. 9G corresponds to Spry$^{\Delta 5}$ homozygote. DSRF is ectopically induced in DB3. FIG. 9H corresponds to wild type GB, stage 16. DSRF is seen only in GB1. FIG. 9I corresponds to Spry$^{\Delta 5}$ homozygote. DSRF is ectopically induced in GB2. FIG. 9J corresponds to wild type GB, stage 13 and shows that DSRF is just beginning to be expressed in DB1. mAb2A12 antigen is not yet on. FIG. 9K corresponds to GB in Spry$^{\Delta 5}$ homozygote, stage 13. DSRF is induced in GB2 at the same time as GB1. Similar results were obtained for three other terminal branch markers (Terminal-2,-3, and -4).

To summarize, the DSRF gene and three other marker genes (Terminal-2,-3, and -4) are induced at the ends of growing primary branches and promote terminal branching (FIG. 9F, 9H). However, in the Spry mutants, all five downstream effectors were expressed in an expanded domain that included the pre-stalk cells that later formed ectopic branches (FIG. 9B, E, G, I). Furthermore, the DSRF marker was activated at the same time as in the normal branching cells (FIG. 9J,K).

3. Effect of Spry mutations on Yan expression. Another critical target of Bn1 signaling is the Yan transcription factor. As in other RTK pathways (O'Neill, et al., 1994; Rebay and Rubin, 1995; Gabay, et al., 1996), activation of the Bn1 pathway leads to MAPK-dependent phosphorylation and degradation of Yan, which is necessary to activate the later programs of tracheal branching (Hacohen, 1997).

The effects of Spry mutations on expression of Yan are illustrated in FIGS. 9L–N. In wild type, Bn1 signalling leads to degradation of Yan in DB1 and DB2. FIG. 9L illustrates that in the Spry$^{\Delta 5}$ mutant, Yan (mAb A2 8B12) is also degraded in DB3 (asterisk). Embryo was stained for DSRF (mAb2–161) to show positions of DB1 and DB3. FIG. 9M is the same as FIG. 9L without DSRF channel. FIG. 9N shows that expression of the yan-lacZ enhancer trap marker yan$^P$ is not changed in a Spry$^{\Delta 5}$ mutant, implying that the effect of Spry is post-transcriptional. Bars in L and N, correspond to 5 μm.

To summarize, Yan is normally degraded only in the tip cells of the outgrowing primary branches. In Spry mutants, Yan was degraded in an expanded domain that coincided with the expanded domains of pnt and DSRF expression (FIG. 9L, 9M). A yan-lacZ transcriptional reporter continued to be expressed normally, implying that the down regulation of Yan was a post-transcriptional event as in other RTK pathways (FIG. 9N).

The above results demonstrate that Spry loss-of-function mutations lead to enhancement of all of the known downstream effectors in this Bn1 pathway.

4. Effect of elevated levels of Spry. FIGS. 9O and 9P demonstrate the effects of elevated levels of Spry. FIG. 9O corresponds to three DBs of wild type stage 14 embryo, showing expression of DSRF in the DB1 cells (arrowheads). FIG. 9P presents a similar view of a stage 14 hsGal4/UAS-Spry 4.1 embryo heat-shocked at late stage 10 to induce Spry expression. DSRF fails to be expressed (arrowheads), and terminal branching is inhibited. When expression of Spry was induced later, at stage 13 or 14, branching was usually not inhibited, and extra branching cells were sometimes observed.

In summary, an engineered gain-of-function condition in which the Spry gene product was overexpressed during embryonic stages 10 to 12 severely blocked the normal induction of downstream effectors and branching by Bn1 (FIGS. 9O,P). The reciprocal is also true: overexpression of Bn1 can overcome the opposition of Spry and induce secondary and terminal branching throughout the tracheal system (Sutherland, et al., 1996). Thus, Spry behaves genetically as a competitive antagonist of the Bn1 pathway.

EXAMPLE 10

Induction of Spry Expression by the Bn1 Signaling Pathway

The tracheal cells that express Spry are located very close to the small clusters of epidermal and mesodermal cells that express Bn1 (see Sutherland, et al., 1996; schematized in FIG. 10A), and the Spry expression pattern is very similar to that of pnt and other genes induced by Bn1 (Samakovlis, et al., 1996). These observations suggested that Spry might also be induced by the Bn1 pathway. To test this hypothesis, the effect of bn1 pathway mutants on Spry expression was explored. The results are presented in FIGS. 10B–F in reference to FIG. 10A.

FIG. 10A is a schematic showing a cluster of Bn1-expressing cells (top circles) near the end of the growing DB (Sutherland, et al., 1996). Secreted Bn1 (dots) causes budding (Stage 12) and outgrowth (stage 14) of the primary branch. Secreted Bn1 also induces expression of genes that promote secondary and terminal branching (pnt and DSRF) in cells at the end of the primary branch (green fill) which go on to form secondary (Stage 16) and terminal branches (larva).

FIGS. 10B–F illustrate the effect of Bn1 pathway mutants on Spry expression in the developing DB, visualized by immunostaining of the Spry9143 marker. Experimental details are as described in Example 9 above.

FIGS. 10B, C, and E show the results of additional staining with lumenal antisera to show branches that don't express Spry. FIG. 10B correspond to wild type, stage 12 embryo showing the two normal Spry-expressing cells DB1 and 2, where Lu=lumen of the DB. FIG. 10C corresponds to btl$^{LG19}$ mutant. The DB does not grown out and tracheal cells fail to express Spry. Spry expression in oenocytes of the same embryo is not affected (inset). FIG. 10D corresponds to UAS-Bn1/+; hsGal4/+ embryo in which Bn1 was expressed ubiquitously. Spry is induced in all tracheal cells. FIG. 10E corresponds to pnt$^{A88}$, stage 15 embryo. Tracheal cells fail to express Spry. FIG. 10F shows UAS-pntP1.3/+; hsGal4/+ embryo in which the pnt P1 protein was expressed ubiquitously. Spry is induced in all tracheal cells, although expression is lower outside the normal expression domain presumably because of the repressor Yan.

Figure 11:
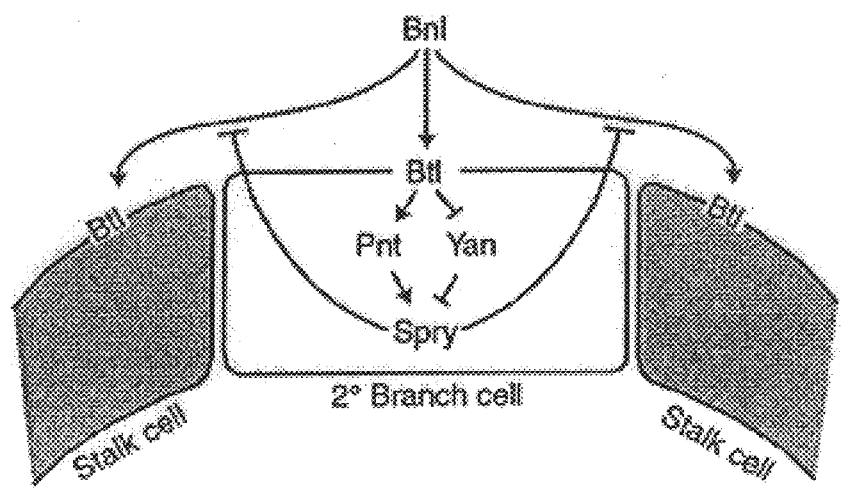
FIG. 11 presents a schematic model of a BN1-Spry regulatory circuit.

In summary, and consistent with the initial hypothesis, in Bn1 and btl mutants, Spry was not expressed or was expressed only weakly (FIG. 10C). Furthermore, when the Btl receptor was activated in all tracheal cells by ubiquitous expression of Bn1, Spry was turned on at high levels throughout the tracheal system (FIG. 10D). The downstream effector pnt was also required for Spry expression (FIG. 10E), and Spry expression was activated outside its normal expression domain when pnt P1 protein was ubiquitously expressed (FIG. 10F). Thus, Spry expression is induced by the signaling pathway that it inhibits. A schematic model of a Bn1-Spry regulatory circuit is shown in FIG. 11.

EXAMPLE 11

Spry Protein Expression and Localization in Mammalian Cells

Drosophila Spry and human Spry2 were expressed under the control of a mammalian EF-1α promoter in human 293 cells as follows.

The coding regions of the Drosophila and Human Spry2 genes were amplified by polymerase chain reaction and inserted into pEF-BOS downstream of the EF-1α promoter. The 3' primer included an in-frame epitope tag (FLAG for Drosophila Spry; HA for human Spry2) for detection of the expressed proteins with antibodies against FLAG (Santa Cruz Biotechnology) or HA (Babco) epitopes. Drosophila Spry expression was also detected with an antibody (32C) raised in rabbits against full-length Spry protein.

The pEF-BOS plasmids containing the Spry genes were transfected into 293 cells by standard procedures. Cells were harvested and lysed in standard lysis buffer (50 mM Hepes, pH 7.4, 125 mM NaCl, 1% Triton X-100) for 20' on ice. Alternatively cells were homogenized with a dounce homogenizer in sucrose buffer (50 mM Hepes, pH 7.4, 0.25 M sucrose); nuclei and cellular debris were spun down at 2,000 rpm and discarded; membranes (pellet) were separated from the soluble fraction (supernatant) at 100,000 rpm. Lysates or fractions were mixed with SDS sample buffer and run on 10–12% polyacrylamide gels which were subsequently transferred to nitrocellulose, blocked with 5% milk and incubated with primary and secondary antibodies and stained with ECL.

Proteins were detected on Western blots of cell lysates using antibodies against the appropriate epitope tag or protein. The Western blots are shown in FIGS. 12A–C. FIG. 12A shows detection of a 66 kD Drosophila Spry band, recognized by anti-FLAG antibody. FIG. 12B corresponds to detection of hSpry2 protein at 35–40 kD in 293 cells using anti-HA antibody. FIG. 12C corresponds to the 100 K rpm pellet and supernatant of homogenized cells that express Drosophila Spry.

Both proteins were efficiently expressed in this heterologous system. The molecular weights of both expressed proteins were similar to the predicted sizes of ~63 kD for Drosophila Spry and ~35 kD for hSpry2. Standard fractionation of cell homogenates revealed that the Drosophila Spry is found almost exclusively in the membrane fraction of cells.

While the invention has been described with reference to specific methods and embodiments, it is appreciated that various modifications and changes may be made without departing from the invention.

What is claimed is:

1. An isolated polynucleotide encoding a polypeptide, wherein said polynucleotide selectively hybridizes to a nucleic acid sequence selected from the group consisting of SEQ ID NO:5, SEQ ID NO:7 and SEQ ID NO:10.

2. The polynucleotide of claim 1, comprising a sequence selected from the group consisting of
   (a) nucleotides 1–135 of SEQ ID NO:5,
   (b) nucleotides 922–1054 of SEQ ID NO:7,
   (c) nucleotides 166–300 of SEQ ID NO:10,
   (d) nucleotides 41–175 of SEQ ID NO:12,
   (e) the complementary sequence of (a), (b), (c), or (d), and
   (f) a sequence at least 135 nucleotides in length that selectively hybridizes with (a), (b), (c), (d), or (e).

3. The polynucleotide of claim 1, wherein said polypeptide comprises an amino acid sequence selected from the group consisting of SEQ ID NO:6, SEQ ID NO:9, SEQ ID NO:11, SEQ ID NO:13 and SEQ ID NO:16.

4. An isolated nucleic acid, comprising the polynucleotide of claim 1, and operably linked to said polynucleotide, a regulatory sequence which promotes expression of the polypeptide in a selected host cell.

5. The polynucleotide of claim 2, encoding a human sprouty 2 protein having the sequence of SEQ ID NO:8.

6. The polynucleotide of claim 2, encoding a portion of the human sprouty 1 protein consisting of the sequence of SEQ ID NO:6.

7. The polynucleotide of claim 2, encoding a portion of the human sprouty 3 protein consisting of the sequence of SEQ ID NO:11.

8. The polynucleotide of claim 2 wherein said polypeptide comprises an amino acid sequence selected from the group consisting of SEQ ID NO:17, SEQ ID NO:18, and SEQ ID NO:19.

9. A recombinant expression vector, comprising the nucleic acid of claim 4.

10. The polynucleotide of claim 5, comprising nucleotides 391 to 1335 of SEQ ID NO:7.

11. The polynucleotide of claim 6, consisting of nucleotides 1 to 417 of SEQ ID NO:5.

12. The polynucleotide of claim 7, consisting of nucleotides 1 to 300 of SEQ ID NO:10.

13. The vector of claim 9, which is complexed with a polycation to form a condensed particle having a size less than about 150 nm, for use transfecting cells, to increase production of the polypeptide from the cells.

14. A mammalian cell comprising the vector of claim 9.

15. The vector of claim 13, wherein said condensed particle further includes a targeting moiety which binds specifically to tumor cell surfaces.

16. A method for producing a polypeptide comprising an amino acid sequence encoded by a nucleic acid which selectively hybridizes to a nucleic acid sequence selected from the group consisting of SEQ ID NO:5, SEQ ID NO:7 and SEQ ID NO:10, the method comprising
   culturing the cell of claim 14 under conditions which result in expression of the polypeptide, and recovering the polypeptide from the cell culture.

* * * * *

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
       (A) LENGTH: 3254 base pairs
       (B) TYPE: nucleic acid
       (C) STRANDEDNESS: single
       (D) TOPOLOGY: linear (ii) MOLECULE TYPE: cDNA (vi) ORIGINAL SOURCE:
       (C) INDIVIDUAL ISOLATE: Drosophila spry cDNA (ix) FEATURE:
       (A) NAME/KEY: Coding Sequence
       (B) LOCATION: 1323...3095
       (D) OTHER INFORMATION:

(xi) SEQUENCE DESCRIPTION: SEQ ID NO:1:

```
CCGCGATTGC CGCGTTCGCT GTCTTTCCGA TTTCCTCAAA AAGCAAGCCA CTTTTTTGTA    60

TAACTACAAC ATTTTTTTTC GAAGCAACCA AATCATTTAG CAAATCGAGC AACAATAGCC   120

TGCTAAACAA AACAATTCAC TACCAGAACG CGCTAAACAA CCCGCAGATA TATATTGAAA   180

ATATATATAA AACAAGCAAT CACTTGAAAA TATTGTGTGT GGTGAAAAGT GAGTGTTTAT   240

TTTTGGGAAA TAGAAATAGA AATAGTTAAC CAAGCCAACC AACCAATCGC TTCCAATGGA   300

AATCATGTGC CTAAAAATGC AAATTGCTCG AAGAAAATCA ACAACGTCTA TTTAAAAAAC   360

AAAAAAGTCA ACTCAAGCCA ATCAAATACA AAACGTGTTG GGAAAAAGTA AAAAAAAAAA   420

ATAATATAAA AATACAGCAA ATACAAAATC AAACAACAAC AGTCTCTCGC GCACACAAAT   480

ATTTTTATAA ATCTATATAT ATGTACATAT ATAAAATTGC ATAAAAATAT TTTTTACTCA   540

AGACAACGAC GCACACACAC GCAGCACCGA GATACACAGA TACATTCGCC GCTCGCACAC   600

ACACGCACAC ATAGGCGACG ACGTGGCCCC GCTTTCGGTG TGTTAGTGTA TCTGTGTGTG   660

ATTGTGCGAC GCCAGCTTCG CTGCTCCACC AACAAAAGCA ACAACCACAA CAACACTACC   720

GCCGGTCGCC AAGTTGATTA TTATTATTTT TTTGGCCAAA AACCAAAAAC CAAACCAAAA   780

CCCAGCGAAT ATATAAAAAT ACGCGGCTGG CAAAAATAAT AACAAAATCA AACATAGTCG   840

CCGGCGTCGT TTTTGTGTTA ATTAAATTTA CTTTTGTGAA TGAAATGCGA AAGAAAGCAA   900

AGCGAAAAAT CACCTTTAAT AAATGCTAAA TTAAAACCAG CAGTCGCGAT CGCGAGTAAG   960

CATCTGAAGA ACCCCCCTCT CCAAATCGCC TTTGGATTAC ACTCAAAAGA AACGAATTCA  1020

TCATTTTGGA TACTTTTCGA AAAATAAGGA TTACACAACA CTTTCAACTC ACATCTACGG  1080

TGATTAATTA CGGAATTTGT ACCACGGATT GCTTTTGAAA ATCAATAAAG CAATCGCAGC  1140

TGTCTGAATC TGCAAAAGGA TGAAGGCAAA TCAAGCTGAG TCCGGGCGCA GTAACTACGA  1200

TCGACGGCAT TGAGGATCTC GGATCTCGAG GTGGAGGAGC GATCTCGATC TCGAGGTGGA  1260

GCGAGGAGCG GAGGAGGAGT GGAGGAGTGC AGCTGGGGGA GGAGTCCTGG TTACAACACT  1320
```

```
AC ATG GAT CGC AGA AAT GGC GGC GAT CCC TTG GCG CCA CCC CGG CCC    1367
   Met Asp Arg Arg Asn Gly Gly Asp Pro Leu Ala Pro Pro Arg Pro
   1               5                  10                  15

CCG AAG TTA TTA CCG CGC GTG CAT CGA CCA AGG GCG CCG GAG CCG ACG   1415
Pro Lys Leu Leu Pro Arg Val His Arg Pro Arg Ala Pro Glu Pro Thr
            20                  25                  30
```

-continued

```
TTA AGT GGT GTC GAC CAT ACC GCA GGA GCA ACT GCA TCC GCA CTA GCA    1463
Leu Ser Gly Val Asp His Thr Ala Gly Ala Thr Ala Ser Ala Leu Ala
            35                  40                  45

TCA GGA GCA TCA TCT GCA GCA CCC GTA GCA ATC CAT AAC AAC AAT TCA    1511
Ser Gly Ala Ser Ser Ala Ala Pro Val Ala Ile His Asn Asn Asn Ser
        50                  55                  60

CAG CAG CAA CTT AGT ATT AGC GCC GCC GCG AGC AAC AAC AAT ACG ATA    1559
Gln Gln Gln Leu Ser Ile Ser Ala Ala Ala Ser Asn Asn Asn Thr Ile
    65                  70                  75

TCG ATA ATA CCC GCA TCG CCG GAC TTC GAC GAC TAC CAG ATC CAC CAC    1607
Ser Ile Ile Pro Ala Ser Pro Asp Phe Asp Asp Tyr Gln Ile His His
80                  85                  90                  95

CTG ACC TTC CTG CCC CAG CGA CCA AGC AGT CTG AGC CGG AAC AGC AGT    1655
Leu Thr Phe Leu Pro Gln Arg Pro Ser Ser Leu Ser Arg Asn Ser Ser
                100                 105                 110

ACG GCG TCA TCG ACT ACG GCG ACG GGC ATT AGT GTC TCC GGT TCG GGA    1703
Thr Ala Ser Ser Thr Thr Ala Thr Gly Ile Ser Val Ser Gly Ser Gly
            115                 120                 125

TCT GTT TCG GGT TCG TCG TCC AGC TTC ACG AGA CGT CGA CCG CCG GCA    1751
Ser Val Ser Gly Ser Ser Ser Ser Phe Thr Arg Arg Arg Pro Pro Ala
        130                 135                 140

CCT GTA CCG CTG AAC AAC AGC ATC AGC AAC AAC AAC AAC AGC ATC        1799
Pro Val Pro Leu Asn Asn Ser Ile Ser Asn Asn Asn Asn Ser Ile
    145                 150                 155

AAC AAC AAC TTC CTT AGT CAT TTC CAA AGC GCT GAG CCG GCG AGC AAC    1847
Asn Asn Asn Phe Leu Ser His Phe Gln Ser Ala Glu Pro Ala Ser Asn
160                 165                 170                 175

GCT CTG GGC CAG CCG CCC GCC TCC CCC GTC ACG CTG GCG CAA CCG CGA    1895
Ala Leu Gly Gln Pro Pro Ala Ser Pro Val Thr Leu Ala Gln Pro Arg
                180                 185                 190

CCC GAA TCC GAA AGG CTA ACC AAT GAG TAT GTG GAC ACG CCG CTG CAA    1943
Pro Glu Ser Glu Arg Leu Thr Asn Glu Tyr Val Asp Thr Pro Leu Gln
            195                 200                 205

CAT GCG ACG CGC TCG CAG CAT CCG GCT GGC CAG CAG GAT AAT GGC CAG    1991
His Ala Thr Arg Ser Gln His Pro Ala Gly Gln Gln Asp Asn Gly Gln
        210                 215                 220

ACG ACC ACC CAC CAC CTG TTG CTG CTG CCC CAG CGG AAT CAG CAC CTG    2039
Thr Thr Thr His His Leu Leu Leu Leu Pro Gln Arg Asn Gln His Leu
    225                 230                 235

CAC CTG CAA CAA CAC CAG CAG CAC CTG CAA CAG CAA CAG CAG CAG CAG    2087
His Leu Gln Gln His Gln Gln His Leu Gln Gln Gln Gln Gln Gln Gln
240                 245                 250                 255

CAA CAG CAG CAG CAG CAG CAG CAG CAT CTG CAG CAC CAG CAA AAC        2135
Gln Gln Gln Gln Gln Gln Gln Gln His Leu Gln His Gln Gln Asn
                260                 265                 270

CAG CAA CAT GCG CGA CTG GCG ACG ACG ACG CAG GCG ACG TCC GTT GGA    2183
Gln Gln His Ala Arg Leu Ala Thr Thr Thr Gln Ala Thr Ser Val Gly
            275                 280                 285

AGC GAC CAC ACC GAT GGC TTA CTA CAT TCG CAC CTG CAA AAT AGC ACC    2231
Ser Asp His Thr Asp Gly Leu Leu His Ser His Leu Gln Asn Ser Thr
        290                 295                 300

ACT AAA CCA CCC GCC TCG AAG CAG CCG GCA CTG CCC AGA CTG GGA ATG    2279
Thr Lys Pro Pro Ala Ser Lys Gln Pro Ala Leu Pro Arg Leu Gly Met
    305                 310                 315

GGC CTG GGA TTG GGA TTG GGT CTC GGT CTG AAC CAG CCC ATC ATC ACC    2327
Gly Leu Gly Leu Gly Leu Gly Leu Gly Leu Asn Gln Pro Ile Ile Thr
320                 325                 330                 335

AAG CAG CCG ACA CCC GCC ACG CAA AAG GAG CGC ATG CAC GCG CTG GAG    2375
Lys Gln Pro Thr Pro Ala Thr Gln Lys Glu Arg Met His Ala Leu Glu
```

-continued

```
                       340                      345                      350
GAG CTG CTG CAA CCA GGC GGA GCC GGC GGC AAC GGA GGA CCC CTG GTG       2423
Glu Leu Leu Gln Pro Gly Gly Ala Gly Gly Asn Gly Gly Pro Leu Val
                355                      360                      365

ATG GCC GGC GAT CCC AGC CTG CTG AAT CCC ATC GTC TGT CCG CGA TGC       2471
Met Ala Gly Asp Pro Ser Leu Leu Asn Pro Ile Val Cys Pro Arg Cys
                370                      375                      380

GGT CGC TGT CGC TGC GAG CAG TGC CAG AGC CCC AGG CCA CTG CCC CAG       2519
Gly Arg Cys Arg Cys Glu Gln Cys Gln Ser Pro Arg Pro Leu Pro Gln
            385                      390                      395

ACG TGG GTG TGC AAC AAG ACG TGT CTG TGC AGC GCG GAG TCG GTT ATC       2567
Thr Trp Val Cys Asn Lys Thr Cys Leu Cys Ser Ala Glu Ser Val Ile
400                      405                      410                      415

GAC TAT GCC TCC TGC TTG TGC TGC GCC AAG GCT CTG TTC TAT CAC TGC       2615
Asp Tyr Ala Ser Cys Leu Cys Cys Ala Lys Ala Leu Phe Tyr His Cys
                420                      425                      430

GCC CGG GAC AAC GAC CTG GAC TGC GAT GAT GGC AAC GGC ACA CCC TGC       2663
Ala Arg Asp Asn Asp Leu Asp Cys Asp Asp Gly Asn Gly Thr Pro Cys
                435                      440                      445

GTG GAT AAT CCC TGC TCC TGC GGC CCC TAC AAG CGC ACC CAG AGA TGG       2711
Val Asp Asn Pro Cys Ser Cys Gly Pro Tyr Lys Arg Thr Gln Arg Trp
            450                      455                      460

GGC TGG CTG GGA GCA CTG TCG ATC TTC CTG CCC TGC CTG TGG TTC TAC       2759
Gly Trp Leu Gly Ala Leu Ser Ile Phe Leu Pro Cys Leu Trp Phe Tyr
465                      470                      475

TGG CCC ATG CGG GGC TGC ATG AAG CTG TGC GAG AAA TGC TAC GGC AGG       2807
Trp Pro Met Arg Gly Cys Met Lys Leu Cys Glu Lys Cys Tyr Gly Arg
480                      485                      490                      495

TTC GCC GGT CGG GGA TGC CGC TGT CAG GGC ATC GGC GGA GGA GGG GCA       2855
Phe Ala Gly Arg Gly Cys Arg Cys Gln Gly Ile Gly Gly Gly Gly Ala
                500                      505                      510

GGT TCC GGA GGC GGA GTC GGT AGC ATT GGA TCC ACC AGC AGC ATG CTG       2903
Gly Ser Gly Gly Gly Val Gly Ser Ile Gly Ser Thr Ser Ser Met Leu
            515                      520                      525

CCC ATA GTG CCT CTT GGG GTG AAT GGC AGT GGG CTG GGT GGC GGC GTG       2951
Pro Ile Val Pro Leu Gly Val Asn Gly Ser Gly Leu Gly Gly Gly Val
            530                      535                      540

AGC CTC TCC GGC GGC GTG ACG GAT GGT GGA CTC AAC CAA GCC AAT GGC       2999
Ser Leu Ser Gly Gly Val Thr Asp Gly Gly Leu Asn Gln Ala Asn Gly
545                      550                      555

AAG GCC ATG GAT CAT GGA TGC AGT GCC GCC AGG AGC ATA CTG CGA AAG       3047
Lys Ala Met Asp His Gly Cys Ser Ala Ala Arg Ser Ile Leu Arg Lys
560                      565                      570                      575

GGT GAC CTC ACC CCG GAG AAG CGG CTC CTG GAC TCC AGT CCC GAC TAC T     3096
Gly Asp Leu Thr Pro Glu Lys Arg Leu Leu Asp Ser Ser Pro Asp Tyr
                580                      585                      590

AAGGGTCCAT TCCATGTGTC CGGTTTTTTA CCCGAGCAAA AGCCTAAGG CACAAATGGG      3156

ATGCTGGATC GTGGACATAT ACACCCATAT ATATACGGAA AATATTTAAT ATATGATTTA     3216

AAAGGATATA TAAAAAAAGA GGAAAAAAAA AAAAAAGG                             3254
```

(2) INFORMATION FOR SEQ ID NO:2:

(i) SEQUENCE CHARACTERISTICS:
        (A) LENGTH: 591 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

```
Met Asp Arg Arg Asn Gly Gly Asp Pro Leu Ala Pro Pro Arg Pro Pro
 1               5                  10                  15

Lys Leu Leu Pro Arg Val His Arg Pro Arg Ala Pro Glu Pro Thr Leu
            20                  25                  30

Ser Gly Val Asp His Thr Ala Gly Ala Thr Ala Ser Ala Leu Ala Ser
        35                  40                  45

Gly Ala Ser Ser Ala Ala Pro Val Ala Ile His Asn Asn Asn Ser Gln
    50                  55                  60

Gln Gln Leu Ser Ile Ser Ala Ala Ala Ser Asn Asn Asn Thr Ile Ser
65                  70                  75                  80

Ile Ile Pro Ala Ser Pro Asp Phe Asp Asp Tyr Gln Ile His His Leu
                85                  90                  95

Thr Phe Leu Pro Gln Arg Pro Ser Ser Leu Ser Arg Asn Ser Ser Thr
            100                 105                 110

Ala Ser Ser Thr Thr Ala Thr Gly Ile Ser Val Ser Gly Ser Gly Ser
        115                 120                 125

Val Ser Gly Ser Ser Ser Ser Phe Thr Arg Arg Arg Pro Pro Ala Pro
    130                 135                 140

Val Pro Leu Asn Asn Ser Ile Ser Asn Asn Asn Asn Asn Ser Ile Asn
145                 150                 155                 160

Asn Asn Phe Leu Ser His Phe Gln Ser Ala Glu Pro Ala Ser Asn Ala
                165                 170                 175

Leu Gly Gln Pro Pro Ala Ser Pro Val Thr Leu Ala Gln Pro Arg Pro
            180                 185                 190

Glu Ser Glu Arg Leu Thr Asn Glu Tyr Val Asp Thr Pro Leu Gln His
        195                 200                 205

Ala Thr Arg Ser Gln His Pro Ala Gly Gln Gln Asp Asn Gly Gln Thr
    210                 215                 220

Thr Thr His His Leu Leu Leu Leu Pro Gln Arg Asn Gln His Leu His
225                 230                 235                 240

Leu Gln Gln His Gln Gln His Leu Gln Gln Gln Gln Gln Gln Gln Gln
                245                 250                 255

Gln Gln Gln Gln Gln Gln Gln Gln His Leu Gln His Gln Gln Asn Gln
            260                 265                 270

Gln His Ala Arg Leu Ala Thr Thr Thr Gln Ala Thr Ser Val Gly Ser
        275                 280                 285

Asp His Thr Asp Gly Leu Leu His Ser His Leu Gln Asn Ser Thr Thr
    290                 295                 300

Lys Pro Pro Ala Ser Lys Gln Pro Ala Leu Pro Arg Leu Gly Met Gly
305                 310                 315                 320

Leu Gly Leu Gly Leu Gly Leu Gly Leu Asn Gln Pro Ile Ile Thr Lys
                325                 330                 335

Gln Pro Thr Pro Ala Thr Gln Lys Glu Arg Met His Ala Leu Glu Glu
            340                 345                 350

Leu Leu Gln Pro Gly Gly Ala Gly Gly Asn Gly Gly Pro Leu Val Met
        355                 360                 365

Ala Gly Asp Pro Ser Leu Leu Asn Pro Ile Val Cys Pro Arg Cys Gly
    370                 375                 380

Arg Cys Arg Cys Glu Gln Cys Gln Ser Pro Arg Pro Leu Pro Gln Thr
385                 390                 395                 400
```

```
Trp Val Cys Asn Lys Thr Cys Leu Cys Ser Ala Glu Ser Val Ile Asp
            405                 410                 415

Tyr Ala Ser Cys Leu Cys Cys Ala Lys Ala Leu Phe Tyr His Cys Ala
            420                 425                 430

Arg Asp Asn Asp Leu Asp Cys Asp Asp Gly Asn Gly Thr Pro Cys Val
            435                 440                 445

Asp Asn Pro Cys Ser Cys Gly Pro Tyr Lys Arg Thr Gln Arg Trp Gly
            450                 455                 460

Trp Leu Gly Ala Leu Ser Ile Phe Leu Pro Cys Leu Trp Phe Tyr Trp
465                 470                 475                 480

Pro Met Arg Gly Cys Met Lys Leu Cys Glu Lys Cys Tyr Gly Arg Phe
            485                 490                 495

Ala Gly Arg Gly Cys Arg Cys Gln Gly Ile Gly Gly Gly Gly Ala Gly
            500                 505                 510

Ser Gly Gly Gly Val Gly Ser Ile Gly Ser Thr Ser Ser Met Leu Pro
            515                 520                 525

Ile Val Pro Leu Gly Val Asn Gly Ser Gly Leu Gly Gly Val Ser
            530                 535                 540

Leu Ser Gly Gly Val Thr Asp Gly Gly Leu Asn Gln Ala Asn Gly Lys
545                 550                 555                 560

Ala Met Asp His Gly Cys Ser Ala Ala Arg Ser Ile Leu Arg Lys Gly
            565                 570                 575

Asp Leu Thr Pro Glu Lys Arg Leu Leu Asp Ser Ser Pro Asp Tyr
            580                 585                 590

(2) INFORMATION FOR SEQ ID NO:3:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...372
        (D) OTHER INFORMATION:

(xi) SEQUENCE DESCRIPTION: SEQ ID NO:3:

TGT CCG CGA TGC GGT CGC TGT CGC TGC GAG CAG TGC CAG AGC CCC AGG        48
Cys Pro Arg Cys Gly Arg Cys Arg Cys Glu Gln Cys Gln Ser Pro Arg
1               5                   10                  15

CCA CTG CCC CAG ACG TGG GTG TGC AAC AAG ACG TGT CTG TGC AGC GCG        96
Pro Leu Pro Gln Thr Trp Val Cys Asn Lys Thr Cys Leu Cys Ser Ala
            20                  25                  30

GAG TCG GTT ATC GAC TAT GCC TCC TGC TTG TGC TGC GCC AAG GCT CTG       144
Glu Ser Val Ile Asp Tyr Ala Ser Cys Leu Cys Cys Ala Lys Ala Leu
        35                  40                  45

TTC TAT CAC TGC GCC CGG GAC AAC GAC CTG GAC TGC GAT GAT GGC AAC       192
Phe Tyr His Cys Ala Arg Asp Asn Asp Leu Asp Cys Asp Asp Gly Asn
    50                  55                  60

GGC ACA CCC TGC GTG GAT AAT CCC TGC TCC TGC GGC CCC TAC AAG CGC       240
Gly Thr Pro Cys Val Asp Asn Pro Cys Ser Cys Gly Pro Tyr Lys Arg
65                  70                  75                  80

ACC CAG AGA TGG GGC TGG CTG GGA GCA CTG TCG ATC TTC CTG CCC TGC       288
Thr Gln Arg Trp Gly Trp Leu Gly Ala Leu Ser Ile Phe Leu Pro Cys
                85                  90                  95

CTG TGG TTC TAC TGG CCC ATG CGG GGC TGC ATG AAG CTG TGC GAG AAA       336
```

```
Leu Trp Phe Tyr Trp Pro Met Arg Gly Cys Met Lys Leu Cys Glu Lys
            100                 105                 110

TGC TAC GGC AGG TTC GCC GGT CGG GGA TGC CGC TGT                          372
Cys Tyr Gly Arg Phe Ala Gly Arg Gly Cys Arg Cys
            115                 120
```

(2) INFORMATION FOR SEQ ID NO:4:

(i) SEQUENCE CHARACTERISTICS:
        (A) LENGTH: 124 amino acids
        (B) TYPE: amino acid
        (C) STRANDEDNESS: single
        (D) TOPOLOGY: linear (ii) MOLECULE TYPE: protein (v) FRAGMENT TYPE: internal (vi) ORIGINAL SOURCE:
        (C) INDIVIDUAL ISOLATE: d-spry cysteine-rich region (xi) SEQUENCE DESCRIPTION: SEQ ID NO:4:

```
Cys Pro Arg Cys Gly Arg Cys Arg Cys Glu Gln Cys Gln Ser Pro Arg
 1               5                  10                  15

Pro Leu Pro Gln Thr Trp Val Cys Asn Lys Thr Cys Leu Cys Ser Ala
            20                  25                  30

Glu Ser Val Ile Asp Tyr Ala Ser Cys Leu Cys Ala Lys Ala Leu
            35                  40                  45

Phe Tyr His Cys Ala Arg Asp Asn Asp Leu Asp Cys Asp Asp Gly Asn
 50                  55                  60

Gly Thr Pro Cys Val Asp Asn Pro Cys Ser Cys Gly Pro Tyr Lys Arg
65                  70                  75                  80

Thr Gln Arg Trp Gly Trp Leu Gly Ala Leu Ser Ile Phe Leu Pro Cys
            85                  90                  95

Leu Trp Phe Tyr Trp Pro Met Arg Gly Cys Met Lys Leu Cys Glu Lys
            100                 105                 110

Cys Tyr Gly Arg Phe Ala Gly Arg Gly Cys Arg Cys
            115                 120
```

(2) INFORMATION FOR SEQ ID NO:5:

(i) SEQUENCE CHARACTERISTICS:
        (A) LENGTH: 1604 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (C) INDIVIDUAL ISOLATE: h-spry1 cDNA (ix) FEATURE:
        (A) NAME/KEY: Coding Sequence
        (B) LOCATION: 1...417
        (D) OTHER INFORMATION:

(xi) SEQUENCE DESCRIPTION: SEQ ID NO:5:

```
TGT GAA CAG TGT GGG AAG TGC AAG TGT GGA GAA TGC ACT GCT CCC AGG          48
Cys Glu Gln Cys Gly Lys Cys Lys Cys Gly Glu Cys Thr Ala Pro Arg
 1               5                  10                  15

ACC CTA CCA TCC TGT TTG GCC TGT AAC CGG CAG TGC CTT TGC TCT GCT          96
Thr Leu Pro Ser Cys Leu Ala Cys Asn Arg Gln Cys Leu Cys Ser Ala
            20                  25                  30

GAG AGC ATG GTG GAA TAT GGA ACC TGC ATG TGC TTA GTC AAG GGC ATC         144
```

```
Glu Ser Met Val Glu Tyr Gly Thr Cys Met Cys Leu Val Lys Gly Ile
         35                  40                  45

TTC TAC CAC TGC TCC AAT GAC GAC GAA GGG GAT TCC TAT TCA GAT AAT        192
Phe Tyr His Cys Ser Asn Asp Asp Glu Gly Asp Ser Tyr Ser Asp Asn
     50                  55                  60

CCT TGC TCC TGT TCA CAA TCA CAC TGC TGC TCT AGA TAC CTG TGT ATG        240
Pro Cys Ser Cys Ser Gln Ser His Cys Cys Ser Arg Tyr Leu Cys Met
 65                  70                  75                  80

GGA GCC ATG TCT TTA TTT TTA CCT TGC TTA CTC TGT TAT CCT CCT GCT        288
Gly Ala Met Ser Leu Phe Leu Pro Cys Leu Leu Cys Tyr Pro Pro Ala
                 85                  90                  95

AAA GGA TGC CTG AAG CTG TGC AGG AGG TGT TAT GAC TGG ATC CAT CGC        336
Lys Gly Cys Leu Lys Leu Cys Arg Arg Cys Tyr Asp Trp Ile His Arg
            100                 105                 110

CCA GGG TGC AGA TGT AAG AAC TCC AAC ACT GTC TAT TGT AAG CTG GAG        384
Pro Gly Cys Arg Cys Lys Asn Ser Asn Thr Val Tyr Cys Lys Leu Glu
        115                 120                 125

AGC TGC CCC TCC CGG GGT CAG GGT AAA CCA TCA TGATTTTGG AGGTGGGTTG       437
Ser Cys Pro Ser Arg Gly Gln Gly Lys Pro Ser
        130                 135

TACCTCCTGA ACTTTTAGCT TTCAAGTTGT GGCTGTTTTT TGTTTTGTTT TGTTTGTTTT      497

CTTTAAATTT TCCGTTCCCT CCTTCCCCTG TTGCCAAGGT CTAACTCATG GATTTTCTC       557

TTTCCTCATG GATGATCTTC AGCAAGAGTG GACTGGGAAG CTGCACCTGG CTCCCACTTT      617

CAACAAGAGC CTCTGCCATC CACTTGAGGG TATTGAGAGC CAGTGGGCTT TTGTGTACCT      677

TTTTGTTCTG CAAGCAACTT TCTAAAGTTG TGTACATGAA CATACACCCA CATCCAGAAC      737

AGTGATTTAG AGTTGTTTTG ATTGGGTACC GTGGGAGCAG GGAAATTGGT TTTTTAAAAA      797

GCAACTGTTT AATTGCTTAA ATAAGCTATG TATTAAATCT GTCTCCAGTT AGGGCTATCT      857

TCCTAGCATA GGCCCCTTAA GTAGCATGGG GGAATTTTGT ATAACGTAAA AATTTCCTTT      917

AACCACTGCC CTCTCCTTCT TTTCCTTCAA GGTTTTTCCC CCTCAGTTTG TTGTTGTCTT      977

ATTGGAGATG CCAAGTGATT TTTTCTTTTA TGTAATTTTA GATTGCCTAC AATGTAAATT     1037

TCACATTGGA GATAATATTG GTTGGACCTC GCCCATCTTC ACTTAGCCTT CGTATTTGTG     1097

AAGGATTCAG CCACCTTCCT TCTTCACCCC ATGCTTCTCA CCAAAATTTT GTTGTCATTG     1157

AGGGCACTTG GATAACTCAA GTTGATATTT ATAGCTGATC AATCTATATG TGTCACAGAA     1217

CTATGCTGCC TAAAGTGATC TTGGCTCCTT AATGGTCCTT TTGGCCCCTT GGATAGTTAA     1277

CAGCTGAGTA ATTCTAATCT CTTCTGTGTT TTCCTTGCCT TAACCACAAA TTGTGGTGCT     1337

TTTTGTATAT TTTATGTATA AATCACAAAG TTGAATTCTG ACTATTTTTA AGACAAAAGT     1397

CTGTTAAACT TTTTTATTGT AAAGAATATT TATTATGCGA ATCTCTATTA TTTTATGGTA     1457

TTTATTGCAA AAGACTGTTG AAATGTACTC ATGTTTGAAT ATAACAAAAT ATCAATACTT     1517

AACGGAAAAT AAGGTGACAC GAAGAAAGTA CATATGTTAA CTATAATGCA GAAAATATAT     1577

TAATTAATGA AAAAAAAAAA AAAAAA                                         1604

(2) INFORMATION FOR SEQ ID NO:6:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (vi) ORIGINAL SOURCE:
```

(C) INDIVIDUAL ISOLATE: h-spry1 cysteine-rich region (xi) SEQUENCE DESCRIPTION: SEQ ID NO:6:

```
Cys Glu Gln Cys Gly Lys Cys Lys Cys Gly Glu Cys Thr Ala Pro Arg
1               5                   10                  15

Thr Leu Pro Ser Cys Leu Ala Cys Asn Arg Gln Cys Leu Cys Ser Ala
                20                  25                  30

Glu Ser Met Val Glu Tyr Gly Thr Cys Met Cys Leu Val Lys Gly Ile
            35                  40                  45

Phe Tyr His Cys Ser Asn Asp Asp Glu Gly Asp Ser Tyr Ser Asp Asn
        50                  55                  60

Pro Cys Ser Cys Ser Gln Ser His Cys Cys Ser Arg Tyr Leu Cys Met
65                  70                  75                  80

Gly Ala Met Ser Leu Phe Leu Pro Cys Leu Leu Cys Tyr Pro Pro Ala
                85                  90                  95

Lys Gly Cys Leu Lys Leu Xaa Arg Arg Cys Tyr Asp Trp Ile His Arg
                100                 105                 110

Pro Gly Cys Arg Cys
        115
```

(2) INFORMATION FOR SEQ ID NO:7:

(i) SEQUENCE CHARACTERISTICS:
        (A) LENGTH: 2135 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (C) INDIVIDUAL ISOLATE: h-spry2 cDNA (ix) FEATURE:
        (A) NAME/KEY: Coding Sequence
        (B) LOCATION: 391...1335
        (D) OTHER INFORMATION:

(xi) SEQUENCE DESCRIPTION: SEQ ID NO:7:

```
GGCACGAGGG TAAGGCCGTT TTCTTTTCCC ATTCGCTCAT CTGCCAGGAA AAGGGACTTG    60

CCGTTGGCGC TTCGGCCTCT TGTTCATTGA GAAAAAAGAG GAAATACTCC GCGTGCGCTT   120

GTAGAAGGGG AGTCGTCTCC AGCTCCGAAC CCCGGAGTGT TCATCAGCGG GGAATCTGGC   180

TCCGAATTCT CTTTTTTTCT CCCGCCGATT GCTCGGAAGT TGGTCTAAAG CAGAGGTTGG   240

AAAGAAAGGA AAAAAGTTTG CATCGAGACT GGATTTATTT GCACATCGCA GAAAGAAGAG   300

AATCCAAGGG AGAGGGGTTG GTGCAAAGCC GCGATCACGG AGTTCAGATG TGTTCTAAGC   360

CTGCTGGAGT GACCACACTT CCAAGACCTG ATG GAG GCC AGA GCT CAG AGT GGC   414
                                Met Glu Ala Arg Ala Gln Ser Gly
                                1               5

AAC GGG TCG CAG CCC TTG CTG CAG ACG CCC CGT GAC GGT GGC AGA CAG   462
Asn Gly Ser Gln Pro Leu Leu Gln Thr Pro Arg Asp Gly Gly Arg Gln
    10                  15                  20

CGT GGG GAG CCC GAC CCC AGA GAC GCC CTC ACC CAG CAG GTA CAT GTC   510
Arg Gly Glu Pro Asp Pro Arg Asp Ala Leu Thr Gln Gln Val His Val
25                  30                  35                  40

TTG TCT CTG GAT CAG ATC AGA GCC ATC CGA AAC ACC AAT GAG TAC ACA   558
Leu Ser Leu Asp Gln Ile Arg Ala Ile Arg Asn Thr Asn Glu Tyr Thr
                45                  50                  55

GAG GGG CCT ACT GTC GTC CCA AGA CCT GGG CTC AAG CCT GCT CCT CGC   606
Glu Gly Pro Thr Val Val Pro Arg Pro Gly Leu Lys Pro Ala Pro Arg
```

-continued

```
              60                      65                      70
CCC TCC ACT CAG CAC AAA CAC GAG AGA CTC CAC GGT CTG CCT GAG CAC       654
Pro Ser Thr Gln His Lys His Glu Arg Leu His Gly Leu Pro Glu His
             75                      80                      85

CGC CAG CCT CCT AGG CTC CAG CAC TCG CAG GTC CAT TCT TCT GCA CGA       702
Arg Gln Pro Pro Arg Leu Gln His Ser Gln Val His Ser Ser Ala Arg
         90                      95                     100

GCC CCT CTG TCC AGA TCC ATA AGC ACG GTC AGC TCA GGG TCG CGG AGC       750
Ala Pro Leu Ser Arg Ser Ile Ser Thr Val Ser Ser Gly Ser Arg Ser
105                     110                     115                     120

AGT ACG AGG ACA AGT ACC AGC AGC AGC TCC TCT GAA CAG AGA CTG CTA       798
Ser Thr Arg Thr Ser Thr Ser Ser Ser Ser Ser Glu Gln Arg Leu Leu
             125                     130                     135

GGA TCA TCC TTC TCC TCC GGG CCT GTT GCT GAT GGC ATA ATC CGG GTG       846
Gly Ser Ser Phe Ser Ser Gly Pro Val Ala Asp Gly Ile Ile Arg Val
             140                     145                     150

CAA CCC AAA TCT GAG CTC AAG CCA GGT GAG CTT AAG CCA CTG AGC AAG       894
Gln Pro Lys Ser Glu Leu Lys Pro Gly Glu Leu Lys Pro Leu Ser Lys
             155                     160                     165

GAA GAT TTG GGC CTG CAC GCC TAC AGG TGT GAG GAC TGT GGC AAG TGC       942
Glu Asp Leu Gly Leu His Ala Tyr Arg Cys Glu Asp Cys Gly Lys Cys
         170                     175                     180

AAA TGT AAG GAG TGC ACC TAC CCA AGG CCT CTG CCA TCA GAC TGG ATC       990
Lys Cys Lys Glu Cys Thr Tyr Pro Arg Pro Leu Pro Ser Asp Trp Ile
185                     190                     195                     200

TGC GAC AAG CAG TGC CTT TGC TCG GCC CAG AAC GTG ATT GAC TAT GGG      1038
Cys Asp Lys Gln Cys Leu Cys Ser Ala Gln Asn Val Ile Asp Tyr Gly
             205                     210                     215

ACT TGT GTA TGC TGT GTG AAA GGT CTC TTC TAT CAC TGT TCT AAT GAT      1086
Thr Cys Val Cys Cys Val Lys Gly Leu Phe Tyr His Cys Ser Asn Asp
             220                     225                     230

GAT GAG GAC AAC TGT GCT GAC AAC CCA TGT TCT TGC AGC CAG TCT CAC      1134
Asp Glu Asp Asn Cys Ala Asp Asn Pro Cys Ser Cys Ser Gln Ser His
             235                     240                     245

TGT TGT ACA CGA TGG TCA GCC ATG GGT GTC ATG TCC CTC TTT TTG CCT      1182
Cys Cys Thr Arg Trp Ser Ala Met Gly Val Met Ser Leu Phe Leu Pro
250                     255                     260

TGT TTA TGG TGT TAC CTT CCA GCC AAG GGT TGC CTT AAA TTG TGC CAG      1230
Cys Leu Trp Cys Tyr Leu Pro Ala Lys Gly Cys Leu Lys Leu Cys Gln
265                     270                     275                     280

GGG TGT TAT GAC CGG GTT AAC AGG CCT GGT TGC CGC TGT AAA AAC TCA      1278
Gly Cys Tyr Asp Arg Val Asn Arg Pro Gly Cys Arg Cys Lys Asn Ser
             285                     290                     295

AAC ACA GTT TGC TGC AAA GTT CCC ACT GTC CCC CCT AGG AAC TTT GAA      1326
Asn Thr Val Cys Cys Lys Val Pro Thr Val Pro Pro Arg Asn Phe Glu
             300                     305                     310

AAA CCA ACA TAGCATCATT AATCAGGAAT ATTACAGTAA TGAGGATTTT TTCTTTCTT    1384
Lys Pro Thr
         315

TTTTTAATAC ACATATGCAA CCAACTAAAC AGTTATAATC TTGGCACTGT TAATCGAAAG    1444

TTGGGATAGT CTTTGCTGTT TGCGGTGAAA TGCTTTTTGT CCATGTGCCG TTTTAACTGA    1504

TATGCTTGTT AGAACTCAGC TAATGGAGCT CAAAGTATGA GATACAGAAC TTGGTGACCC    1564

ATGTATTGCA TAAGCTAAAG CAACACAGAC ACTCCTAGGC AAAGTTTTTG TTTGTGAATA    1624

GTACTTGCAA AACTTGTAAA TTAGCAGATG ACTTTTTTCC ATTGTTTTCT CCAGAGAGAA    1684

TGTGCTATAT TTTTGTATAT ACAATAATAT TTGCAACTGT GAAAACAAG TTGTGCCATA     1744

CTACATGGCA CAGACACAAA ATATTATACT AATATGTTGT ACATTCGGAA GAATGTGAAT    1804
```

```
CAATCAGTAT GTTTTTAGAT TGTATTTTGC CTTACAGAAA GCCTTTATTG TAAGACTCTG    1864

ATTTCCCTTT GGACTTCATG TATATTGTAC AGTTACAGTA AAATTCAACC TTTATTTTCT    1924

AATTTTTTCA ACATATTGTT TAGTGTAAAG AATATTTATT TGAAGTTTTA TTATTTTATA    1984

AAAAAGAATA TTTATTTTAA GAGGCATCTT ACAAATTTTG CCCCTTTTAT GAGGATGTGA    2044

TAGTTGCTGC AAATGAGGGG TTACAGATGC ATATGTCCAA TATAAAATAG AAAATATATT    2104

AACGTTTGAA ATTAAAAAAA AAAAAAAAA A                                   2135
```

(2) INFORMATION FOR SEQ ID NO:8:

(i) SEQUENCE CHARACTERISTICS:
        (A) LENGTH: 315 amino acids
        (B) TYPE: amino acid
        (C) STRANDEDNESS: single
        (D) TOPOLOGY: linear (ii) MOLECULE TYPE: protein (v) FRAGMENT TYPE: internal (vi) ORIGINAL SOURCE:
        (C) INDIVIDUAL ISOLATE: h-spry2 protein (xi) SEQUENCE DESCRIPTION: SEQ ID NO:8:

```
Met Glu Ala Arg Ala Gln Ser Gly Asn Gly Ser Gln Pro Leu Leu Gln
 1               5                  10                  15

Thr Pro Arg Asp Gly Arg Gln Arg Gly Glu Pro Asp Pro Arg Asp
            20                  25                  30

Ala Leu Thr Gln Gln Val His Val Leu Ser Leu Asp Gln Ile Arg Ala
        35                  40                  45

Ile Arg Asn Thr Asn Glu Tyr Thr Glu Gly Pro Thr Val Val Pro Arg
 50                  55                  60

Pro Gly Leu Lys Pro Ala Pro Arg Pro Ser Thr Gln His Lys His Glu
65                  70                  75                  80

Arg Leu His Gly Leu Pro Glu His Arg Gln Pro Pro Arg Leu Gln His
                85                  90                  95

Ser Gln Val His Ser Ser Ala Arg Ala Pro Leu Ser Arg Ser Ile Ser
            100                 105                 110

Thr Val Ser Ser Gly Ser Arg Ser Ser Thr Arg Thr Ser Thr Ser Ser
        115                 120                 125

Ser Ser Ser Glu Gln Arg Leu Leu Gly Ser Ser Phe Ser Ser Gly Pro
    130                 135                 140

Val Ala Asp Gly Ile Ile Arg Val Gln Pro Lys Ser Glu Leu Lys Pro
145                 150                 155                 160

Gly Glu Leu Lys Pro Leu Ser Lys Glu Asp Leu Gly Leu His Ala Tyr
                165                 170                 175

Arg Cys Glu Asp Cys Gly Lys Cys Lys Cys Lys Glu Cys Thr Tyr Pro
            180                 185                 190

Arg Pro Leu Pro Ser Asp Trp Ile Cys Asp Lys Gln Cys Leu Cys Ser
        195                 200                 205

Ala Gln Asn Val Ile Asp Tyr Gly Thr Cys Val Cys Cys Val Lys Gly
    210                 215                 220

Leu Phe Tyr His Cys Ser Asn Asp Asp Glu Asp Asn Cys Ala Asp Asn
225                 230                 235                 240

Pro Cys Ser Cys Ser Gln Ser His Cys Cys Thr Arg Trp Ser Ala Met
                245                 250                 255
```

```
Gly Val Met Ser Leu Phe Leu Pro Cys Leu Trp Cys Tyr Leu Pro Ala
            260                 265                 270

Lys Gly Cys Leu Lys Leu Cys Gln Gly Cys Tyr Asp Arg Val Asn Arg
            275                 280                 285

Pro Gly Cys Arg Cys Lys Asn Ser Asn Thr Val Cys Cys Lys Val Pro
            290                 295                 300

Thr Val Pro Pro Arg Asn Phe Glu Lys Pro Thr
305                 310                 315
```

(2) INFORMATION FOR SEQ ID NO:9:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: protein (vi) ORIGINAL SOURCE:
        (C) INDIVIDUAL ISOLATE: h-spry2 cysteine-rich region (xi) SEQUENCE DESCRIPTION: SEQ ID NO:9:

```
Cys Glu Asp Cys Gly Lys Cys Lys Cys Lys Glu Cys Thr Tyr Pro Arg
1               5                   10                  15

Pro Leu Pro Ser Asp Trp Ile Cys Asp Lys Gln Cys Leu Cys Ser Ala
            20                  25                  30

Gln Asn Val Ile Asp Tyr Gly Thr Cys Val Cys Cys Val Lys Gly Leu
            35                  40                  45

Phe Tyr His Cys Ser Asn Asp Asp Glu Asp Asn Cys Ala Asp Asn Pro
    50                  55                  60

Cys Ser Cys Ser Gln Ser His Cys Cys Thr Arg Trp Ser Ala Met Gly
65              70                  75                  80

Val Met Ser Leu Phe Leu Pro Cys Leu Trp Cys Tyr Leu Pro Ala Lys
                85                  90                  95

Gly Cys Leu Lys Leu Cys Gln Gly Cys Tyr Asp Arg Val Asn Arg Pro
            100                 105                 110

Gly Cys Arg Cys
            115
```

(2) INFORMATION FOR SEQ ID NO:10:

(i) SEQUENCE CHARACTERISTICS:
        (A) LENGTH: 300 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (C) INDIVIDUAL ISOLATE: h-spry3

(ix) FEATURE:
        (A) NAME/KEY: Coding Sequence
        (B) LOCATION: 1...300
        (D) OTHER INFORMATION:

(xi) SEQUENCE DESCRIPTION: SEQ ID NO:10:

```
CCC CTG CCT CTT GAT CAA AGG CTC CTG GCC AGC ATT ACA CCC TCA CCT        48
Pro Leu Pro Leu Asp Gln Arg Leu Leu Ala Ser Ile Thr Pro Ser Pro
1               5                   10                  15

TCA GGC CAA TCC ATC ATC CGA ACC CAA CCT GGA GCA GGG GTC CAC CCA        96
Ser Gly Gln Ser Ile Ile Arg Thr Gln Pro Gly Ala Gly Val His Pro
```

-continued

```
            20                    25                   30
AAG GCT GAT GGT GCT CTG AAG GGA GAA GCT GAG CAA TCT GCA GGG CAC        144
Lys Ala Asp Gly Ala Leu Lys Gly Glu Ala Glu Gln Ser Ala Gly His
        35                   40                   45

CCT AGT GAG CAC CTC TTC ATC TGT GAG GAA TGT GGG CGC TGC AAG TGC        192
Pro Ser Glu His Leu Phe Ile Cys Glu Glu Cys Gly Arg Cys Lys Cys
    50                   55                   60

GTC CCC TGC ACA GCA GCT CGC CCT CTC CCC TCC TGC TGG CTG TGC AAC        240
Val Pro Cys Thr Ala Ala Arg Pro Leu Pro Ser Cys Trp Leu Cys Asn
65                   70                   75                   80

CAG CGC TGC CTT TGC TCT GCT GAG AGC CTC CTC GAT TAT GGC ACT TGT        288
Gln Arg Cys Leu Cys Ser Ala Glu Ser Leu Leu Asp Tyr Gly Thr Cys
                85                   90                   95

CTC TGC TGT GTC                                                        300
Leu Cys Cys Val
            100
```

(2) INFORMATION FOR SEQ ID NO:11:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: protein (v) FRAGMENT TYPE: internal (vi) ORIGINAL SOURCE:
        (C) INDIVIDUAL ISOLATE: h-spry3 cysteine-rich region (xi) SEQUENCE DESCRIPTION: SEQ ID NO:11:

```
Pro Leu Pro Leu Asp Gln Arg Leu Leu Ala Ser Ile Thr Pro Ser Pro
1               5                   10                  15

Ser Gly Gln Ser Ile Ile Arg Thr Gln Pro Gly Ala Gly Val His Pro
            20                  25                  30

Lys Ala Asp Gly Ala Leu Lys Gly Glu Ala Glu Gln Ser Ala Gly His
        35                  40                  45

Pro Ser Glu His Leu Phe Ile Cys Glu Glu Cys Gly Arg Cys Lys Cys
    50                  55                  60

Val Pro Cys Thr Ala Ala Arg Pro Leu Pro Ser Cys Trp Leu Cys Asn
65                  70                  75                  80

Gln Arg Cys Leu Cys Ser Ala Glu Ser Leu Leu Asp Tyr Gly Thr Cys
                85                  90                  95

Leu Cys Cys Val
            100
```

(2) INFORMATION FOR SEQ ID NO:12:

(i) SEQUENCE CHARACTERISTICS:
        (A) LENGTH: 252 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (C) INDIVIDUAL ISOLATE: m-spry1

(ix) FEATURE:
        (A) NAME/KEY: Coding Sequence
        (B) LOCATION: 2...250
        (D) OTHER INFORMATION:

(xi) SEQUENCE DESCRIPTION: SEQ ID NO:12:

| G GCC TCC TTG AAA GAG GAC CCC ACC CAG CAC AAG TTC ATC TGC GAA CAG | 49 |
|---|---|
|   Ala Ser Leu Lys Glu Asp Pro Thr Gln His Lys Phe Ile Cys Glu Gln | |
|    1           5               10               15 | |

TGT GGC AAG TGC AAA TGT GGA GAG TGT ACG GCC CCC CGG CGC ATG CCA     97
Cys Gly Lys Cys Lys Cys Gly Glu Cys Thr Ala Pro Arg Arg Met Pro
        20                25               30

TCC TGT CTG GCC TGT GAT CGG CAG TGC CTC TGC TCC GCG GAG AGC ATG    145
Ser Cys Leu Ala Cys Asp Arg Gln Cys Leu Cys Ser Ala Glu Ser Met
        35                40               45

GTG GAA TAC GGG ACC TGC ATG TGC CTG GTC AAG GGC ATT TTC TAC CAC    193
Val Glu Tyr Gly Thr Cys Met Cys Leu Val Lys Gly Ile Phe Tyr His
        50                55               60

AGC TCC AAT GAT GCT GAT GGA GGT TCT TAC TCG GAT AAC CCA TGC TCC    241
Ser Ser Asn Asp Ala Asp Gly Gly Ser Tyr Ser Asp Asn Pro Cys Ser
65               70                75               80

TGT TCA CAG TC                                                                      252
Cys Ser Gln (2) INFORMATION FOR SEQ ID NO:13:

(i) SEQUENCE CHARACTERISTICS:
        (A) LENGTH: 83 amino acids
        (B) TYPE: amino acid
        (C) STRANDEDNESS: single
        (D) TOPOLOGY: linear (ii) MOLECULE TYPE: protein (v) FRAGMENT TYPE: internal (vi) ORIGINAL SOURCE:
        (C) INDIVIDUAL ISOLATE: m-spry1 cysteine-rich region (xi) SEQUENCE DESCRIPTION: SEQ ID NO:13:

Ala Ser Leu Lys Glu Asp Pro Thr Gln His Lys Phe Ile Cys Glu Gln
  1           5              10             15

Cys Gly Lys Cys Lys Cys Gly Glu Cys Thr Ala Pro Arg Arg Met Pro
        20                25               30

Ser Cys Leu Ala Cys Asp Arg Gln Cys Leu Cys Ser Ala Glu Ser Met
        35                40               45

Val Glu Tyr Gly Thr Cys Met Cys Leu Val Lys Gly Ile Phe Tyr His
        50                55               60

Ser Ser Asn Asp Ala Asp Gly Gly Ser Tyr Ser Asp Asn Pro Cys Ser
65               70                75               80

Cys Ser Gln (2) INFORMATION FOR SEQ ID NO:14:

(i) SEQUENCE CHARACTERISTICS:
        (A) LENGTH: 504 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (C) INDIVIDUAL ISOLATE: m-spry2

(xi) SEQUENCE DESCRIPTION: SEQ ID NO:14:

AATTTCAAAC GTTAATATAT TTTCTATTTT ATATTGAACA TAGCATCTGT AACCTCTCCT    60

```
TGGCAGCAAC CATCACATCC TCATAAAAGG GGCAAAATTT ATGATGCCTC TTAAAATAAA    120

TATTCTTTTT TTTTATAAAA TAATAAAACT TCAAATAAAT ATTCTTTACA CTAAACAATA    180

TGTTGAAAAA ATTAGAAAAT AAAGGTTGAA TTTTACTGTA ACTGTACAAT ATACATCAAG    240

TCCAAAGGGA AATCAGAGAC TTACAATAAA GGTTTCCTGT AAGGCAAAAT ACAATCTAAA    300

AACATACTGA TTGATTCACA TTCTTCCGAA TGTACAACAT ATTAGTATAA TATTTGTGA     360

CTGTGCCATG AAGCATAGCA CAACTTGTTT TTTTTCACAG TTGCAAATAT TATCGTATAT    420

ACAAAAATAT AGCACATTAT CTCTGGAGAA AACAAGGAGG GGTCCGGGAG CCATTTGCTA    480

ATTTACACAT TTTGCATGGG CTAT                                          504

(2) INFORMATION FOR SEQ ID NO:15:

(i) SEQUENCE CHARACTERISTICS:
        (A) LENGTH: 456 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (C) INDIVIDUAL ISOLATE: m-spry4

(ix) FEATURE:
         (A) NAME/KEY: Coding Sequence
         (B) LOCATION: 3...353
         (D) OTHER INFORMATION:

(xi) SEQUENCE DESCRIPTION: SEQ ID NO:15:

GC AAC CAG GAG TGC CTG TGC TCG GCT CAG ACG CTG GTC AAC TAT GGC        47
   Asn Gln Glu Cys Leu Cys Ser Ala Gln Thr Leu Val Asn Tyr Gly
   1               5                  10                  15

ACA TGC ATG TGT CTG GTG CAA GGT ATC TTC TAT CAC TGT ACT AAT GAG       95
Thr Cys Met Cys Leu Val Gln Gly Ile Phe Tyr His Cys Thr Asn Glu
                20                  25                  30

GAT GAT GAG GGC TCT TGC GCC GAC CAC CCC TGC TCC TGT TCC GGC TCC      143
Asp Asp Glu Gly Ser Cys Ala Asp His Pro Cys Ser Cys Ser Gly Ser
            35                  40                  45

AAC TGC TGC GCC CGC TGG TCC TTC ATG GGC GCC CTC TCT GTG GTG CTG      191
Asn Cys Cys Ala Arg Trp Ser Phe Met Gly Ala Leu Ser Val Val Leu
        50                  55                  60

CCC TGT CTG CTG TGC TAC CTG CCG GCC ACA GGC TGC GTC AAG CTG GCC      239
Pro Cys Leu Leu Cys Tyr Leu Pro Ala Thr Gly Cys Val Lys Leu Ala
    65                  70                  75

CAG CGA GGC TAC GAC CGC CTG AGA CGC CCC GGT TGC CGC TGC AAG CAC      287
Gln Arg Gly Tyr Asp Arg Leu Arg Arg Pro Gly Cys Arg Cys Lys His
80                  85                  90                  95

ACG AAC AGC GTC ATC TGC AAG GCA GCA AGT GGG GAC ACC AAG ACC AGC      335
Thr Asn Ser Val Ile Cys Lys Ala Ala Ser Gly Asp Thr Lys Thr Ser
                100                 105                 110

AGG TCT GAC AAG CCT TTC TGACACTTTG GATGAAAAAA ACATGGTCCC TCCTGCCA    391
Arg Ser Asp Lys Pro Phe
            115

GTCTCCTGAG ACTGACCTTG CTCATCTGTC CTCTCTAAAA CCCTAGATTG GGAAGAAACC    451

GGCAG                                                                456

(2) INFORMATION FOR SEQ ID NO:16:

(i) SEQUENCE CHARACTERISTICS:
        (A) LENGTH: 117 amino acids
        (B) TYPE: amino acid
```

(C) STRANDEDNESS: single
(D) TOPOLOGY: linear (ii) MOLECULE TYPE: protein (v) FRAGMENT TYPE: internal (vi) ORIGINAL SOURCE:
(C) INDIVIDUAL ISOLATE: m-spry4 cysteine-rich region (xi) SEQUENCE DESCRIPTION: SEQ ID NO:16:

```
Asn Gln Glu Cys Leu Cys Ser Ala Gln Thr Leu Val Asn Tyr Gly Thr
1               5                   10                  15
Cys Met Cys Leu Val Gln Gly Ile Phe Tyr His Cys Thr Asn Glu Asp
            20                  25                  30
Asp Glu Gly Ser Cys Ala Asp His Pro Cys Ser Cys Ser Gly Ser Asn
        35                  40                  45
Cys Cys Ala Arg Trp Ser Phe Met Gly Ala Leu Ser Val Val Leu Pro
50                  55                  60
Cys Leu Leu Cys Tyr Leu Pro Ala Thr Gly Cys Val Lys Leu Ala Gln
65                  70                  75                  80
Arg Gly Tyr Asp Arg Leu Arg Arg Pro Gly Cys Arg Cys Lys His Thr
                85                  90                  95
Asn Ser Val Ile Cys Lys Ala Ala Ser Gly Asp Thr Lys Thr Ser Arg
            100                 105                 110
Ser Asp Lys Pro Phe
        115
```

(2) INFORMATION FOR SEQ ID NO:17:

(i) SEQUENCE CHARACTERISTICS:
(A) LENGTH: 45 amino acids
(B) TYPE: amino acid
(C) STRANDEDNESS: single
(D) TOPOLOGY: linear (ii) MOLECULE TYPE: protein (vi) ORIGINAL SOURCE:
(C) INDIVIDUAL ISOLATE: h-spry2 highly conserved cysteine-rich region (xi) SEQUENCE DESCRIPTION: SEQ ID NO:17:

```
Cys Glu Asp Cys Gly Lys Cys Lys Cys Lys Glu Cys Thr Tyr Pro Arg
1               5                   10                  15
Pro Leu Pro Ser Asp Trp Ile Cys Asp Lys Gln Cys Leu Cys Ser Ala
            20                  25                  30
Gln Asn Val Ile Asp Tyr Gly Thr Cys Val Cys Cys Val
        35                  40                  45
```

(2) INFORMATION FOR SEQ ID NO:18:

(i) SEQUENCE CHARACTERISTICS:
(A) LENGTH: 45 amino acids
(B) TYPE: amino acid
(C) STRANDEDNESS: single
(D) TOPOLOGY: linear (ii) MOLECULE TYPE: protein (vi) ORIGINAL SOURCE:
(C) INDIVIDUAL ISOLATE: h-spry1 highly conserved cysteine-rich region (xi) SEQUENCE DESCRIPTION: SEQ ID NO:18:

```
Cys Glu Gln Cys Gly Lys Cys Lys Cys Gly Glu Cys Thr Ala Pro Arg
 1               5                  10                  15

Thr Leu Pro Ser Cys Leu Ala Cys Asn Arg Gln Cys Leu Cys Ser Ala
            20                  25                  30

Glu Ser Met Val Glu Tyr Gly Thr Cys Met Cys Leu Val
            35                  40                  45
```

(2) INFORMATION FOR SEQ ID NO:19:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: protein (vi) ORIGINAL SOURCE:
        (C) INDIVIDUAL ISOLATE: h-spry3 highly conserved cysteine-rich
            region (xi) SEQUENCE DESCRIPTION: SEQ ID NO:19:

```
Cys Glu Glu Cys Gly Arg Cys Lys Cys Val Pro Cys Thr Ala Ala Arg
 1               5                  10                  15

Pro Leu Pro Ser Cys Trp Leu Cys Asn Gln Arg Cys Leu Cys Ser Ala
            20                  25                  30

Glu Ser Leu Leu Asp Tyr Gly Thr Cys Leu Cys Val
            35                  40                  45
```

(2) INFORMATION FOR SEQ ID NO:20:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (v) FRAGMENT TYPE: internal (vi) ORIGINAL SOURCE:
        (C) INDIVIDUAL ISOLATE: h-spry1

(xi) SEQUENCE DESCRIPTION: SEQ ID NO:20:

```
Cys Glu Gln Cys Gly Lys Cys Lys Cys Gly Glu Cys Thr Ala Pro Arg
 1               5                  10                  15

Thr Leu Pro Ser Cys Leu Ala Cys Asn Arg Gln Cys Leu Cys Ser Ala
            20                  25                  30

Glu Ser Met Val Glu Tyr Gly Thr Cys Met Cys Leu Val Lys Gly Ile
            35                  40                  45

Phe Tyr His Cys Ser Asn Asp Asp Glu Gly Asp Ser Tyr Ser Asp Asn
            50                  55                  60

Pro Cys Ser Cys Ser Gln Ser His Cys Cys Ser Arg Tyr Leu Cys Met
65                  70                  75                  80

Gly Ala Met Ser Leu Phe Leu Pro Cys Leu Leu Cys Tyr Pro Pro Ala
            85                  90                  95

Lys Gly Cys Leu Lys Leu Cys Arg Arg Cys Tyr Asp Trp Ile His Arg
```

-continued

```
                    100                 105                 110
Pro Gly Cys Arg Cys Lys Asn Ser Asn Thr Val Tyr Cys Lys Leu Glu
        115                 120                 125

Ser Cys Pro Ser Arg Gly Gln Gly Lys Pro Ser
130                 135
```